(12) United States Patent
Shi et al.

(10) Patent No.: US 8,962,322 B2
(45) Date of Patent: Feb. 24, 2015

(54) ENHANCERS OF INDUCED PLURIPOTENT STEM CELL REPROGRAMMING

(71) Applicant: City of Hope, Duarte, CA (US)

(72) Inventors: Yanhong Shi, Arcadia, CA (US); Man Lun Yip, Honolulu, HI (US); Wendong Li, Duarte, CA (US)

(73) Assignee: City of Hope, Duarte ( * ) Notice: Subject to any disclaimer, the term of this patent is extended or adjusted under 35 U.S.C. 154(b) by 0 days.

(21) Appl. No.: 14/054,551

(22) Filed: Oct. 15, 2013

(65) Prior Publication Data

US 2014/0154805 A1 Jun. 5, 2014

Related U.S. Application Data

(60) Provisional application No. 61/732,875, filed on Dec. 3, 2012.

(51) Int. Cl.
*C12N 5/00* (2006.01)
*C12N 5/074* (2010.01)

(52) U.S. Cl.
CPC ........ *C12N 5/0696* (2013.01); *C12N 2501/603* (2013.01)
USPC .......................................... 435/377; 435/325

(58) Field of Classification Search
USPC ................................................. 435/377, 325
See application file for complete search history.

(56) References Cited

PUBLICATIONS

Anokye-Danso, F, et al. (2011) Highly Efficient miRNA-Mediated Reprogramming of Mouse and Human Somatic Cells to Pluripotency. *Cell Stem Cell* 8, 376-388.
Banito, A, et al. (2009) Sensescence impairs successful reprogramming to pluripotent stem cells. *Genes & Dev* 23, 2134-2139.
Boyer, LA, et al. (2005) Core transcriptional regulatory circuitry in human embryonic stem cells. *Cell* 122, 947-956.
Chambers, I, et al. (2003) Functional expression cloning of Nanog, a pluripotency sustaining factor in embryonic stem cells. *Cell* 113, 643-655.
Chen, J, et al. (2010) Towards an optimized culture medium for the generation of mouse induced pluripotent stem cells. *JBC* 285, 31066-31072.
Dawlaty, MM, et al. (2011) Tet1 is dispensable for maintaining pluipotency and its loss is compatible with embryonic and postnatal development. *Cell Stem Cell* 9, 166-175.
De Los Angeles, A. & Daley, G.(2013) A chemical logic for reprogramming to pluripotency. *Cell Research* advance online publication Aug. 27, 2013; doi 10.1038/cr.2013.119, 2 pages.
Esteban, MA, et al. (2010) Vitamin C enhances the generation of mouse and human induced pluripotent stem cells. *Cell Stem Cell* 6, 71-79.

Freudenberg, JM, et al. (2012) Acute depletion fo Tet1-dependent 5-hydroxymethylcytosine levels impairs LIF/Stat3 signaling and results in loss of embryonic stem cell identity. *Nucleic Acids Research* 40, 3364-3377.
Gonzalez, F, Boue, S & Izpisua Belmonte, JC (2011) Methods for making induced pluripotent stem cells: reprogramming a la carte. *Nat Rev Genet* 12, 231-242.
Heng, JC, et al. (2010) The nuclear receptor Nr5a2 can replace Oct4 in the reprogramming of murine somatic cells to pluripotent cells, *Cell Stem Cell* 6, 167-174.
Hong, H, et al. (2009) Suppression of induced pluripotent stem cell generation by the p53-p21 pathway. *Nature* 460, 1132-1135.
Hou, P, et al. (2013) Pluripotent Stem Cells Induced from Mouse Somatic Cells by Small-Molecule Compounds. *Science* 341: 651-654.
Huangfu, D, et al. (2008) Induction of pluripotent stem cells by defined factors is greatly improved by small-molecule compounds. *Nature Biotechnology* 26, 795-797.
Huangfu, D, et al. (2008) Induction of pluripotent stem cells from primary human fibroblasts with only Oct4 and Sox2. *Nature Biotechnology* 26, 1269-1275.
Ichida, JK, et al. (2009) A small-molecule inhibitor of tgf-Beta signaling replaces sox2 in reprogramming by inducing nanog. *Cell Stem Cell* 5, 491-503.
Ito, S, et al. (2010) Role of Tet proteins in 5mC to 5hmC conversion, ES-cell self-renewal and inner cell mass specification. *Nature* 466, 1129-1133.
Jaenisch, R & Young R (2008) Stem cells, the molecular circuitry of pluripotency and nuclear reprogramming. *Cell* 132, 567-582.
Judson, RL, Babiarz, JE, Venere, M, & Blelloch, R (2009) Embryonic stem cell-specific microRNAs promote induced pluripotency. *Nature Biotechnology* 27, 459-461.
Kawamurea, T, et al. (2009) Linking the p53 tumour suppressor pathway to somatic cell reprogramming. *Nature* 460, 1140-1144.
Kim, JB, et al. (2009) Direct reprogramming of human neural stem cells by OCT4. *Nature* 461, 649-643.
Kim, JB, et al. (2009) Oct4-induced pluripotency in adult neural stem cells. *Cell* 136, 411-419.
Koh, KP, et al. (2011) Tet1 and Tet2 regulate 5-hydroxymethylcytosine production and cell lineage specification in mouse embryonic stem cells. *Cell Stem Cell* 8, 200-213.
Li, H, et al. (2009) The Ink4/Arf locus is a barrier for iPS cell reprogramming. *Nature* 460, 1136-1139.
Li, W. et al. (2013) Chemical Approaches to Stem Cell Biology and Therapeutics. *Cell Stem Cell*. 13(3):270-283.
Li, W, et al. (2009) Generation of human-induced pluripotent stem cells in the absence of exogenous Sox2. *Stem Cells* 27, 2992-3000.
Li, Y, et al. (2010) Generation of iPSCs from mouse fibroblasts with a single gene, Oct4, and small molecules. *Cell Research* 21, 196-204.
Liao, B, et al. (2011) MicroRNA cluster 302-367 enhances somatic cell reprogramming by accelerating a mesenchymal-to-epithelial transition. *JBC* 286, 17359-17364.
Lin, T, et al. (2009) A chemical platform for improved induction of human iPSCs, *Nature Methods* 6, 805-808.
Lin, C. et al. (2013) Toward directed reprogramming through exogenous factors. *Current Opinion in Genetic & Development*, 23(5):519-525.
Loewer, S, et al. (2010) Large intergenic non-coding RNA-RoR modulates reprogramming of human induced pluripotent stem cells. *Nature Genetics* 42, 1113-1117.

(Continued)

*Primary Examiner* — Marcia S Noble
(74) *Attorney, Agent, or Firm* — Kilpatrick Townsend & Stockton LLP

(57) ABSTRACT

Described herein, inter alia, are methods and compositions useful for induced pluripotent stem cell reprogramming.

29 Claims, 13 Drawing Sheets

(56) References Cited

PUBLICATIONS

Lyssiotis, CA, et al. (2009) Reprogramming of murine fibroblasts to induced pluripotent stem cells with chemical complementation of Klf4. *PNAS* 106, 8912-8917.

Mali, P, et al. (2010) Butyrate greatly enhances derivation of human induced pluripotent stem cells by promoting epigenetic remodeling and the expression of pluripotency-associated genes. *Stem Cells* 28, 713-720.

Marion, RM, et al. (2009) A p53-mediated DNA damage response limits reprogramming to ensure iPS cell genomic integrity. *Nature* 460, 1149-1153.

Marson, A, et al. (2008) Wnt signaling promotes reprogramming of somatic cells to pluripotency. *Cell Stem Cell* 3, 132-135.

Masuda, S, et al. (2013) Chemically induced pluripotent stem cells (CIPSCs): a transgene-free approach. *Journal of Molecular Cell Biology Advance Access* published Sep. 6, 2013 [Downloaded from http://jmcb.oxfordjournals.org/ on Sep. 17, 2013] 11 pages.

Mitsui, K, et al. (2003) The homeoprotein Nanog is required for maintenance of pluripotency in mouse epiblast and ES cells. *Cell* 113, 631-642.

Miyoshi, N, et al. (2011) Reprogramming of mouse and human cells to pluripotency using mature microRNAs. *Cell Stem Cell* 8, 633-638.

Nichols, J, et al. (1998) Formation of pluripotent stem cells in the mammalian embryo depends on the POU transcription factor Oct4, *Cell* 95, 379-391.

Niwa, H, Miyazaki, J, & Smith, AG (2000) Quantitative expression of Oct-3/4 defines differentiation, dedifferentiation of self-renewal of ES cells. *Naure Genetics* 24, 372-376.

Sato, N, Meijer, L, Skaitsouris, L, Greengard, P, & Brivanlou, AH (2004) Maintenance of pluripotency in human and mouse embryonic stem cells through activation of Wnt signaling by a pharmacological GSK-3-specific inhibitor. *Nature Medicine* 10, 55-63.

Shi, Y, et al. (2008) A combined chemical and genetic approach for the generation of induced pluripotent stem cells. *Cell Stem Cell* 2, 525-528.

Shi, Y, et al. (2008) Induction of pluripotent stem cells from mouse embryonic fibroblasts by Oct4 and Klf4 with small-molecule compounds. *Cell Stem Cell* 3, 568-574.

Silva, J, et al. (2008) Promotion of reprogramming to ground state pluripotency by signal inhibition *PLoS Biology* 6, e253.

Silva, J, et al. (2009) Nanog is the gateway to the pluripotent ground state. *Cell* 138, 722-737.

Szabo, PE, Hubner, K, Scholer, H, & Mann, JR (2002) Allele-specific expression of imprinted genes in mouse migratory primordial germ cells. *Mech Dev* 115, 157-160.

Takahasi, K & Yamanaka, S (2006) Induction of pluripotent stem cells from mouse embryonic and adult fibroblast cultures by defined factors. *Cell* 126, 663-676.

Takahasi, K, et al. (2007) Induction of pluripotent stem cells from adult human fibroblasts by defined factors, *Cell* 131, 861-872.

Thompson, PA, et al. (2008) Identificaiton of ligand binding by protein stabilizaiton: comparison of ATLAS with biophysical and enzumatic methods. *ADDT* 6, 69-81.

Utikal, J, et al. (2009) Immortalization eliminates a roadblock during cellular reprogramming into iPS cells, *Nature* 460, 1145-1148.

Wang, Q, et al. (2011) Lithium, an anti-psychotic drug, greatly enhances the generation of induced pluripotent stem cells. *Cell Research* 21, 1424-1435.

Wang, W, et al. (2012) Rapid and efficient reprogramming of somatic cells to induced pluripotent stem cells by retinoic acid receptor gamma and liver receptor homolog 1. *PNAS* 108, 18283-18288.

Warren, L, et al. (2010) Highly efficient reprogramming to pluripotency and directed differentiation of human cells with synthetic modified mRNA. *Cell Stem Cell* 7, 618-630.

Yamanaka, S (2009) A Fresh Look at iPS Cells. *Cell* 137: 13-17.

Yamanaka, S (2007) Strategies and new developments in the generation of patient-specific pluripotent stem cells. *Cell Stem Cell* 1, 39-49.

Yoshida, Y, Takahashi, K, Okita, K, Ichisaka, T, & Yamanaka, S (2009) Hypoxia enhances the generation of induced pluripotent stem cells. *Cell Stem Cell* 5, 237-241.

Zhao, Y, et al. (2008) Two supporting factors greatly improve the efficiency of human iPSC generation. *Cell Stem Cell* 3, 475-479.

Zhu, S, et al. (2010) Reprogramming of human primary somatic cells by OCT4 and chemical compounds. *Cell Stem Cell* 7, 651-655.

SEQUENCE LISTING

```
<160> NUMBER OF SEQ ID NOS: 36

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95
```

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
            290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 2
<211> LENGTH: 190
<212> TYPE: PRT
<213> ORGANISM: Homo sapiens

<400> SEQUENCE: 2

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
            20                  25                  30

Leu Leu Gln Lys Trp Val Glu Glu Ala Asp Asn Asn Glu Asn Leu Gln
            35                  40                  45

Glu Ile Cys Lys Ala Glu Thr Leu Val Gln Ala Arg Lys Arg Lys Arg
        50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
            85                  90                  95

Leu Gly Leu Glu Lys Asp Val Val Arg Val Trp Phe Cys Asn Arg Arg

```
                    100                 105                 110
Gln Lys Gly Lys Arg Ser Ser Ser Asp Tyr Ala Gln Arg Glu Asp Phe
            115                 120                 125

Glu Ala Ala Gly Ser Pro Phe Ser Gly Gly Pro Val Ser Phe Pro Leu
130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
            180                 185                 190

<210> SEQ ID NO 3
<211> LENGTH: 190
<212> TYPE: PRT
<213> ORGANISM: Homo sapiens

<400> SEQUENCE: 3

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
            20                  25                  30

Leu Leu Gln Lys Trp Val Glu Ala Asp Asn Asn Glu Asn Leu Gln
        35                  40                      45

Glu Ile Cys Lys Ala Glu Thr Leu Val Gln Ala Arg Lys Arg Lys Arg
    50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
            100                 105                 110

Gln Lys Gly Lys Arg Ser Ser Ser Asp Tyr Ala Gln Arg Glu Asp Phe
        115                 120                 125

Glu Ala Ala Gly Ser Pro Phe Ser Gly Gly Pro Val Ser Phe Pro Leu
    130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
            180                 185                 190

<210> SEQ ID NO 4
<211> LENGTH: 317
<212> TYPE: PRT
<213> ORGANISM: Homo sapiens

<400> SEQUENCE: 4

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
```

```
                50              55              60
Lys Met His Asn Ser Glu Ile Ser Lys Arg Leu Gly Ala Glu Trp Lys
 65                  70                  75                  80

Leu Leu Ser Glu Thr Glu Lys Arg Pro Phe Ile Asp Glu Ala Lys Arg
                 85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 5
<211> LENGTH: 479
<212> TYPE: PRT
<213> ORGANISM: Homo sapiens

<400> SEQUENCE: 5

Met Arg Gln Pro Pro Gly Glu Ser Asp Met Ala Val Ser Asp Ala Leu
  1               5                  10                  15

Leu Pro Ser Phe Ser Thr Phe Ala Ser Gly Pro Ala Gly Arg Glu Lys
                 20                  25                  30

Thr Leu Arg Gln Ala Gly Ala Pro Asn Asn Arg Trp Arg Glu Glu Leu
             35                  40                  45

Ser His Met Lys Arg Leu Pro Pro Val Leu Pro Gly Arg Pro Tyr Asp
         50                  55                  60

Leu Ala Ala Ala Thr Val Ala Thr Asp Leu Glu Ser Gly Gly Ala Gly
 65                  70                  75                  80

Ala Ala Cys Gly Gly Ser Asn Leu Ala Pro Leu Pro Arg Arg Glu Thr
                 85                  90                  95

Glu Glu Phe Asn Asp Leu Leu Asp Leu Asp Phe Ile Leu Ser Asn Ser
                100                 105                 110
```

```
Leu Thr His Pro Pro Glu Ser Val Ala Ala Thr Val Ser Ser Ser Ala
            115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Leu Leu Tyr Gly Arg Glu
            165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
            195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
            245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
    275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
            325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
            405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
    435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 6
<211> LENGTH: 454
<212> TYPE: PRT
<213> ORGANISM: Homo sapiens

<400> SEQUENCE: 6

Met Asp Phe Phe Arg Val Val Glu Asn Gln Gln Pro Pro Ala Thr Met
1               5                   10                  15
```

```
Pro Leu Asn Val Ser Phe Thr Asn Arg Asn Tyr Asp Leu Asp Tyr Asp
            20                  25                  30
Ser Val Gln Pro Tyr Phe Tyr Cys Asp Glu Glu Asn Phe Tyr Gln
        35                  40                  45
Gln Gln Gln Gln Ser Glu Leu Gln Pro Pro Ala Pro Ser Glu Asp Ile
    50                  55                  60
Trp Lys Lys Phe Glu Leu Leu Pro Thr Pro Pro Leu Ser Pro Ser Arg
65                  70                  75                  80
Arg Ser Gly Leu Cys Ser Pro Ser Tyr Val Ala Val Thr Pro Phe Ser
                85                  90                  95
Leu Arg Gly Asp Asn Asp Gly Gly Gly Ser Phe Ser Thr Ala Asp
            100                 105                 110
Gln Leu Glu Met Val Thr Glu Leu Leu Gly Gly Asp Met Val Asn Gln
        115                 120                 125
Ser Phe Ile Cys Asp Pro Asp Asp Glu Thr Phe Ile Lys Asn Ile Ile
    130                 135                 140
Ile Gln Asp Cys Met Trp Ser Gly Phe Ser Ala Ala Lys Leu Val
145                 150                 155                 160
Ser Glu Lys Leu Ala Ser Tyr Gln Ala Ala Arg Lys Asp Ser Gly Ser
                165                 170                 175
Pro Asn Pro Ala Arg Gly His Ser Val Cys Ser Thr Ser Ser Leu Tyr
            180                 185                 190
Leu Gln Asp Leu Ser Ala Ala Ser Glu Cys Ile Asp Pro Ser Val
        195                 200                 205
Val Phe Pro Tyr Pro Leu Asn Asp Ser Ser Pro Lys Ser Cys Ala
    210                 215                 220
Ser Gln Asp Ser Ser Ala Phe Ser Pro Ser Ser Asp Ser Leu Leu Ser
225                 230                 235                 240
Ser Thr Glu Ser Ser Pro Gln Gly Ser Pro Glu Pro Leu Val Leu His
                245                 250                 255
Glu Glu Thr Pro Pro Thr Thr Ser Ser Asp Ser Glu Glu Glu Gln Glu
            260                 265                 270
Asp Glu Glu Glu Ile Asp Val Val Ser Val Glu Lys Arg Gln Ala Pro
        275                 280                 285
Gly Lys Arg Ser Glu Ser Gly Ser Pro Ser Ala Gly Gly His Ser Lys
    290                 295                 300
Pro Pro His Ser Pro Leu Val Leu Lys Arg Cys His Val Ser Thr His
305                 310                 315                 320
Gln His Asn Tyr Ala Ala Pro Pro Ser Thr Arg Lys Asp Tyr Pro Ala
                325                 330                 335
Ala Lys Arg Val Lys Leu Asp Ser Val Arg Val Leu Arg Gln Ile Ser
            340                 345                 350
Asn Asn Arg Lys Cys Thr Ser Pro Arg Ser Ser Asp Thr Glu Glu Asn
        355                 360                 365
Val Lys Arg Arg Thr His Asn Val Leu Glu Arg Gln Arg Arg Asn Glu
    370                 375                 380
Leu Lys Arg Ser Phe Phe Ala Leu Arg Asp Gln Ile Pro Glu Leu Glu
385                 390                 395                 400
Asn Asn Glu Lys Ala Pro Lys Val Val Ile Leu Lys Lys Ala Thr Ala
                405                 410                 415
Tyr Ile Leu Ser Val Gln Ala Glu Glu Gln Lys Leu Ile Ser Glu Glu
            420                 425                 430
```

```
Asp Leu Leu Arg Lys Arg Glu Gln Leu Lys His Lys Leu Glu Gln
            435                 440                 445

Leu Arg Asn Ser Cys Ala
        450

<210> SEQ ID NO 7
<211> LENGTH: 305
<212> TYPE: PRT
<213> ORGANISM: Homo sapiens

<400> SEQUENCE: 7

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Leu Glu Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 8
<211> LENGTH: 209
<212> TYPE: PRT
<213> ORGANISM: Homo sapiens
```

<400> SEQUENCE: 8

| | | | | | | | | | | | | | | | |
|---|---|---|---|---|---|---|---|---|---|---|---|---|---|---|---|
| Met | Gly | Ser | Val | Ser | Asn | Gln | Gln | Phe | Ala | Gly | Gly | Cys | Ala | Lys | Ala |
| 1 | | | | 5 | | | | | 10 | | | | | 15 | |
| Ala | Glu | Glu | Ala | Pro | Glu | Ala | Pro | Glu | Asp | Ala | Ala | Arg | Ala | Ala | |
| | | | 20 | | | | | 25 | | | | | 30 | | |
| Asp | Glu | Pro | Gln | Leu | Leu | His | Gly | Ala | Gly | Ile | Cys | Lys | Trp | Phe | Asn |
| | | 35 | | | | | 40 | | | | | 45 | | | |
| Val | Arg | Met | Gly | Phe | Gly | Phe | Leu | Ser | Met | Thr | Ala | Arg | Ala | Gly | Val |
| | 50 | | | | | 55 | | | | | 60 | | | | |
| Ala | Leu | Asp | Pro | Pro | Val | Asp | Val | Phe | Val | His | Gln | Ser | Lys | Leu | His |
| 65 | | | | | 70 | | | | | 75 | | | | | 80 |
| Met | Glu | Gly | Phe | Arg | Ser | Leu | Lys | Glu | Gly | Glu | Ala | Val | Glu | Phe | Thr |
| | | | | 85 | | | | | 90 | | | | | 95 | |
| Phe | Lys | Lys | Ser | Ala | Lys | Gly | Leu | Glu | Ser | Ile | Arg | Val | Thr | Gly | Pro |
| | | | 100 | | | | | 105 | | | | | 110 | | |
| Gly | Gly | Val | Phe | Cys | Ile | Gly | Ser | Glu | Arg | Arg | Pro | Lys | Gly | Lys | Ser |
| | | | 115 | | | | | 120 | | | | | 125 | | |
| Met | Gln | Lys | Arg | Arg | Ser | Lys | Gly | Asp | Arg | Cys | Tyr | Asn | Cys | Gly | Gly |
| | 130 | | | | | 135 | | | | | 140 | | | | |
| Leu | Asp | His | His | Ala | Lys | Glu | Cys | Lys | Leu | Pro | Pro | Gln | Pro | Lys | Lys |
| 145 | | | | | 150 | | | | | 155 | | | | | 160 |
| Cys | His | Phe | Cys | Gln | Ser | Ile | Ser | His | Met | Val | Ala | Ser | Cys | Pro | Leu |
| | | | | 165 | | | | | 170 | | | | | 175 | |
| Lys | Ala | Gln | Gln | Gly | Pro | Ser | Ala | Gln | Gly | Lys | Pro | Thr | Tyr | Phe | Arg |
| | | | 180 | | | | | 185 | | | | | 190 | | |
| Glu | Glu | Glu | Glu | Glu | Ile | His | Ser | Pro | Thr | Leu | Leu | Pro | Glu | Ala | Gln |
| | | | 195 | | | | | 200 | | | | | 205 | | |
| Asn | | | | | | | | | | | | | | | |

<210> SEQ ID NO 9
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 9
gtgcagagaa gtctacattc ccatgt                                  26

<210> SEQ ID NO 10
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 10
cgagaaggca aaatctgaag ccagg                                   25

<210> SEQ ID NO 11
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 11
agacacccac caccatgcgt ggct                                    24

<210> SEQ ID NO 12
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 12
tcctggagtc tctagatt                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
gctcagtgat gctgttgatc                                               20

<210> SEQ ID NO 14
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 14
cggcttcggc cagtaac                                                  17

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
actgcacatg gcccagcact a                                             21

<210> SEQ ID NO 16
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 16
cggcttcggc cagtaac                                                  17

<210> SEQ ID NO 17
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 17
cggaccacct tgccttacac a                                             21

<210> SEQ ID NO 18
<211> LENGTH: 17
<212> TYPE: DNA
<213> ORGANISM: Artificial Sequence
<220> FEATURE:

<223> OTHER INFORMATION: Synthetic polynucleotide

<400> SEQUENCE: 18
cggcttcggc cagtaac                                                    17

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19
cgagcacaag ctcacctctg a                                               21

<210> SEQ ID NO 20
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 20
cggcttcggc cagtaac                                                    17

<210> SEQ ID NO 21
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
gcatactgtg gacctcaggt t                                               21

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
tcgaagcgac agatggtggt                                                 20

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
ctgacatgag tgtgggtctt c                                               21

<210> SEQ ID NO 24
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 24
gaatggagga gagttcttgc a                                               21

```
<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
tgcacaactc ggagatcagc a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 26
ctcctgcatc atgctgtagc t                                              21

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
tctgggacag ccaagtctgt                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
ggagtcttcc agtgtgatga                                                20

<210> SEQ ID NO 29
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 29
cgcacaggag caaagtgtgc cgt                                            23

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30
tgccctccag cggcgtctcc gtg                                            23

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 31
gagcctgttc ctcgatgtgg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
caaacccacc tgaggctgtt                                               20

<210> SEQ ID NO 33
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 33
aacctggcta ctgtcattgc tcca                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 34
atgttctgct ggtctctgtg ggaa                                          24

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
ccgagcgtgg ctacagcttc                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
acctggccgt caggcagctc                                               20
```

ENHANCERS OF INDUCED PLURIPOTENT STEM CELL REPROGRAMMING

CROSS-REFERENCES TO RELATED APPLICATIONS

This application claims the benefit of U.S. Provisional Patent Application No. 61/732,875, filed Dec. 3, 2012, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant NIH NINDS RC1 NS068370 awarded by the National Institute of Health. The Government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 95058-882785_ST25.TXT, created on Aug. 30, 2013, 27,699 bytes, machine format IBM-PC, MS-Windows operating system, is hereby incorporated by reference in its entirety for all purposes.

BACKGROUND

Recent breakthroughs in the development of induced pluripotent stem cells have generated much interest in the therapeutic potential of stem cells in regenerative medicine. Pioneering work by Yamanaka and colleagues identified a transcription factor quartet (4F), Oct4, Sox2, Klf4 and c-Myc, that enables reprogramming of somatic cells to a pluripotent state (1, 2). The induced pluripotent stem cells (iPSCs) closely resemble embryonic stem cells (ESCs) in gene expression, epigenetic signature, and functional pluripotency. The simplicity of this reprogramming approach has opened up tremendous opportunities to generate patient-specific cells for disease modeling and therapeutic applications.

Two issues appear to limit the application of iPSCs, the low efficiency of reprogramming and the integration of transgenes into the somatic genome (3). The low efficiency and slow kinetics of reprogramming methods to generate iPSCs impose major limitations on their biomedical applications and continue to present a problem for ultimate therapeutic applications of iPSCs. There is thus a need for more efficient procedures for iPSC generation, and one approach is the use of small molecule chemicals to reprogram somatic cells with improved efficiency and kinetics.

Substantial effort has been made toward identifying chemical compounds that can enhance the efficiency of reprogramming (4-14). Several small molecules that are known to remodel chromatin and affect epigenetic control are being investigated actively for their effect on reprogramming. It has been shown that DNA methyltransferase inhibitors, histone deacetylase (HDAC) inhibitors, and histone demethylase inhibitors can improve reprogramming efficiency (4, 5, 10, 11, 13). These compounds may act by reducing the epigenetic barriers to reprogramming, and they may potentially improve the efficiency and quality of the derived iPSCs (13). Molecules that act on known signaling pathways involved in ESC self-renewal and pluripotency, including Wnt, TGFβ, and MEK, have also been shown to enhance reprogramming efficiency (8, 9, 11, 15). More recently, retinoic acid receptor (RAR) agonists, vitamin C and lithium have been reported to enhance reprogramming efficiency as well (12, 16, 17).

Oct4 is a key regulator for ESC pluripotency. Reduced expression of Oct4 results in differentiation of ESCs into trophectodermal cells, while ovexpression of Oct4 leads to differentiation of ESCs along the mesodermal and primitive endodermal lineages (18). Since the original report of induced reprogramming using the transcription factor quartet, Oct4, Sox2, Klf4, and c-Myc, the combination of factors used to generate iPSCs have been much studied (4-13, 15, 16, 19-32). However, Oct4 remains as the key, required component of the reprogramming cocktail, not replaceable by other factors, except the nuclear receptors NR5a1, NR5a2, and the combination of microRNAs miR-200c, miR-302s and miR-369s (23, 33, 34). Using neural stem cells that endogenously express Sox2, Klf4, and c-Myc, Oct4 was shown to be sufficient by itself to induce pluripotency (35, 36). The central role of Oct4 in the reprogramming process prompted us to ask whether Oct4-activating compounds may enhance reprogramming efficiency, thus improving iPSC technology.

In this study, high-throughput screening of small molecule libraries was performed to identify Oct4 promoter-activating compounds using a human Oct4 promoter-driven luciferase reporter. The identified compounds were characterized for their ability to enhance reprogramming efficiency and accelerate the reprogramming process. The derived iPSCs were characterized for their gene expression, epigenetic profile, and pluripotency. Disclosed herein, inter alia, are solutions to these and other problems in the art.

BRIEF SUMMARY

In a first aspect, a method of expressing an Oct4 protein in a cell is provided. The method includes contacting a cell with a compound having the formula:

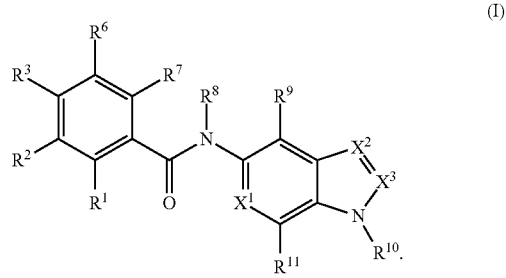

(I)

$X^1$ is $C(R^{12})$ or N. $X^2$ is $C(R^4)$ or N. $X^3$ is $C(R^5)$ or N. $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ and $R^3$ are optionally joined to form a substituted or unsubstituted heterocycloalkyl or substituted or unsubstituted heteroaryl. The method further includes, after the contacting step, allowing the cell to express an Oct4 protein.

In another aspect, a method of expressing a Nanog protein in a cell is provided. The method includes contacting a cell with a compound of Formula (I). The method further includes, after the contacting step, allowing the cell to express a Nanog protein.

In another aspect, a method of making (e.g. forming) an induced pluripotent stem cell is provided. The method includes contacting a non-pluripotent cell with a compound of Formula (I). The method further includes, after the contacting step, allowing said non-pluripotent cell to divide thereby forming said induced pluripotent stem cell.

In an aspect is provided a compound of Formula (I), or a pharmaceutically acceptable salt thereof, as described herein (including embodiments) (e.g. a compound of formula (I), (II), (IIa), (III), (IV), (IVa), (V), or any embodiments thereof; a compound described in an aspect, embodiment, method, figure, table, example, or claim).

In an aspect is provided a composition including a compound of Formula (I) as described herein, (including embodiments) (e.g. a compound of formula (I), (II), (IIa), (III), (IV), (IVa), (V), or any embodiments thereof; a compound described in an aspect, embodiment, method, figure, table, example, or claim).

In another aspect, a cell is provided. The cell includes a compound of Formula (I).

In another aspect, a mixture is provided. The mixture includes a cell and a compound of Formula (I).

In another aspect a kit is provided. The kit includes a recombinant Oct4 protein, a recombinant Nanog protein, a recombinant Sox2 protein, a recombinant Lin28 protein, a recombinant Klf4 protein, a recombinant cMyc protein, a Sox2 expression inducer, a Lin28 expression inducer, a Klf4 expression inducer, a cMyc expression inducer, a nucleic acid encoding an Oct4 protein (e.g. Oct4 synthetic or recombinant mRNA), a nucleic acid encoding a Nanog protein (e.g. Nanog synthetic or recombinant mRNA), a nucleic acid encoding a Sox2 protein (e.g. Sox2 synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), or a nucleic acid encoding a cMyc protein (e.g. cMyc synthetic or recombinant mRNA). The kit also includes a compound of Formula (I).

A. Bisulfite genomic sequencing of the promoter regions of OCT4 in human IMR90 fibroblasts treated with or without OAC1 for two days. Open and closed circles indicate unmethylated and methylated CpGs, respectively. B. RT-PCR analyses of p53 and p21 expression in vehicle or OAC 1-treated cells. MEFs were treated with OAC1 for two days and RNAs were prepared from treated cells for RT-PCR analysis. C. Topflash luciferase reporter assays in CV1 cells treated with vehicle (C), 1 µM OAC1 or 2 µM BIO. D, E. OAC 1 activated Oct4 and Nanog promoter-driven luciferase reporter genes. Oct4-luc (D) or Nanog-luc (E) stably transfected cells were treated with OAC1 (1 µM), BIO (2 µM), BIX (2 µM), AzaC (2 µM), Vc (25 µg/ml), Am580 (10 nM), Tranylcypromine (Tranyl, 5 µM), and VPA (0.5 mM) for two days. F, G. Dose responsive of OAC1 in Oc4-luc or Nanog-luc stably transfected cells. Oct4-luc (F) or Nanog-luc (G) transfected cells were treated with OAC1 at concentrations of 50 nM, 100 nM, 250 nM, 500 nM and 1 uM for 2 to 7 days. H. A diagram showing the Oct4, Sox2 and Nanog triad, forming a regulatory feedback circuit. I. OAC1 activated endogenous Oct4, Sox2 and Nanog genes in MEFs as revealed by RT-PCR analysis. J. OAC1 activated Tet1 expression in MEFs as revealed by RT-PCR analysis. Actin was included as a loading control.

Figure 7:
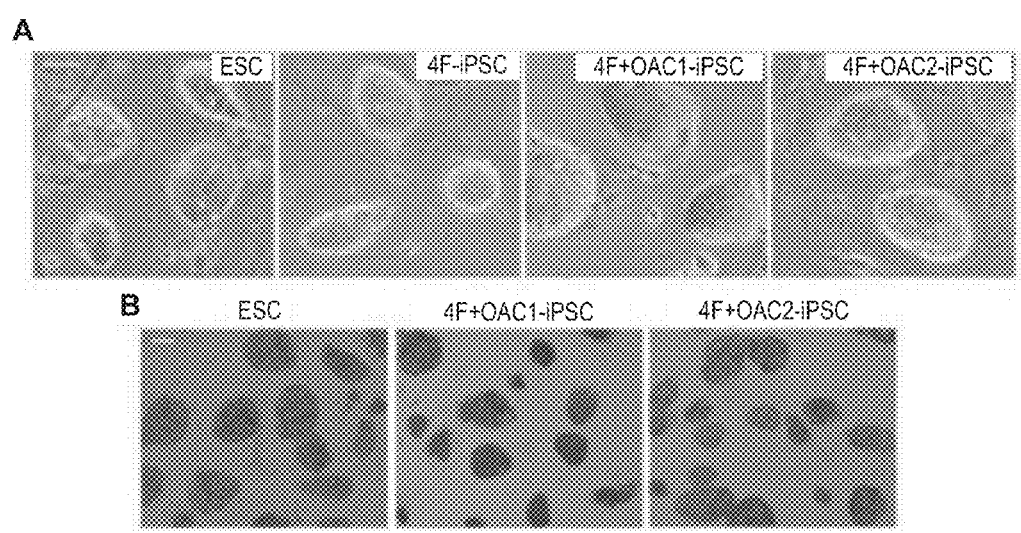

FIG. 7. Characterization of 4F+OAC1 and 4F+OAC2-iP-SCs. A. The morphology of mouse ESCs, 4F, 4F+OAC1 and 4F+OAC2-iPSCs. Scale bar, 50 µm. B. AP staining of mouse ESCs, 4F+OAC1 and 4F+OAC2-iPSCs. Scale bar, 100 µm.

Figure 8:
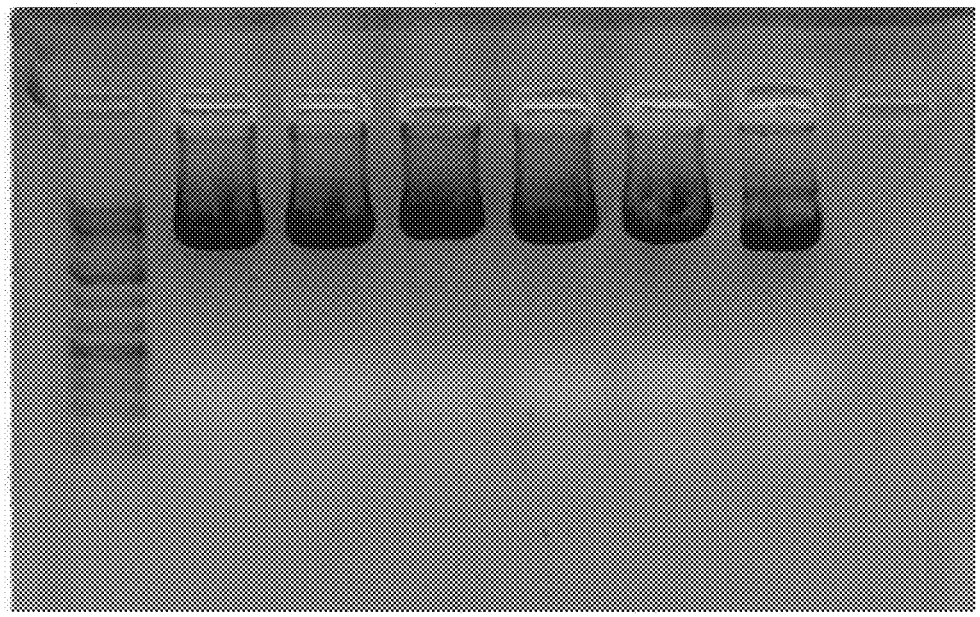

FIG. 8: TF DNA. Transcription Factor DNA (Oct-4, Sox-2, Klf-4, c-Myc) and viral packaging components (VSVG, CMVGP) were extracted from plasmid transformed *E. Coli*. A DNA gel was run to ensure quality of DNA.

Figure 9:
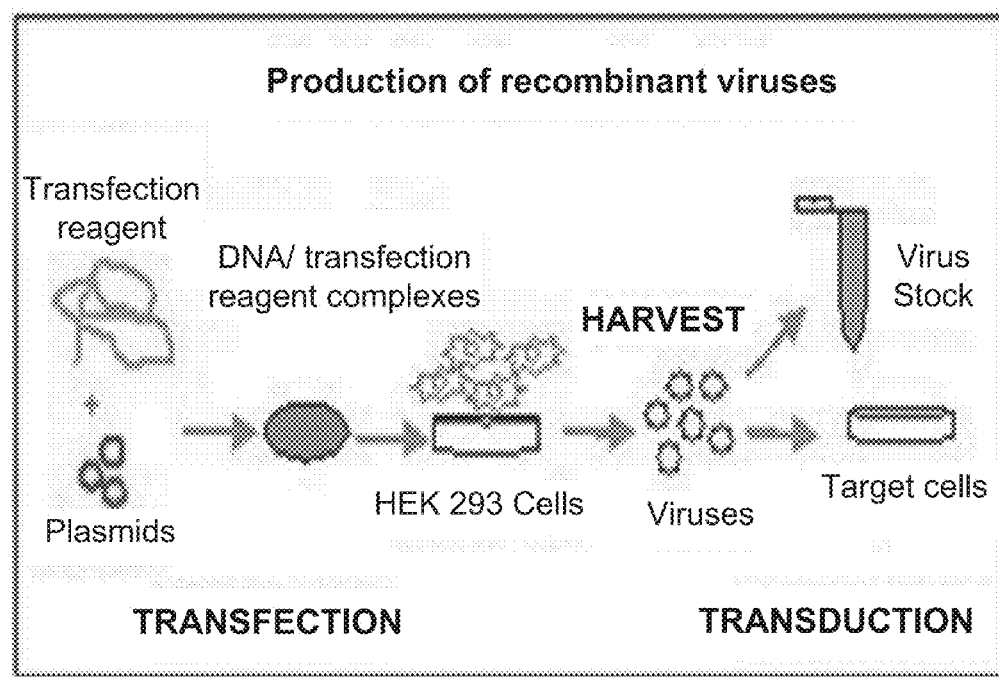
Figure 10:

FIG. 9: Using transfection reagents the 293T cells produced virus which packages the plasmids that contain the TF DNA. http://stemcells.nih.gov/info/Regenerative_Medicine/2006chapter10.htm FIG. 10: Retroviral Mediated Reprogramming. Virus was generated that included all the four factors to reprogram to iPS. What is shown here is a technical control of retroviral mediated induction of GFP which serves as a technical control for retroviral transduction.

Figure 11:
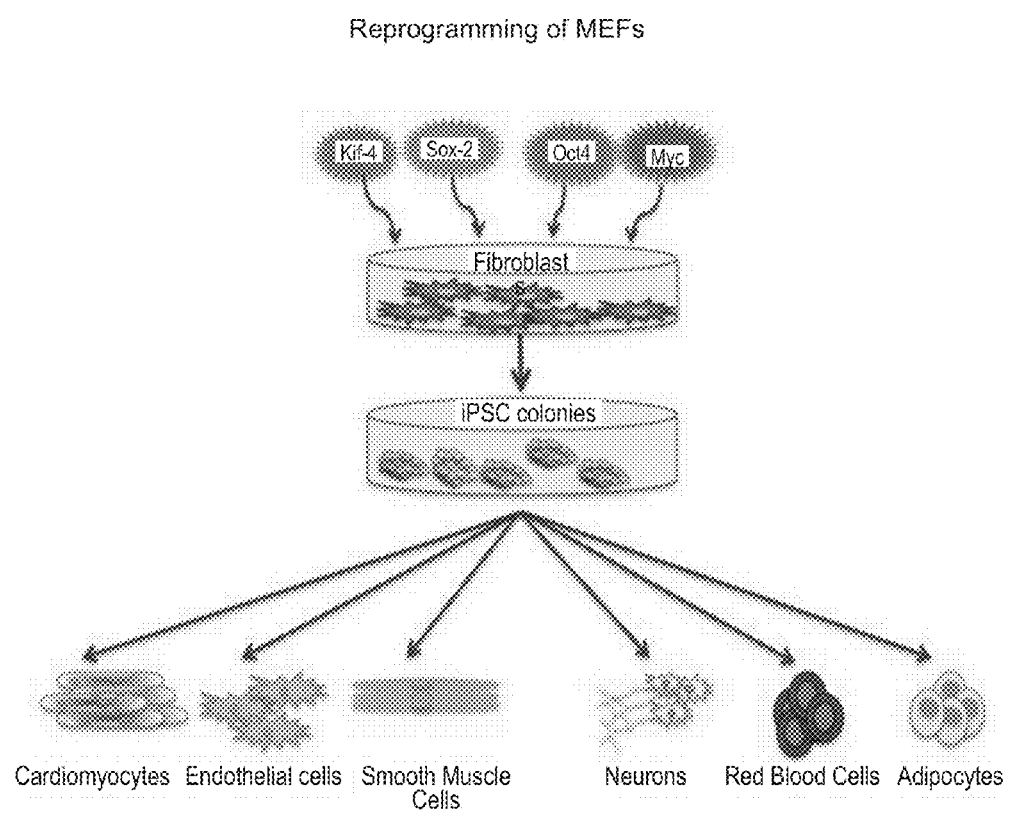
Figure 12:
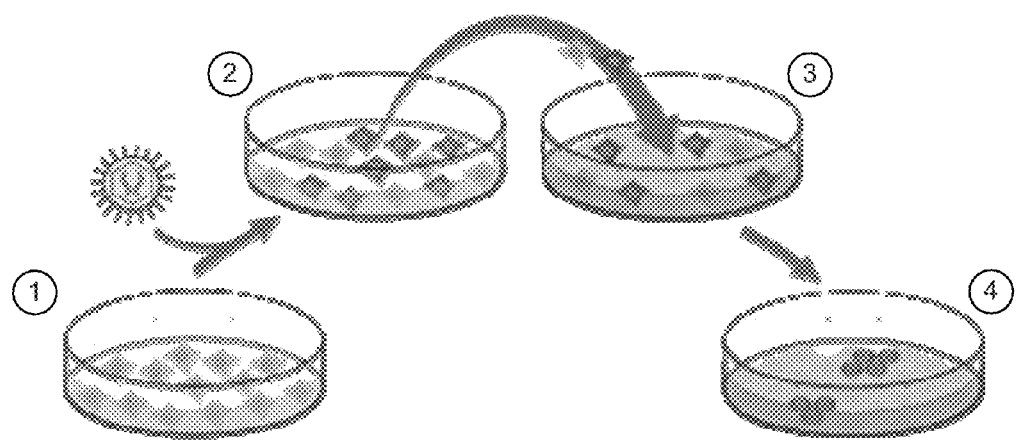
Figure 13:
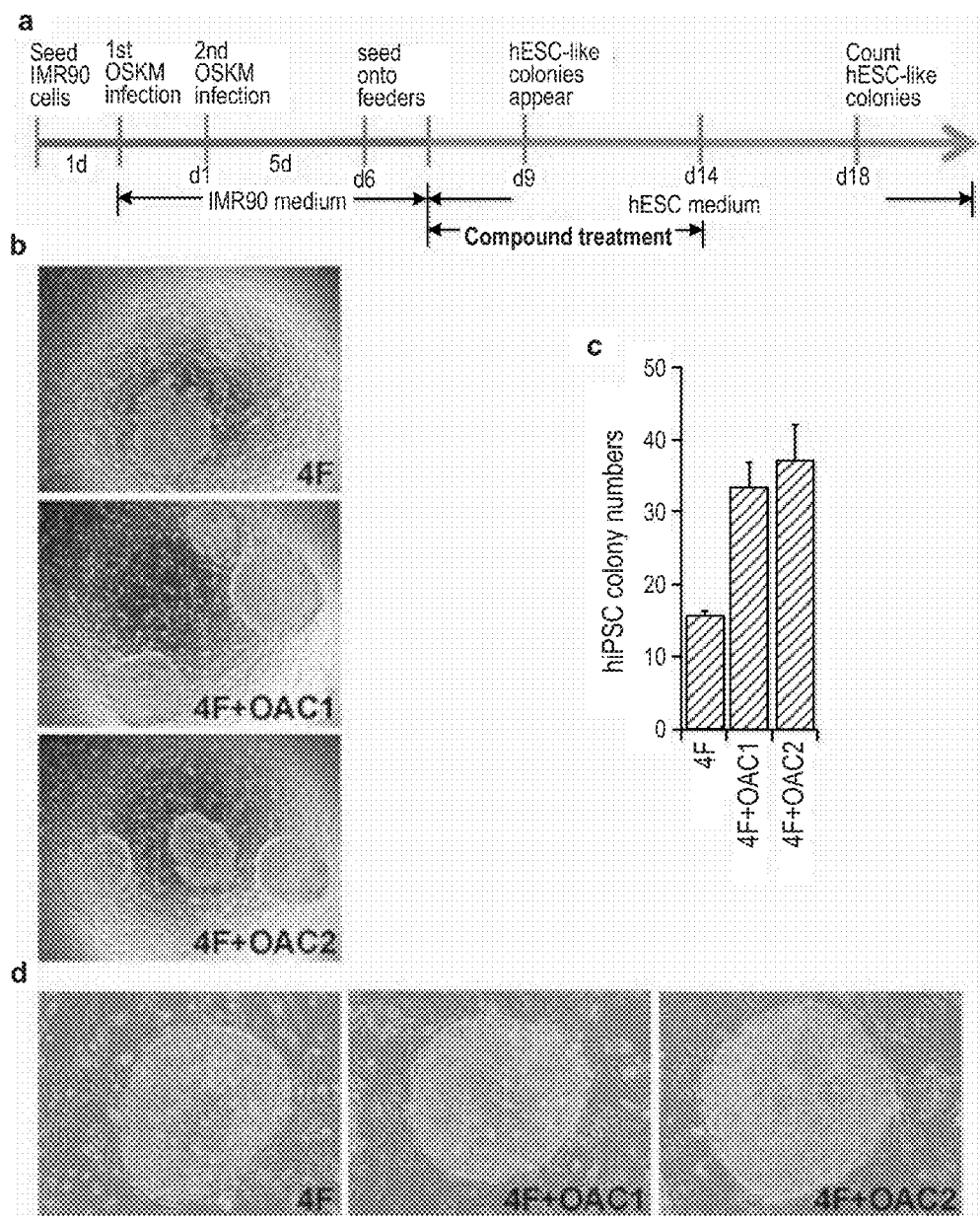

FIG. 11: The original transcription factors Oct-4, Sox-2, Klf-4, c-Myc are inserted into fibroblasts to transform them to a pluripotent state (IPSC). After which the cells can be induced to become a multitude of cell lineages. http://www.sciencedirect.com/science/article/pii/S0169409X1100041X FIG. 12: 1) OG2-MEF's are cultured to 90% confluency. 2) Virus containing the TF DNA are exogenously inserted into the MEFs. 3) Small molecules were added to the reprogramming media. 4) A small subset of transfected cells become iPSCs and generate ES-like colonies. http://en.wikipedia.org/wiki/Induced_pluripotent_stem_cell FIG. 13: Compound OAC1 and OAC2 enhance reprogramming efficiency in human cells. A. Schematic representation of iPSC generation from human IMR90 fibroblast cells using four factors, Oct4, Sox2, Klf4, and c-Myc (OSKM)+OAC compounds. B. Images of human iPSC clones from reprogramming using 4F, 4F+OAC1 and 4F+OAC2. C. Quantification of human iPSC colony numbers in 4F, 4F+OAC1, and 4F+OAC2 reprogramming. D. The iPSC colonies from 4F, 4F+OAC1, and 4F+OAC2 reprogramming exhibited typical human ESC-like morphology.

DETAILED DESCRIPTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N(CH_3)—$CH_3$, —$CH_2$—S—$CH_2$—$CH_3$, —$CH_2$—$CH_2$, —S(O)—$CH_3$, —$CH_2$—$CH_2$—S(O)_2—$CH_3$, —CH=CH—O—$CH_3$, —Si(CH_3)_3, —$CH_2$—CH=N—$OCH_3$, —CH=CH—N(CH_3)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si(CH_3)_3.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)_2R'— represents both —C(O)_2R'— and —R'C(O)_2—. As described above, heteroalkyl groups, as used herein, include those groups that are attached to the remainder of the molecule through a heteroatom, such as —C(O)R', —C(O)NR', —NR'R", —OR', —SR', and/or —SO_2R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O⁻ bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —O C(O)NR'R", —NR"C(O)R', —NR'—C(O)NR"R'", —NR"C(O)$_2$R', —NR—C(NR'R"R'")=NR"", —N R—C(NR'R")=NR'", —S(O)R', —S(O)$_2$R', —S(O)$_2$NR'R", —NR$SO_2$R', —NR'NR"R'", —ONR'R", —NR'C=(O)NR"NR'"R"", —CN, —$NO_2$, —NR'$SO_2$R", —NR'C=(O)R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups.

When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR' R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "$\sim\!\sim\!\sim$" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$, $R^{14}$, and/or $R^{15}$ substituents are present, each $R^{13}$, $R^{14}$, and/or $R^{15}$ substituent may be distinguished as $R^{13A}$, $R^{13B}$, $R^{13C}$, $R^{13D}$, $R^{13E}$, $R^{13F}$, $R^{13G}$, $R^{13H}$, $R^{13I}$, $R^{13J}$, $R^{13K}$, $R^{13L}$, etc.; $R^{14A}$, $R^{14B}$, $R^{14C}$, $R^{14D}$, $R^{14E}$, $R^{14F}$, $R^{14G}$, $R^{14H}$, $R^{14I}$, $R^{14J}$, $R^{14K}$, $R^{14L}$, etc.; and $R^{15A}$, $R^{15B}$, $R^{15c}$, $R^{15D}$, $R^{15E}$, $R^{15F}$, $R^{15G}$, $R^{15H}$, $R^{15I}$, $R^{15J}$, $R^{15K}$, $R^{15L}$, etc. respectively. Each of $R^{13A}$, $R^{13B}$, $R^{13C}$, $R^{13D}$, $R^{13E}$, $R^{13F}$, $R^{13G}$, $R^{13H}$, $R^{13I}$, $R^{13J}$, $R^{13K}$, $R^{13L}$, etc. is defined within the scope of the definition of $R^{13}$ and optionally differently. Each of $R^{14A}$, $R^{14B}$, $R^{14C}$, $R^{14D}$, $R^{14E}$, $R^{14F}$, $R^{14G}$, $R^{14H}$, $R^{14I}$, $R^{14J}$, $R^{14K}$, $R^{14L}$, etc. is defined within the scope of the definition of $R^{14}$ and optionally differently. Each of $R^{15A}$, $R^{15B}$, $R^{15C}$, $R^{15D}$, $R^{15E}$, $R^{15F}$, $R^{15G}$, $R^{15H}$, $R^{15I}$, $R^{15J}$, $R^{15K}$, $R^{15L}$, etc. is defined within the scope of the definition of $R^{15}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "recombinant" when used with reference, e.g., to a cell, virus, nucleic acid, protein, or vector, indicates that the cell, virus, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. For example, a recombinant protein may be a protein that is expressed by a cell or organism that has been modified by the introduction of a heterologous nucleic acid (e.g. encoding the recombinant protein).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and/or the translation of a gene. Further, a "protein gene product" is a protein expressed from a particular gene.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected.

Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1X SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88). Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into the host genome. During transposon-mediated insertion the gene is positioned between two transposon linker sequences that allow insertion into the host genome as well as subsequent excision.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

A "vector" is a nucleic acid that is capable of transporting another nucleic acid into a cell. A vector is capable of directing expression of a protein or proteins encoded by one or more genes carried by the vector when it is present in the appropriate environment.

A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

A "cell culture" is a population of cells residing outside of an organism. These cells are optionally primary cells isolated from a cell bank, animal, or blood bank, or secondary cells that are derived from one of these sources and have been immortalized for long-lived in vitro cultures.

The terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division. The term does not imply that all cells in the culture survive or grow or divide, as some may naturally senesce, etc. Cells are typically cultured in media, which can be changed during the course of the culture.

The terms "media" and "culture solution" refer to the cell culture milieu. Media is typically an isotonic solution, and can be liquid, gelatinous, or semi-solid, e.g., to provide a matrix for cell adhesion or support. Media, as used herein, can include the components for nutritional, chemical, and structural support necessary for culturing a cell.

The term "derived from," when referring to cells or a biological sample, indicates that the cell or sample was obtained from the stated source at some point in time. For example, a cell derived from an individual can represent a primary cell obtained directly from the individual (i.e., unmodified), or can be modified, e.g., by introduction of a recombinant vector, by culturing under particular conditions, or immortalization. In some cases, a cell derived from a given source will undergo cell division and/or differentiation such that the original cell is no longer exists, but the continuing cells will be understood to derive from the same source.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

The term "Yamanaka factors" refers to Oct3/4, Sox2, Klf4, and c-Myc, which factors are highly expressed in embryonic stem (ES) cells. Yamanaka factors can induce pluripotency in somatic cells from a variety of species, e.g., mouse and human somatic cells. See e.g., Yamanaka, 2009, Cell 137: 13-17.

An "OCT4 protein" or "Oct4 protein" as referred to herein includes any recombinant or naturally-occurring form of the Octomer 4 transcription factor, or variants thereof that maintain Oct4 transcription factor activity (e.g. within at least 50%, 80%, 90%, 95%, 96%, 97%, 98%, 99% or 100% activity compared to Oct4). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Oct4 polypeptide (e.g. NCBI reference gi:42560248 [SEQ ID NO:1] corresponding to isoform 1, and gi:116235491 [SEQ ID NO:2] and gi:291167755 [SEQ ID NO:3] corresponding to isoform 2).

An "Oct 4 RNA" or "OCT4 RNA" as used herein refers to an RNA encoding an OCT4 protein. In some embodiments, the Oct4 RNA is an Oct4 mRNA. In some embodiments the RNA is a synthetic or recombinant Oct4 mRNA.

A "Sox2 protein" or "SOX2 protein" as referred to herein includes any recombinant or naturally-occurring form of the Sox2 transcription factor, or variants thereof that maintain Sox2 transcription factor activity (e.g. within at least 50%, 80%, 90%, 95%, 96%, 97%, 98%, 99% or 100% activity compared to Sox2). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Sox2 polypeptide (e.g. the protein as identified by the NCBI reference gi:28195386 [SEQ ID NO:4]).

A "Sox2 RNA" or "SOX2 RNA" as used herein refers to an RNA encoding a Sox2 protein. In some embodiments, the Sox2 RNA is a Sox2 mRNA. In some embodiments the RNA is a synthetic or recombinant Sox2 mRNA.

A "KLF4 protein" or "Klf4 protein" as referred to herein includes any recombinant or naturally-occurring form of the KLF4 transcription factor, or variants thereof that maintain KLF4 transcription factor activity (e.g. within at least 50%, 80%, 90%, 95%, 96%, 97%, 98%, 99% or 100% activity compared to KLF4). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring KLF4 polypeptide (e.g. the protein as identified by the NCBI reference gi:194248077 [SEQ ID NO:5]).

A "KLF4 RNA" or "Klf4 RNA" as used herein refers to an RNA encoding a KLF4 protein. In some embodiments, the KLF4 RNA is a KLF4 mRNA. In some embodiments the RNA is a synthetic or recombinant KLF4 mRNA.

A "cMYC protein" or "CMYC protein" or "c-Myc protein" as referred to herein includes any recombinant or naturally-occurring form of the cMyc transcription factor, or variants thereof that maintain cMyc transcription factor activity (e.g. within at least 50%, 80%, 90%, 95%, 96%, 97%, 98%, 99% or 100% activity compared to cMyc). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring cMyc polypeptide (e.g. the protein as identified by the NCBI reference gi:71774083 [SEQ ID NO:6]).

A "cMYC RNA" or "CMYC RNA" or "c-Myc RNA" as used herein refers to an RNA encoding a cMyc protein. In some embodiments, the cMyc RNA is a cMyc mRNA. In some embodiments the RNA is a synthetic or recombinant cMyc mRNA.

A "NANOG protein" or "Nanog protein" as referred to herein includes any recombinant or naturally-occurring forms of the Nanog transcription factor, or variants thereof that maintain Nanog transcription factor activity (e.g. within at least 50%, 80%, 90%, 95%, 96%, 97%, 98%, 99% or 100% activity compared to Nanog). In some embodiments, variants have at least 90%, 95%, 96%, 97%, 98%, 99% or 100% amino acid sequence identity across their whole sequence (e.g. a 50, 100, 150 or 200 continuous amino acid portion) compared to the naturally occurring Nanog polypeptide (e.g. the protein as identified by the NCBI reference gi:153945816 [SEQ ID NO:7]).

A "NANOG RNA" or "Nanog RNA" as used herein refers to an RNA encoding a Nanog protein. In some embodiments, the Nanog RNA is a Nanog mRNA. In some embodiments the RNA is a synthetic or recombinant Nanog mRNA.

A "LIN28 protein" or "Lin28 protein" as referred to herein includes any recombinant or naturally-occurring form of the Lin28 transcription factor, or variants thereof that maintain Lin28 transcription factor activity (e.g. within at least 50%, 80%, 90% or 100% activity compared to Lin28). In some embodiments, variants have at least 90% amino acid sequence identity across their whole sequence compared to the naturally occurring Lin28 polypeptide (e.g. the protein as identified by the NCBI reference gi:13375938 [SEQ ID NO:8]).

A "Lin28 RNA" or "LIN28 RNA" as used herein refers to an RNA encoding a Lin28 protein. In some embodiments, the Lin28 RNA is a Lin28 mRNA. In some embodiments the RNA is a synthetic or recombinant Lin28 mRNA.

An "inducer" as used herein refers to any agent that alters the expression of a protein or RNA (e.g. mRNA). Inducers may be, for example, small molecules, proteins/polypeptides, or nucleic acids, and include but are not limited to BIX, BayK, CHIR99021 (GSK3β inhibitor), Parnate (tranylcypromine, monoamine oxidase inhibitor), E-616452 (RepSox, Alk5 inhibitor); Dasatinib (Src inhibitor), iPY (iPyrazine, Src inhibitor), PP1 (Src inhibitor), LY-364947 (TGF β inhibitor), n-butylidenephthalide (BP, Jak2/Stat3 activator), valproic acid VPA (histone deacetylase inhibitor), AzaC (5'-azacytidine, DNA methylransferase inhibitor), kenpaullone (inhibitor of CDK and GSK), 5-aminoimidazole-4-carboxamide-1-b-riboside (AICAR, AMPK activator), AMI-5 (protein methyltransferase inhibitor), A-83-01 (TGFβ receptor inhibitor), sodium butyrate (NaB, histone deacetylase inhibitor), PS48 (PDK1 activator), PD0325901 (MEK inhibitor), SB-431542 (TGFβ receptor inhibitor), or leukaemia inhibitor factor (LIF). In embodiments, inducers (e.g. Oct4 expression inducer, Sox2 expression inducer, Klf4 expression inducer, cMyc expression inducer, Lin28 expression inducer, or Nanog expression inducer) are compositions (i.e. agents) that alter (e.g. increase) the expression of a nucleic acid (e.g. mRNA) encoding a protein (e.g. Oct4, Sox2, Klf4, cMyc, Lin28, or Nanog) or the expression of a protein (e.g. Oct4, Sox2, Klf4, cMyc, Lin28, or Nanog) but are not themselves a nucleic acid encoding the protein or the protein having the altered expression.

A "somatic cell" is a cell forming the body of an organism. Somatic cells include cells making up organs, skin, blood, bones and connective tissue in an organism, but not germline cells.

A "stem cell" is a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

"Self renewal" refers to the ability of a cell to divide and generate at least one daughter cell with the self-renewing characteristics of the parent cell. The second daughter cell may commit to a particular differentiation pathway. For example, a self-renewing hematopoietic stem cell can divide and form one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype. Non-self renewing cells refer to cells that undergo cell division to produce daughter cells, neither of which have the differentiation potential of the parent cell type, but instead generate differentiated daughter cells.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old immunodeficient mice (e.g. SCID) mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

An "induced pluripotent stem cell" refers to a pluripotent stem cell artificially (e.g. non-naturally, in a laboratory setting) derived from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells. An adult stem cell is an undifferentiated cell found throughout the body after embryonic development. Adult stem cells multiply by cell division to replenish dying cells and regenerate damaged tissue. Adult stem cells have the ability to divide and create another like cell and also divide and create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers. Adult stem cells have a limited potency to self renew and generate progeny of distinct cell types. Without limitation, an adult stem cell can be a hematopoietic stem cell, a cord blood stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

The term "reprogramming" refers to the process of dedifferentiating a non-pluripotent cell (e.g., an origin cell) into a cell exhibiting pluripotent stem cell characteristics (e.g., a human induced pluripotent stem cell).

Where appropriate the expanding transfected derived stem cell may be subjected to a process of selection. A process of selection may include a selection marker introduced into an induced pluripotent stem cell upon transfection. A selection marker may be a gene encoding for a polypeptide with enzymatic activity. The enzymatic activity includes, but is not limited to, the activity of an acetyltransferase or a phosphotransferase. In some embodiments, the enzymatic activity of the selection marker is the activity of a phosphotransferase. The enzymatic activity of a selection marker may confer to a transfected induced pluripotent stem cell the ability to expand in the presence of a toxin. Such a toxin typically inhibits cell expansion and/or causes cell death. Examples of such toxins include, but are not limited to, hygromycin, neomycin, puromycin and gentamycin. In some embodiments, the toxin is hygromycin. Through the enzymatic activity of a selection maker a toxin may be converted to a non-toxin, which no longer inhibits expansion and causes cell death of a transfected induced pluripotent stem cell. Upon exposure to a toxin a cell lacking a selection marker may be eliminated and thereby precluded from expansion.

Identification of the induced pluripotent stem cell may include, but is not limited to the evaluation of the aforementioned pluripotent stem cell characteristics. Such pluripotent stem cell characteristics include without further limitation, the expression or non-expression of certain combinations of molecular markers. Further, cell morphologies associated with pluripotent stem cells are also pluripotent stem cell characteristics.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme or nucleic acid. In some embodiments contacting includes allowing a compound described herein to interact with a protein or enzyme that is involved in a signaling pathway.

The term "modulator" refers to a composition that increases or decreases the level of a target molecule or the function of a target molecule or the physical state of the target of the molecule or the target molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, or any other method of administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "associated" or "associated with" in the context of a substance or substance activity or function associated with a disease means that the disease is caused by (in whole or in part), or a symptom of the disease is caused by (in whole or in part) the substance or substance activity or function.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components.

Methods

In a first aspect a method of expressing an Oct4 protein in a cell is provided. The method includes contacting a cell with a compound having the formula:

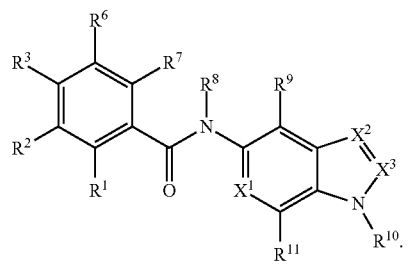

$X^1$ is $C(R^{12})$ or N. $X^2$ is $C(R^4)$ or N. $X^3$ is $C(R^5)$ or N. $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or a pharmaceutically acceptable salt thereof (including embodiments). $R^2$ and $R^3$ are optionally joined to form a substituted or unsubstituted cycloalkyl, substituted or unsubstituted heterocycloalkyl, substituted or unsubstituted aryl, or substituted or unsubstituted heteroaryl. The method further includes, after the contacting step, allowing the cell to express an Oct4 protein. Thus, the methods provided herein are useful in increasing expression of an Oct4 protein in a cell relative to expression of the Oct4 protein in the cell in the absence of the compound.

In another aspect, a method is provided for expressing an Oct4 mRNA in a cell including contacting the cell with a compound of Formula (I) (including embodiments). Also provided is a method for expressing an Oct4 mRNA and an Oct4 protein in a cell including contacting the cell with a compound of Formula (I) (including embodiments). Also provided is a method for expressing an Oct4 mRNA or an Oct4 protein in a cell including contacting the cell with a compound of Formula (I) (including embodiments).

In another aspect, a method of expressing a Nanog protein in a cell is provided. The method includes contacting a cell with a compound of Formula (I) (including embodiments). The method further includes, after the contacting step, allowing the cell to express a Nanog protein. Thus, the methods provided herein are useful in increasing expression of a Nanog protein in a cell relative to expression of the Nanog protein in the cell in the absence of the compound.

In another aspect, a method is provided for expressing a Nanog mRNA in a cell and including contacting the cell with a compound of Formula (I) (including embodiments). Also provided for is a method for expressing a Nanog mRNA and a Nanog protein in a cell including contacting the cell with a compound of Formula (I) (including embodiments). Also provided is a method for expressing a Nanog mRNA or a Nanog protein in a cell including contacting the cell with a compound of Formula (I) (including embodiments).

In another aspect, a method of making (e.g. forming) an induced pluripotent stem cell is provided. The method includes contacting a non-pluripotent cell with a compound of Formula (I) (including embodiments). The method further includes, after the contacting step, allowing the non-pluripotent cell to divide thereby forming said induced pluripotent stem cell. Thus, the methods provided herein are useful in deriving (also commonly referred to as "reprogramming") a pluripotent stem cell from a non-pluripotent cell to form an induced pluripotent stem cell.

In embodiments, prior to allowing the non-pluripotent cell to divide, the non-pluripotent cell is transfected with a nucleic acid encoding an Oct4 protein or a recombinant Oct4 protein is introduced to the non-pluropotent cell. In a further embodiment, prior to the contacting step, the non-pluripotent cell is transfected with a nucleic acid encoding a Nanog protein or a recombinant Nanog protein is introduced to the non-pluropotent cell. In a further embodiment, prior to the contacting step, the non-pluripotent cell is transfected with a nucleic acid encoding a Sox2 protein, a recombinant Sox2 protein is introduced to the non-pluropotent cell, or said non-pluripotent cell is contacted with a Sox2 expression inducer. In a further embodiment, prior to the contacting step, the non-pluripotent cell is transfected with a nucleic acid encoding a cMyc protein, a recombinant cMyc protein is introduced to the non-pluripotent cell, or said non-pluripotent cell is contacted with a cMyc expression inducer. In a further embodiment, prior to the contacting step, the non-pluripotent cell is transfected with a nucleic acid encoding a Lin28 protein, a recombinant Lin28 protein is introduced to the non-pluropotent cell, or said non-pluripotent cell is contacted with a Lin28 expression inducer. In a further embodiment, prior to the contacting step, the non-pluripotent cell is transfected with a nucleic acid encoding a Klf4 protein, a recombinant Klf4 protein is introduced to the non-pluropotent cell, or said non-pluripotent cell is contacted with a Klf4 expression inducer.

In some embodiments, the Sox2 expression inducer is a small molecule Sox2 expression inducer. The Sox2 expression inducer may be BIX, BayK, CHIR99021, tranylcypromine, E-616452, Dasatinib, iPY, PP1, n-Butylidenephthalide, AMI-5, PS48, sodium butyrate, A-83-1, PD0325901, or SB431542. In some embodiments, the Sox2 expression inducer is a Sox2 expression inducer that is not a small molecule. The Sox expression inducer may be an Alk5 inhibitor or LIF. In embodiments, the Sox2 expression inducer is selected from the group consisting of BIX, BayK, CHIR99021, tranylcypromine, E-616452, Dasatinib, iPY, PP1, n-Butylidenephthalide, AMI-5, PS48, sodium butyrate, A-83-1, PD0325901, SB431542, an Alk5 inhibitor, and LIF.

In some embodiments, the cMyc expression inducer is a small molecule cMyc expression inducer. The cMyc expression inducer may be CHIR99021, BIX, BayK, valproic acid, 5'-azacytidine, 5-aminoimidazole-4-carboxamide-I-b-riboside, AMI-5, sodium butyrate, PS48, A-83-1, SB431542, or PD0325901. In some embodiments, the cMyc expression inducer is a cMyc expression inducer that is not a small molecule. The cMyc expression inducer may be an Alk5 inhibitor or LIF. In embodiments, the cMyc expression inducer is selected from the group consisting of CHIR99021, BIX, BayK, valproic acid, 5'-azacytidine, 5-aminoimidazole-4-carboxamide-I-b-riboside, AMI-5, sodium butyrate, PS48, A-83-1, SB431542, PD0325901, an Alk5 inhibitor, and LIF.

In some embodiments, the Klf4 expression inducer is a small molecule Klf4 expression inducer. The small molecule Klf4 expression inducer may be valproic acid, kenpaullone, 5-aminoimidazole-4-carboxamide-I-b-riboside, AMI-5, sodium butyrate, PS48, A-83-1, PD0325901, or SB431542.

In some embodiments, the Lin28 expression inducer is a small molecule Lin28 expression inducer. The small molecule Lin28 expression inducer may be CHIR99021, BIX, BayK, E-616452, Dasatinib, iPY, PP1, valproic acid, 5'-azacytidine, AMI-5, A-83-01, sodium butyrate, PS48, PD0325901, or SB431542.

In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, or substituted or unsubstituted heterocycloalkyl. In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —CF$_3$, —CCl$_3$, —OH, —SH, —SO$_3$H, —C(O)OH, —C(O)NH$_2$, substituted or unsubstituted alkyl or substituted or unsubstituted heteroalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl, substituted or unsubstituted 2 to 10 membered heteroalkyl, or substituted or unsubstituted 3 to 8 membered heterocycloalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl or substituted or unsubstituted 2 to 10 membered heteroalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl, unsubstituted heteroalkyl, or unsubstituted heterocycloalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl, unsubstituted heteroalkyl, or substituted heterocycloalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl or unsubstituted heteroalkyl. In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl, unsubstituted 2 to 10 membered heteroalkyl, or unsubstituted 3 to 8 membered heterocycloalkyl. In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl or unsubstituted 2 to 10 membered heteroalkyl. In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl, unsubstituted 2 to 10 membered heteroalkyl, or substituted 3 to 8 membered heterocycloalkyl. In embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —CF$_3$, unsubstituted $C_1$ to $C_{10}$ alkyl or unsubstituted 2 to 10 membered heteroalkyl.

In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl or substituted or unsubstituted heteroalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl or substituted or unsubstituted 2 to 10 membered heteroalkyl. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —NH₂, —CF₃, —CCl₃, —OH, —SH, —SO₃H, —C(O)OH, —C(O)NH₂, unsubstituted alkyl or unsubstituted heteroalkyl. In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —NH₂, —CF₃, —CCl₃, —OH, —SH, —SO₃H, —C(O)OH, —C(O)NH₂, unsubstituted $C_1$ to $C_{10}$ alkyl or unsubstituted 2 to 10 membered heteroalkyl. In embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —CF₃, unsubstituted $C_1$ to $C_{10}$ alkyl or unsubstituted 2 to 10 membered heteroalkyl. In a further embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —CF₃, unsubstituted $C_1$ to $C_5$ alkyl or unsubstituted $C_1$ to $C_5$ alkoxy. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —CF₃, unsubstituted $C_1$ to $C_5$ alkyl, methoxy, ethoxy or propoxy. In embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, unsubstituted $C_1$ to $C_{10}$ alkyl or unsubstituted 2 to 10 membered heteroalkyl. In a further embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH₃)₂, unsubstituted $C_1$ to $C_5$ alkyl or unsubstituted $C_1$ to $C_5$ alkoxy. In another embodiment, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH₃)₂, unsubstituted $C_1$ to $C_5$ alkyl, methoxy, ethoxy or propoxy.

In some embodiments, at least one of $R^1$, $R^2$, $R^3$, $R^4$, $R^5$, $R^6$, $R^7$, $R^8$, $R^9$, $R^{10}$, $R^{11}$ and $R^{12}$ are not hydrogen. In a further embodiment, $R^6$, $R^7$, $R^8$, $R^9$, $R^{10}$ and $R^{11}$ are hydrogen. In a further embodiment, $R^{12}$ is hydrogen. In another embodiment, at least one of $R^1$, $R^2$, $R^3$, $R^4$ or $R^5$ is not hydrogen. In some embodiments, $R^5$ is hydrogen. In some embodiments, $R^4$ is hydrogen. In some embodiments, if $R^1$ is not hydrogen then $R^3$ is not hydrogen. In some embodiments, if $R^2$ is not hydrogen then $R^3$ is not hydrogen. In some embodiments, if $R^1$ is not hydrogen then $R^2$ is not hydrogen. In a further embodiment, $R^1$ is halogen or hydrogen. In embodiments, $R^1$ is hydrogen, halogen, unsubstituted methoxy, or unsubstituted ethoxy. In embodiments, $R^2$ is hydrogen, halogen, —CF₃, unsubstituted methyl, unsubstituted methoxy, or unsubstituted ethoxy. In embodiments, $R^3$ is hydrogen, halogen, —NO₂, unsubstituted methyl, unsubstituted ethyl, unsubstituted propyl, unsubstituted methoxy, or unsubstituted ethoxy. In embodiments, $R^4$ is hydrogen, —CN, or 1-methyl-4-piperidinyl. In embodiments, $R^5$ is hydrogen or unsubstituted methyl. In a further embodiment, $R^2$ and $R^3$ are joined together to form a substituted or unsubstituted heteroaryl. In a further embodiment, $R^2$ and $R^3$ are joined together to form a substituted or unsubstituted five-membered heteroaryl. In another embodiment, $R^2$ and $R^3$ are joined together to form a substituted or unsubstituted oxadiazolyl. In another embodiment, $R^2$ and $R^3$ are joined together to form an unsubstituted oxadiazolyl. In another embodiment, $R^2$ and $R^3$ are joined together to form a substituted or unsubstituted 1,2,5-oxadiazolyl. In another embodiment, $R^2$ and $R^3$ are joined together to form an unsubstituted 1,2,5-oxadiazolyl.

In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently unsubstituted methoxy. In embodiments, $R^2$, $R^3$, and $R^7$ are unsubstituted methoxy. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —Cl. In embodiments, $R^2$ is —Cl. In embodiments, $R^7$ is unsubstituted methoxy. In at least one of $R^1$, $R^2$, $R^3$, $R^4$, $R^5$, $R^6$, $R^7$, $R^8$, $R^9$, $R^{10}$, $R^{11}$ and $R^{12}$ is independently —F. In embodiments, $R^3$ and $R^6$ are —F. In embodiments, $R^1$ is —Cl. In embodiments, $R^1$, $R^2$, $R^3$, $R^6$, and $R^7$ are —F. In embodiments, $R^2$, $R^3$, and $R^6$ are unsubstituted methoxy. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —NHC(O)OC(CH₃)₃. In embodiments, $R^3$ is independently —NHC(O)OC(CH₃)₃. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —NH₂. In embodiments, $R^3$ is —NH₂. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —CH₂NHC(O)OC(CH₃)₃. In embodiments, $R^3$ is independently —CH₂NHC(O)OC(CH₃)₃. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —CH₂NH₂. In embodiments, $R^3$ is —CH₂NH₂. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently

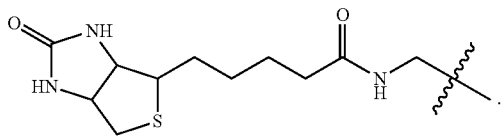 [SMILES: *CNC(=O)CCCCC1SCC2NC(=O)NC21]

In embodiments, $R^3$ is

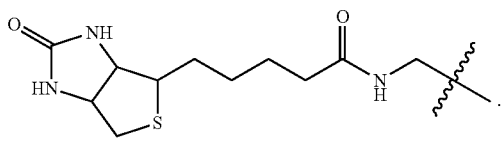 [SMILES: *CNC(=O)CCCCC1SCC2NC(=O)NC21]

In embodiments, $R^3$ is unsubstituted methoxy. In embodiments, $R^3$ is unsubstituted methoxy and $R^5$ is unsubstituted methyl. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —N(CH₃)₂. In embodiments, $R^3$ is —N(CH₃)₂. In embodiments, at least one of $R^1$, $R^2$, $R^3$, $R^4$, $R^5$, $R^6$, $R^7$, $R^8$, $R^9$, $R^{10}$, $R^{11}$ and $R^{12}$ is independently —Br. In embodiments, $R^3$ is —Br.

In some embodiments, $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO₂, —NH₂, —CF₃, —CCl₃, —OH, —SH, —SO₃H, —C(O)OH, —C(O)NH₂, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl or $R^{13}$-substituted or unsubstituted heteroaryl. In embodiments, $R^2$ and $R^3$ are optionally joined to form an $R^{13}$-substituted or unsubstituted cyclolalkyl, $R^{13}$-substituted or unsubstituted heterocycloalkyl, $R^{13}$-substituted or unsubstituted aryl, or $R^{13}$-substituted or unsubstituted heteroaryl. In embodiments, $R^2$ and $R^3$ are optionally joined to form an $R^{13}$-substituted or unsubstituted heterocycloalkyl or $R^{13}$-substituted or unsubstituted heteroaryl.

$R^{13}$ is independently halogen, —CN, —NO₂, —NH₂, —CF₃, —CCl₃, —OH, —SH, —SO₃H, —C(O)OH, —C(O)NH₂, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl or $R^{14}$-substituted or unsubstituted heteroaryl.

$R^{14}$ is independently halogen, —CN, —NO₂, —NH₂, —CF₃, —CCl₃, —OH, —SH, —SO₃H, —C(O)OH, —C(O)NH₂, $R^{15}$-substituted or unsubstituted alkyl, $R^{15}$-substituted or unsubstituted heteroalkyl, le-substituted or unsubstituted cycloalkyl, le-substituted or unsubstituted heterocycloalkyl, $R^{15}$-substituted or unsubstituted aryl or $R^{15}$-substituted or unsubstituted heteroaryl.

$R^{15}$ is independently halogen, —CN, —NO$_2$, —NH$_2$, —CF$_3$, —CCl$_3$, —OH, —SH, —SO$_3$H, —C(O)OH, —C(O)NH$_2$, unsubstituted alkyl, unsubstituted heteroalkyl, unsubstituted cycloalkyl, unsubstituted heterocycloalkyl, unsubstituted aryl or unsubstituted heteroaryl.

In some embodiments, $R^1$, $R^2$, $R^6$, and $R^7$ are hydrogen. In a further embodiment, $R^3$ is F or CH$_3$(O). In some embodiments, if $X^2$ is C($R^4$) then $X^3$ is C($R^5$).

In some embodiments, $R^1$, $R^2$, and $R^4$ are hydrogen, and $R^3$ is selected from hydrogen, substituted or unsubstituted alkyl, halogen, unsubstituted methoxy, substituted or unsubstituted ethoxy, and substituted or unsubstituted propoxy. In some embodiments, if $R^1$ is H then $R^4$ is H. In a further embodiment, $R^2$ and $R^3$ are independently selected from hydrogen, substituted or unsubstituted alkyl, halogen, substituted or unsubstituted $C_1$ to $C_5$ alkoxy, substituted or unsubstituted methoxy, substituted or unsubstituted ethoxy, or substituted or unsubstituted propoxy.

In some embodiments, $R^1$, $R^2$, and $R^4$ are hydrogen, and $R^3$ is selected from hydrogen, unsubstituted alkyl, halogen, unsubstituted methoxy, unsubstituted ethoxy, and unsubstituted propoxy. In a further embodiment, $R^2$ and $R^3$ are independently selected from hydrogen, unsubstituted alkyl, halogen, unsubstituted $C_1$ to $C_5$ alkoxy, unsubstituted methoxy, unsubstituted ethoxy, or unsubstituted propoxy.

Each alkyl, heteroalkyl, cycloalkyl, heterocycloalkyl, aryl and heteroaryl may be a size-limited substituent group. Each alkyl, heteroalkyl, cycloalkyl, heterocycloalkyl, aryl and heteroaryl may be a lower substituent group.

In embodiments, $X^1$ is C($R^{12}$). In embodiments, $X^1$ is N. In embodiments, $X^2$ is C($R^4$). In embodiments, $X^2$ is N. In embodiments, $X^3$ is C($R^5$). In embodiments, $X^3$ is N. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are hydrogen. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are halogen. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —CN. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —NO$_2$. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{19}$, $R^{11}$ and $R^{12}$ are —NH$_2$. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —CF$_3$. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —CCl$_3$. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —OH. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —SH. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —SO$_3$H. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{19}$, $R^{11}$ and $R^{12}$ are —C(O)OH. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are —C(O)NH$_2$. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{19}$, $R^{11}$ and $R^{12}$ are substituted or unsubstituted alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{19}$, $R^{11}$ and $R^{12}$ are substituted or unsubstituted cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted heterocloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted heteroaryl. In embodiments, $R^2$ and $R^3$ are optionally joined to form a substituted or unsubstituted cycloalkyl. In embodiments, $R^2$ and $R^3$ are optionally joined to form a substituted or unsubstituted heterocycloalkyl. In embodiments, $R^2$ and $R^3$ are optionally joined to form a substituted or unsubstituted aryl. In embodiments, $R^2$ and $R^3$ are optionally joined to form a substituted or unsubstituted heteroaryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted heterocycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted heteroaryl. In embodiments, one or more (e.g. 1, 2, 3, 4, 5, 6, 7, 8, 9, 10, 11, or 12) of $R'$, $R^2$, $R^3$, $R^4$, $R^5$, $R^6$, $R^7$, $R^8$, $R^9$, $R^{10}$, $R^{11}$ and $R^{12}$ are unsubstituted alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted heterocycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted heteroaryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted $C_1$ to $C_5$ alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted 2 to 5 membered heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted $C_3$ to $C_6$ cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted 3 to 6 membered heterocycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted $C_6$ to $C_{10}$ aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted or unsubstituted 5 to 10 membered heteroaryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted $C_1$ to $C_5$ alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted 2 to 5 membered heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted $C_3$ to $C_6$ cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted 3 to 6 membered heterocycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted $C_6$ to $C_{10}$ aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are substituted 5 to 10 heteroaryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted $C_1$ to $C_5$ alkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted 2 to 5 membered heteroalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted $C_3$ to $C_6$ cycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted 3 to 6 membered heterocycloalkyl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted $C_6$ to $C_{10}$ aryl. In embodiments, one or more (e.g. 1, 2, 3, 4, 5, 6, 7, 8, 9, 10, 11, or 12) of $R^1$, $R^2$, $R^3$, $R^4$, $R^5$, $R^6$, $R^7$, $R^8$, $R^9$, $R^{10}$, $R^{11}$ and $R^{12}$ are unsubstituted 5 to 10 membered heteroaryl.

In embodiments, $R^1$ is hydrogen, halogen, —CN, —NO$_2$, —CF$_3$, substituted or unsubstituted alkyl, substituted or unsubstituted heteroalkyl, or substituted or unsubstituted heterocycloalkyl. In embodiments, $R^1$ is hydrogen, halogen, substituted or unsubstituted alkyl, substituted or unsubstituted heteroalkyl, or substituted or unsubstituted heterocycloalkyl. In embodiments, $R^1$ is hydrogen. In embodiments, $R^1$ is halogen (e.g. —F, —Cl, —Br, —I). In embodiments, $R^1$ is —CN. In embodiments, $R^1$ is —NO$_2$. In embodiments, $R^1$ is —CF$_3$. In embodiments, $R^1$ is substituted or unsubstituted alkyl. In embodiments, $R^1$ is substituted or unsubstituted heteroalkyl. In embodiments, $R^1$ is substituted or unsubstituted heterocycloalkyl. In embodiments, $R^1$ is substituted or unsubstituted $C_1$ to $C_8$ alkyl. In embodiments, $R^1$ is substituted or unsubstituted 2 to 8 membered heteroalkyl. In embodiments, $R^1$ is substituted or unsubstituted 3 to 8 membered heterocycloalkyl. In embodiments, $R^1$ is unsubstituted $C_1$ to $C_3$ alkyl. In embodiments, $R^1$ is unsubstituted $C_1$ to $C_3$ alkoxy. In embodiments, $R^2$ is hydrogen, halogen, —CN, —NO$_2$, —CF$_3$, substituted or unsubstituted alkyl, substituted or unsubstituted heteroalkyl, or substituted or unsubstituted heterocycloalkyl. In embodiments, $R^2$ is hydrogen, halogen, substituted or unsubstituted alkyl, substituted or unsubstituted heteroalkyl, or substituted or unsubstituted heterocycloalkyl. In embodiments, $R^2$ is hydrogen. In embodiments, $R^2$ is halogen (e.g. —F, —Cl, —Br, —I). In embodiments, $R^2$ is —CN. In embodiments, $R^2$ is —NO$_2$. In embodiments, $R^2$ is —CF$_3$. In embodiments, $R^2$ is substituted or unsubstituted alkyl. In embodiments, $R^2$ is substituted or unsubstituted heteroalkyl. In embodiments, $R^2$ is substituted or unsubstituted heterocycloalkyl. In embodiments, $R^2$ is substituted or unsubstituted $C_1$ to $C_8$ alkyl. In embodiments, $R^2$ is substituted or unsubstituted 2 to 8 membered heteroalkyl. In embodiments, $R^2$ is substituted or unsubstituted 3 to 8 membered heterocycloalkyl. In embodiments, $R^2$ is unsubstituted $C_1$ to $C_3$ alkyl. In embodiments, $R^2$ is unsubstituted $C_1$ to $C_3$ alkoxy. In embodiments, $R^3$ is hydrogen, halogen, —CN, —NO$_2$, —CF$_3$, substituted or unsubstituted alkyl, substituted or unsubstituted heteroalkyl, or substituted or unsubstituted heterocycloalkyl. In embodiments, $R^3$ is hydrogen, halogen, substituted or unsubstituted alkyl, substituted or unsubstituted heteroalkyl, or substituted or unsubstituted heterocycloalkyl. In embodiments, $R^3$ is hydrogen. In embodiments, $R^3$ is halogen (e.g. —F, —Cl, —Br, —I). In embodiments, $R^3$ is —CN. In embodiments, $R^3$ is —NO$_2$. In embodiments, $R^3$ is —CF$_3$. In embodiments, $R^3$ is substituted or unsubstituted alkyl. In embodiments, $R^3$ is substituted or unsubstituted heteroalkyl. In embodiments, $R^3$ is substituted or unsubstituted heterocycloalkyl. In embodiments, $R^3$ is substituted or unsubstituted $C_1$ to $C_8$ alkyl. In embodiments, $R^3$ is substituted or unsubstituted 2 to 8 membered heteroalkyl. In embodiments, $R^3$ is substituted or unsubstituted 3 to 8 membered heterocycloalkyl. In embodiments, $R^3$ is unsubstituted $C_1$ to $C_3$ alkyl. In embodiments, $R^3$ is unsubstituted $C_1$ to $C_3$ alkoxy. In embodiments, $R^4$ is hydrogen, halogen, —CN, —NO$_2$, —CF$_3$, substituted or unsubstituted alkyl, substituted or unsubstituted heteroalkyl, or substituted or unsubstituted heterocycloalkyl. In embodiments, $R^4$ is hydrogen, halogen, substituted or unsubstituted alkyl, substituted or unsubstituted heteroalkyl, or substituted or unsubstituted heterocycloalkyl. In embodiments, $R^4$ is hydrogen. In embodiments, $R^4$ is halogen (e.g. —F, —Cl, —Br, —I). In embodiments, $R^4$ is —CN. In embodiments, $R^4$ is —NO$_2$. In embodiments, $R^4$ is —CF$_3$. In embodiments, $R^4$ is substituted or unsubstituted alkyl. In embodiments, $R^4$ is substituted or unsubstituted heteroalkyl. In embodiments, $R^4$ is substituted or unsubstituted heterocycloalkyl. In embodiments, $R^4$ is substituted or unsubstituted $C_1$ to $C_8$ alkyl. In embodiments, $R^4$ is substituted or unsubstituted 2 to 8 membered heteroalkyl. In embodiments, $R^4$ is substituted or unsubstituted 3 to 8 membered heterocycloalkyl. In embodiments, $R^4$ is unsubstituted $C_1$ to $C_3$ alkyl. In embodiments, $R^4$ is unsubstituted $C_1$ to $C_3$ alkoxy. In embodiments, $R^5$ is hydrogen, halogen, —CN, —NO$_2$, —CF$_3$, substituted or unsubstituted alkyl, substituted or unsubstituted heteroalkyl, or substituted or unsubstituted heterocycloalkyl. In embodiments, $R^5$ is hydrogen, halogen, substituted or unsubstituted alkyl, substituted or unsubstituted heteroalkyl, or substituted or unsubstituted heterocycloalkyl. In embodiments, $R^5$ is hydrogen. In embodiments, $R^5$ is halogen (e.g. —F, —Cl, —Br, —I). In embodiments, $R^5$ is —CN. In embodiments, $R^5$ is —NO$_2$. In embodiments, $R^5$ is —CF$_3$. In embodiments, $R^5$ is substituted or unsubstituted alkyl. In embodiments, $R^5$ is substituted or unsubstituted heteroalkyl. In embodiments, $R^5$ is substituted or unsubstituted heterocycloalkyl. In embodiments, $R^5$ is substituted or unsubstituted $C_1$ to $C_8$ alkyl. In embodiments, $R^5$ is substituted or unsubstituted 2 to 8 membered heteroalkyl. In embodiments, $R^5$ is substituted or unsubstituted 3 to 8 membered heterocycloalkyl. In embodiments, $R^5$ is unsubstituted $C_1$ to $C_3$ alkyl. In embodiments, $R^5$ is unsubstituted $C_1$ to $C_3$ alkoxy.

In embodiments, $R^2$ and $R^3$ are optionally joined to form a substituted or unsubstituted cycloalkyl. In embodiments, $R^2$ and $R^3$ are optionally joined to form a substituted or unsubstituted heterocycloalkyl. In embodiments, $R^2$ and $R^3$ are optionally joined to form a substituted or unsubstituted aryl. In embodiments, $R^2$ and $R^3$ are optionally joined to form a substituted or unsubstituted heteroaryl. In embodiments, $R^2$ and $R^3$ are optionally joined to form a substituted cycloalkyl. In embodiments, $R^2$ and $R^3$ are optionally joined to form a substituted heterocycloalkyl. In embodiments, $R^2$ and $R^3$ are optionally joined to form a substituted aryl. In embodiments, $R^2$ and $R^3$ are optionally joined to form a substituted heteroaryl. In embodiments, $R^2$ and $R^3$ are optionally joined to form an unsubstituted cycloalkyl. In embodiments, $R^2$ and $R^3$ are optionally joined to form an unsubstituted heterocycloalkyl. In embodiments, $R^2$ and $R^3$ are optionally joined to form an unsubstituted aryl. In embodiments, $R^2$ and $R^3$ are optionally joined to form an unsubstituted heteroaryl. In embodiments, $R^2$ and $R^3$ are optionally joined to form a substituted or unsubstituted $C_4$ to $C_5$ cycloalkyl. In embodiments, $R^2$ and $R^3$ are optionally joined to form a substituted or unsubstituted 4 to 5 membered heterocycloalkyl. In embodiments, $R^2$ and $R^3$ are optionally joined to form a substituted or unsubstituted $C_5$ to $C_{10}$ aryl. In embodiments, $R^2$ and $R^3$ are optionally joined to form a substituted or unsubstituted 5 to 9 membered heteroaryl. In embodiments, $R^2$ and $R^3$ are optionally joined to form a substituted $C_4$ to $C_5$ cycloalkyl. In embodiments, $R^2$ and $R^3$ are optionally joined to form a substituted 4 to 5 membered heterocycloalkyl. In embodiments, $R^2$ and $R^3$ are optionally joined to form a substituted $C_5$ to $C_{10}$ aryl. In embodiments, $R^2$ and $R^3$ are optionally joined to form a substituted 5 to 9 membered heteroaryl. In embodiments, $R^2$ and $R^3$ are optionally joined to form an unsubstituted $C_4$ to $C_5$ cycloalkyl. In embodiments, $R^2$ and $R^3$ are optionally joined to form an unsubstituted 4 to 5 membered heterocycloalkyl. In embodiments, $R^2$ and $R^3$ are optionally joined to form an unsubstituted $C_5$ to $C_{10}$ aryl. In embodiments, $R^2$ and $R^3$ are optionally joined to form an unsubstituted 5 to 9 membered heteroaryl.

In some embodiments, the compound has the formula:

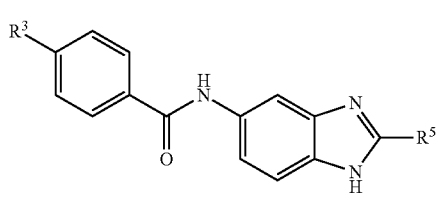

(II)

In Formula (II), $R^3$ and $R^5$ are as described herein (e.g. in Formula (I), including embodiments). In some embodiments, $R^3$ is selected from hydrogen, substituted or unsubstituted alkyl, halogen, —N(CH$_3$)$_2$, substituted or unsubstituted $C_1$ to $C_5$ alkoxy, substituted or unsubstituted methoxy, substituted or unsubstituted ethoxy or substituted or unsubstituted propoxy. In some embodiments $R^3$ is substituted or unsubstituted methoxy. In some embodiments $R^3$ is fluoride. In some embodiments $R^3$ is hydrogen. In some embodiments $R^3$ is substituted or unsubstituted ethoxy. In some embodiment $R^3$ is substituted or unsubstituted ethyl. In some embodiments $R^3$ is substituted or unsubstituted iso-propyl. In some embodiments, $R^3$ is selected from hydrogen, unsubstituted alkyl, halogen, or unsubstituted $C_1$ to $C_5$ alkoxy, unsubstituted methoxy, unsubstituted ethoxy or unsubstituted propoxy. In some embodiments $R^3$ is unsubstituted methoxy. In some embodiments $R^3$ is unsubstituted ethoxy. In some embodiment $R^3$ is unsubstituted ethyl. In some embodiments $R^3$ is unsubstituted iso-propyl. In embodiments, $R^3$ is —NO$_2$. In embodiments, $R^3$ is —N(CH$_3$)$_2$. In embodiments, $R^5$ is hydrogen. In embodiments, $R^5$ is substituted or unsubstituted $C_1$ to $C_5$ alkyl. In embodiments, $R^5$ is substituted $C_1$ to $C_5$ alkyl. In embodiments, $R^5$ is unsubstituted methyl. In embodiments, $R^5$ is —N(CH$_3$)$_2$.

In some embodiments, the compound has the formula:

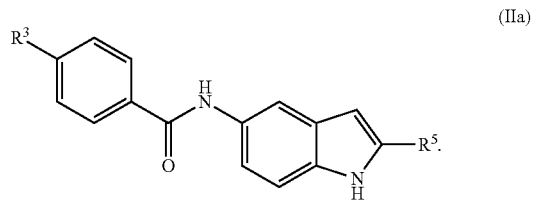

(IIa)

In Formula (IIa), $R^3$ and $R^5$ are as described herein (e.g. in Formula (II), including embodiments).

In another embodiment, the compound has the formula:

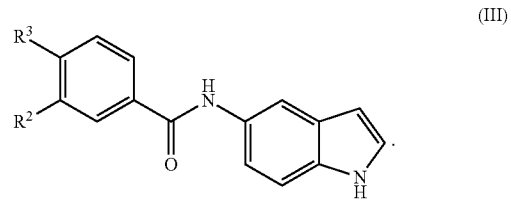

(III)

In Formula (III), $R^2$ and $R^3$ are as described herein (e.g. Formula (I), (II), or (IIa), including embodiments). In some embodiments, $R^2$ is hydrogen or =N—O—N=. $R^3$ is selected from hydrogen or =N—O—N=. In some embodiments $R^2$ is hydrogen and $R^3$ is unsubstituted methoxy. $R^2$ and $R^3$ may be optionally joined to form an oxadiazolyl.

In another embodiment, the compound has the formula:

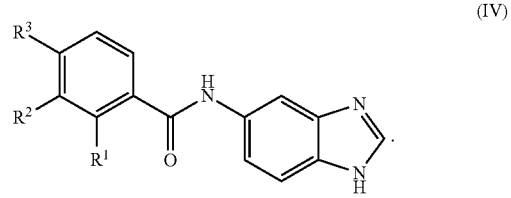

(IV)

In Formula (IV), $R^1$, $R^2$ and $R^3$ are as described herein (e.g. in formula I, II, (IIa), or III and including embodiments). In some embodiments, $R^1$ is hydrogen or halogen. $R^2$ may be selected from hydrogen, substituted or unsubstituted alkyl or substituted or unsubstituted $C_1$ to $C_5$ alkoxy, substituted or unsubstituted methoxy, or substituted or unsubstituted ethoxy. $R^3$ may be selected from hydrogen, substituted or unsubstituted alkyl, substituted or unsubstituted heteroalkyl, or halogen. $R^3$ may be selected from hydrogen, substituted or unsubstituted alkyl, or halogen. In some embodiments $R^1$ is chloride and $R^2$ is hydrogen and $R^3$ is chloride. In some embodiments $R^1$ is hydrogen and $R^2$ is substituted or unsubstituted $C_1$ to $C_5$ alkoxy, substituted or unsubstituted methoxy, or substituted or unsubstituted ethoxy and $R^3$ is hydrogen. In a further embodiment $R^1$ is hydrogen and $R^2$ is substituted or unsubstituted methoxy and $R^3$ is hydrogen. In a further embodiment $R^1$ is hydrogen and $R^2$ is substituted or unsubstituted ethoxy and $R^3$ is hydrogen. In some embodiments $R^1$ is hydrogen and $R^2$ is substituted or unsubstituted methyl and $R^3$ is substituted or unsubstituted methyl. $R^2$ may be selected from hydrogen, unsubstituted alkyl or unsubstituted $C_1$ to $C_5$ alkoxy, unsubstituted methoxy, or unsubstituted ethoxy. $R^3$ may be selected from hydrogen, unsubstituted alkyl, or halogen. In some embodiments $R^1$ is chloride and $R^2$ is hydrogen and $R^3$ is chloride. In some embodiments $R^1$ is hydrogen and $R^2$ is unsubstituted $C_1$ to $C_5$ alkoxy, unsubstituted methoxy, or unsubstituted ethoxy and $R^3$ is hydrogen. In a further embodiment $R^1$ is hydrogen and $R^2$ is unsubstituted methoxy and $R^3$ is hydrogen. In a further embodiment $R^1$ is hydrogen and $R^2$ is unsubstituted ethoxy and $R^3$ is hydrogen. In some embodiments $R^1$ is hydrogen and $R^2$ is unsubstituted methyl and $R^3$ is unsubstituted methyl.

In another embodiment, the compound has the formula:

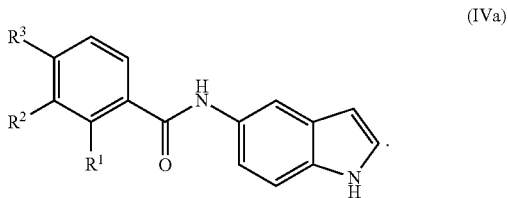

(IVa)

In Formula (IVa), $R^1$, $R^2$ and $R^3$ are as described herein (e.g. in formula I, II, (IIa), III, or (IV), and including embodiments).

In a further embodiment, the compound has the formula:

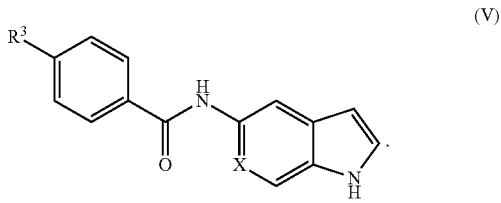

(V)

In Formula (V), X and $R^3$ are as described herein (e.g. formula I, II, (IIa), III, IV, or (IVa), including embodiments). In some embodiments, X is N or CH. In some embodiments, X is N. In some embodiments, X is CH. $R^3$ may be H or substituted or unsubstituted methoxy. $R^3$ may be H or unsubstituted methoxy. In some embodiments, X is N and $R^3$ is H. In some embodiments, X is CH and $R^3$ is H. In some embodiments, X is CH and $R^3$ is —F. In some embodiments, X is N and $R^3$ is —F.

In some embodiments, the compound of Formula (I) is one or more of the compounds set forth in Table 1. In some embodiments, the compound of Formula (I) is one or more of OAC 1 to OAC 18. The compound of Formula (I) may also be one or more of OAC1, OAC2, OAC3, OAC4, or OAC6. The compound of Formula (I) may also be one or more of OAC1, OAC2 or OAC3. In embodiments, the compound is a compound described herein, including in aspects, embodiments, methods, compositions, mixtures, kits, examples, tables, figures, and/or claims. In embodiments, the compound is not C16. In embodiments, the compound is not C30. In embodiments, the compound is not C31. In embodiments, the compound of Formula (I) is not a compound selected from the group consisting of C16-C42. In embodiments, the compound of Formula (I) is not C16-C42.

In some embodiments the cell is an adult stem cell, tissue specific progenitor cell, primary cell, secondary cell, or a cell derived from a mammalian (e.g. human or human patient) tissue (e.g. blood cell, fibroblast or other somatic cell). In some embodiments, the cell is a hIMR90 fibroblast, a mouse embryonic fibroblast (MEF) or a CV1 cell. In some embodiments the non-pluripotent cell is an adult stem cell, tissue specific progenitor cell, primary cell, secondary cell, or a cell derived from a mammalian (e.g. human or human patient) tissue (e.g. blood cell, fibroblast or other somatic cell). In some embodiments, the non-pluripotent cell is a hIMR90 fibroblast, a mouse embryonic fibroblast (MEF) or a CV1 cell.

In embodiments of any of the methods described herein, the compound of formula (I) is a compound described herein, including in an aspect, embodiment, example, table, figure, and/or claim. In embodiments of any of the methods described herein, the compound of formula (I) is OAC1. In embodiments of any of the methods described herein, the compound of formula (I) is OAC2. In embodiments of any of the methods described herein, the compound of formula (I) is OAC3. In embodiments of any of the methods described herein, the compound of formula (I) is OAC4. In embodiments of any of the methods described herein, the compound of formula (I) is OAC5. In embodiments of any of the methods described herein, the compound of formula (I) is OAC6. In embodiments of any of the methods described herein, the compound of formula (I) is OAC7. In embodiments of any of the methods described herein, the compound of formula (I) is OAC8. In embodiments of any of the methods described herein, the compound of formula (I) is OAC9. In embodiments of any of the methods described herein, the compound of formula (I) is OAC10. In embodiments of any of the methods described herein, the compound of formula (I) is OAC11. In embodiments of any of the methods described herein, the compound of formula (I) is OAC12. In embodiments of any of the methods described herein, the compound of formula (I) is OAC13. In embodiments of any of the methods described herein, the compound of formula (I) is OAC14. In embodiments of any of the methods described herein, the compound of formula (I) is OAC 15. In embodiments of any of the methods described herein, the compound of formula (I) is C16. In embodiments of any of the methods described herein, the compound of formula (I) is C17. In embodiments of any of the methods described herein, the compound of formula (I) is C18. In embodiments of any of the methods described herein, the compound of formula (I) is C19. In embodiments of any of the methods described herein, the compound of formula (I) is C20. In embodiments of any of the methods described herein, the compound of formula (I) is C21. In embodiments of any of the methods described herein, the compound of formula (I) is C22. In embodiments of any of the methods described herein, the compound of formula (I) is C23. In embodiments of any of the methods described herein, the compound of formula (I) is C24. In embodiments of any of the methods described herein, the compound of formula (I) is C25. In embodiments of any of the methods described herein, the compound of formula (I) is C26. In embodiments of any of the methods described herein, the compound of formula (I) is C27. In embodiments of any of the methods described herein, the compound of formula (I) is C28. In embodiments of any of the methods described herein, the compound of formula (I) is C29. In embodiments of any of the methods described herein, the compound of formula (I) is C30. In embodiments of any of the methods described herein, the compound of formula (I) is C31. In embodiments of any of the methods described herein, the compound of formula (I) is C32. In embodiments of any of the methods described herein, the compound of formula (I) is OAC 16. In embodiments of any of the methods described herein, the compound of formula (I) is OAC17. In embodiments of any of the methods described herein, the compound of formula (I) is OAC18. In embodiments of any of the methods described herein, the compound of formula (I) is C33. In embodiments of any of the methods described herein, the compound of formula (I) is C34. In embodiments of any of the methods described herein, the compound of formula (I) is C35. In embodiments of any of the methods described herein, the compound of formula (I) is C36. In embodiments of any of the methods described herein, the compound of formula (I) is C37. In embodiments of any of the methods described herein, the compound of formula (I) is C38. In embodiments of any of the methods described herein, the compound of formula (I) is C38. In embodiments of any of the methods described herein, the compound of formula (I) is C39. In embodiments of any of the methods described herein, the compound of formula (I) is C40. In embodiments of any of the methods described herein, the compound of formula (I) is C41. In embodiments of any of the methods described herein, the compound of formula (I) is C42.

Compositions and Mixtures

In an aspect is provided a compound of Formula (I), or a pharmaceutically acceptable salt thereof, as described herein (including embodiments) (e.g. a compound of formula (I), (II), (IIa), (III), (IV), (IVa), (V), or any embodiments thereof; a compound described in an aspect, embodiment, method, figure, table, example, or claim). In embodiments, the compound is included in a pharmaceutically acceptable salt of the compound of Formula (I) as described herein (including embodiments). In embodiments, the compound of formula (I) described herein (including embodiments) is not in a pharmaceutically acceptable salt. In embodiments, the compound of Formula (I) is not C16. In embodiments, the compound of Formula (I) is not C30. In embodiments, the compound of Formula (I) is not C31. In embodiments, the compound of Formula (I) is not a compound selected from the group consisting of C16-C42. In embodiments, the compound of Formula (I) is not C16-C42.

In an aspect is provided a composition including a compound of Formula (I) as described herein, (including embodiments) (e.g. a compound of formula (I), (II), (IIa), (III), (IV), (IVa), (V), or any embodiments thereof; a compound described in an aspect, embodiment, method, figure, table, example, or claim).

In an embodiment, the composition includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. a Sox2 synthetic or recombinant mRNA), a nucleic acid encoding a Nanog protein (e.g. a Nanog synthetic or recombinant mRNA), a nucleic acid encoding a cMyc protein (e.g. a cMyc synthetic or recombinant mRNA), a nucleic acid encoding a Lin28 protein (e.g a Lin28 synthetic or recombinant mRNA), a nucleic acid encoding a Klf4 protein (e.g. a Klf4 synthetic or recombinant mRNA), a Sox2 expression inducer, a cMyc expression inducer, a Lin28 expression inducer, or a Klf4 expression inducer.

In some embodiments the composition includes a compound of Formula (I) (including embodiments) and a recombinant Oct4 protein, recombinant Sox2 protein, recombinant Nanog protein, recombinant cMyc protein, recombinant Klf4 protein, or recombinant Lin28 protein. In some embodiments the composition includes a compound of Formula (I) (including embodiments) and a recombinant Oct4 protein. In some embodiments the composition includes a compound of Formula (I) (including embodiments) and a recombinant Sox2 protein. In some embodiments the composition includes a compound of Formula (I) (including embodiments) and a recombinant Nanog protein. In some embodiments the composition includes a compound of Formula (I) and a recombinant cMyc protein. In some embodiments the composition includes a compound of Formula (I) (including embodiments) and a recombinant Klf4 protein. In some embodiments the composition includes a compound of Formula (I) (including embodiments) and a Lin28 recombinant protein.

In some embodiments, the composition includes a compound of Formula (I) (including embodiments) and a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the composition includes a compound of Formula (I) (including embodiments) and a nucleic acid encoding an Oct4 protein (e.g. Oct4 synthetic or recombinant mRNA). In some embodiments the composition includes a compound of Formula (I) (including embodiments) and a nucleic acid encoding a Sox2 protein (e.g. Sox2 synthetic or recombinant mRNA). In some embodiments the composition includes a compound of Formula (I) (including embodiments) and a nucleic acid encoding a Nanog protein (e.g. Nanog synthetic or recombinant mRNA). In some embodiments the composition includes a compound of Formula (I) (including embodiments) and a nucleic acid encoding a cMyc protein (e.g. cMyc synthetic or recombinant mRNA). In some embodiments the composition includes a compound of ormula (I) (including embodiments) and a nucleic acid encoding a Lin28 protein (e.g. Lin28 synthetic or recombinant mRNA). In some embodiments the composition includes a compound of Formula (I) (including embodiments) and a nucleic acid encoding a Klf4 protein (e.g. Klf4 synthetic or recombinant mRNA).

In embodiments, the composition includes a Sox2 expression inducer, a Lin28 expression inducer, a Klf4 expression inducer or a cMyc expression inducer; and a compound of Formula (I) (including embodiments).

In some embodiments the composition includes a compound of Formula (I) (including embodiments) and a Sox2 expression inducer. In some embodiments the composition includes a compound of Formula (I) (including embodiments) and a cMyc expression inducer. In some embodiments the composition includes a compound of Formula (I) (including embodiments) and a Lin28 expression inducer. In some embodiments the composition includes a compound of Formula (I) (including embodiments) and a Klf4 expression inducer.

In some embodiments the composition includes a compound of Formula (I) (including embodiments) and one or more of an Oct4 recombinant protein, a Sox2 recombinant protein, a Nanog recombinant protein, a cMyc recombinant protein, a Lin28 recombinant protein, or a Klf4 recombinant protein. In some embodiments the composition includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the composition includes a compound of Formula (I) (including embodiments) and one or more of a Sox2 expression inducer, a cMyc expression inducer, a Lin28 expression inducer, or a Klf4 expression inducer.

In another embodiment, the composition includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the composition includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the composition includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In some embodiments the composition includes a compound of Formula (I) (including embodiments) and at least two proteins selected from the group consisting of an Oct4 recombinant protein, a Sox2 recombinant protein, a Nanog recombinant protein, a cMyc recombinant protein, a Lin28 recombinant protein, and a Klf4 recombinant protein. In some embodiments the composition includes a compound of Formula (I) (including embodiments) and at least two nucleic acids selected from the group consisting of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), and a nucleic acid encoding a Klf4 protein (e.g. Klf4 synthetic or recombinant mRNA). In some embodiments the composition includes a compound of Formula (I) (including embodiments) and at least two inducers selected from the group consisting of a Sox2 expression inducer, a cMyc expression inducer, a Lin28 expression inducer, and a Klf4 expression inducer.

In another embodiment, the composition includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the composition includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the composition includes a compound of Formula (I) (including embodiments) and at least two of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the composition includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In some embodiments, the components of the composition are packaged into a single container. In a further embodiment, the components of the composition are packaged in a single container in a substantially aqueous solution. In a further embodiment, the composition may be dissolved in a percentage of organic solvent, such as DMSO. In some embodiments, the percentage of organic solvent is from 1% to 100%. In a further embodiment, the components of the composition are packaged in a single container as a solid, such as but not limited to, a powder, which can be dissolved or suspended.

In some embodiments, the components of the composition are packed in various separate containers. In some embodiments, some components of the composition are packed together while others are packed separately. In some embodiment, the components of the composition are packaged in separate containers, each component of the composition being suspended in a substantially aqueous solution. In another embodiment, the components of the composition are packaged in separate containers and each component is indepentyl suspended in a substantially aqueous solution or supplied as solids, such as but not limited to, powders. In some embodiments the components of the composition are packaged in separate containers and each component is packaged as a solid, such as but not limited to a powder. In some embodiments, each component of the composition may be dissolved in a percentage of organic solvent, such as DMSO. In some embodiments, the percentage of organic solvent is from 1% to 100%.

In another aspect, a cell is provided. The cell includes a compound of Formula (I) (including embodiments).

In embodiments the cell is a non-pluripotent cell. In some embodiments the cell is an adult stem cell, tissue specific progenitor cell, primary cell, secondary cell, or a cell derived from a mammalian (e.g. human or human patient) tissue (e.g. blood cell, fibroblast or other somatic cell). In some embodiments, the cell is a hIMR90 fibroblast, a mouse embryonic fibroblast (MEF) or a CV1 cell. In some embodiments, the compound is inside the cell. In further embodiments, the cell includes a recombinant Oct4 protein, a recombinant Nanog protein, a recombinant Sox2 protein, a recombinant Lin28 protein, a recombinant Klf4 protein, a recombinant cMyc protein, a Sox2 expression inducer, a Lin28 expression inducer, a Klf4 expression inducer, a cMyc expression inducer, a nucleic acid encoding an Oct4 protein (e.g. Oct4 synthetic or recombinant mRNA), a nucleic acid encoding a Nanog protein (e.g. Nanog synthetic or recombinant mRNA), a Sox2synthetic or recombinant mRNA, a nucleic acid encoding a Lin28 protein (e.g. Lin28 synthetic or recombinant mRNA), a nucleic acid encoding a Klf4 protein (e.g. Klf4 synthetic or recombinant mRNA), or a nucleic acid encoding a cMyc protein (e.g. cMyc synthetic or recombinant mRNA).

In some embodiments the cell includes a compound of Formula (I) (including embodiments) and a recombinant Oct4 protein. In some embodiments the cell includes a compound of Formula (I) (including embodiments) and a recombinant Sox2 protein. In some embodiments the cell includes a compound of Formula (I) (including embodiments) and a recombinant Nanog protein. In some embodiments the cell includes a compound of Formula (I) (including embodiments) and a recombinant cMyc protein. In some embodiments the cell includes a compound of Formula (I) (including embodiments) and a recombinant Klf4 protein. In some embodiments the cell includes a compound of Formula (I) (including embodiments) and a Lin28 recombinant protein.

In some embodiments the cell includes a compound of Formula (I) (including embodiments) and a nucleic acid encoding an Oct4 protein (e.g. Oct4 synthetic or recombinant mRNA). In some embodiments the cell includes a compound of Formula (I) (including embodiments) and a nucleic acid encoding a Sox2 protein (e.g. Sox2 synthetic or recombinant mRNA). In some embodiments the cell includes a compound of Formula (I) (including embodiments) and a nucleic acid encoding a Nanog protein (e.g. Nanog synthetic or recombinant mRNA). In some embodiments the cell includes a compound of Formula (I) (including embodiments) and a nucleic acid encoding a cMyc protein (e.g. cMyc synthetic or recombinant mRNA). In some embodiments the cell includes a compound of Formula (I) (including embodiments) and a nucleic acid encoding a Lin28 protein (e.g. Lin28 synthetic or recombinant mRNA). In some embodiments the cell includes a compound of Formula (I) (including embodiments) and a nucleic acid encoding a Klf4 protein (e.g. Klf4 synthetic or recombinant mRNA).

In some embodiments the cell includes a compound of Formula (I) and a Sox2 expression inducer. In some embodiments the cell includes a compound of Formula (I) and a cMyc expression inducer. In some embodiments the cell includes a compound of Formula (I) and a Lin28 expression inducer. In some embodiments the cell includes a compound of Formula (I) and a Klf4 expression inducer.

In some embodiments the cell includes a compound of Formula (I) (including embodiments) and one or more of an Oct4 recombinant protein, a Sox2 recombinant protein, a Nanog recombinant protein, a cMyc recombinant protein, a Lin28 recombinant protein, or a Klf4 recombinant protein. In some embodiments the cell includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the cell includes a compound of Formula (I) (including embodiments) and one or more of a Sox2 expression inducer, a cMyc expression inducer, a Lin28 expression inducer, or a Klf4 expression inducer.

In another embodiment, the cell includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the cell includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the cell includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the cell includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In some embodiments the cell includes a compound of Formula (I) (including embodiments) at least two of an Oct4 recombinant protein, a Sox2 recombinant protein, a Nanog recombinant protein, a cMyc recombinant protein, a Lin28 recombinant protein, or a Klf4 recombinant protein. In some embodiments the cell includes a compound of Formula (I) (including embodiments) and at least two of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the cell includes a compound of Formula (I) (including embodiments) at least two of a Sox2 expression inducer, a cMyc expression inducer, a Lin28 expression inducer, or a Klf4 expression inducer.

In another embodiment, the cell includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the cell includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the cell includes a compound of Formula (I) (including embodiments) and at least two of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the cell includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In another aspect, a mixture is provided. The mixture includes a cell and a compound of Formula (I) (including embodiments).

In some embodiments, the cell is a non-pluripotent cell. In some embodiments, the mixture is in a vessel, such as a reaction vessel. In another embodiment, the cell includes a recombinant Oct4 protein, a recombinant Nanog protein, a recombinant Sox2 protein, a recombinant Lin28 protein, a recombinant Klf4 protein, a recombinant cMyc protein, a Sox2 expression inducer, a Lin28 expression inducer, a Klf4 expression inducer, a cMyc expression inducer, a nucleic acid encoding an Oct4 protein (e.g. Oct4 synthetic or recombinant mRNA), a nucleic acid encoding a Nanog protein (e.g. Nanog synthetic or recombinant mRNA), a nucleic acid encoding a Sox2 protein (e.g. Sox2 synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), or a nucleic acid encoding a cMyc protein (e.g. cMyc synthetic or recombinant mRNA).

In some embodiments, the mixture is supplied in a single container. In a further embodiment, the mixture is supplied in a single container in a substantially aqueous solution. In a further embodiment, the mixture may contain a percentage of organic solvent, such as DMSO. In some embodiments, the percentage of organic solvent is from 1% to 100%. In some embodiments, the mixture is supplied in a single container as a mixture of solids, such as but not limited to, powders, which can be dissolved or suspended.

In some embodiments the mixture is in a vessel and includes a compound of Formula (I) (including embodiments) and a recombinant Oct4 protein. In some embodiments the mixture is in a vessel and includes a compound of Formula (I) (including embodiments) and a recombinant Sox2 protein. In some embodiments the mixture is in a vessel and includes a compound of Formula (I) and a recombinant Nanog protein. In some embodiments the mixture is in a vessel and includes a compound of Formula (I) (including embodiments) and a recombinant cMyc protein. In some embodiments the mixture is in a vessel and includes a compound of Formula (I) (including embodiments) and a recombinant Klf4 protein. In some embodiments the mixture is in a vessel and includes a compound of Formula (I) (including embodiments) and a Lin28 recombinant protein.

In some embodiments the mixture is in a vessel and includes a compound of Formula (I) (including embodiments) and a nucleic acid encoding an Oct4 protein (e.g. Oct4 synthetic or recombinant mRNA). In some embodiments the mixture is in a vessel and includes a compound of Formula (I) (including embodiments) and a nucleic acid encoding a Sox2 protein (e.g. Sox2 synthetic or recombinant mRNA). In some embodiments the mixture is in a vessel and includes a compound of Formula (I) (including embodiments) and a nucleic acid encoding a Nanog protein (e.g. Nanog synthetic or recombinant mRNA). In some embodiments the mixture is in a vessel and includes a compound of Formula (I) (including embodiments) and a nucleic acid encoding a cMyc protein (e.g. cMyc synthetic or recombinant mRNA). In some embodiments the mixture is in a vessel and includes a compound of Formula (I) (including embodiments) and a nucleic acid encoding a Lin28 protein (e.g. Lin28 synthetic or recombinant mRNA). In some embodiments the mixture is in a vessel and includes a compound of Formula (I) (including embodiments) and a nucleic acid encoding a Klf4 protein (e.g. Klf4 synthetic or recombinant mRNA).

In some embodiments the mixture is in a vessel and includes a compound of Formula (I) (including embodiments) and a Sox2 expression inducer. In some embodiments the mixture is in a vessel and includes a compound of Formula (I) (including embodiments) and a cMyc expression inducer. In some embodiments the mixture is in a vessel and includes a compound of Formula (I) and a Lin28 expression inducer. In some embodiments the mixture is in a vessel and includes a compound of Formula (I) (including embodiments) and a Klf4 expression inducer.

In some embodiments the mixture is in a vessel and includes a compound of Formula (I) (including embodiments) and one or more of an Oct4 recombinant protein, a Sox2 recombinant protein, a Nanog recombinant protein, a cMyc recombinant protein, a Lin28 recombinant protein, or a Klf4 recombinant protein. In some embodiments the mixture is in a vessel and includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the mixture is in a vessel and includes a compound of Formula (I) (including embodiments) and one or more of a Sox2 expression inducer, a cMyc expression inducer, a Lin28 expression inducer, or a Klf4 expression inducer.

In another embodiment, the mixture is in a vessel and includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the mixture is in a vessel and includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the mixture is in a vessel and includes a compound of Formula (I) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the mixture is in a vessel and includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In some embodiments the mixture is in a vessel and includes a compound of Formula (I) (including embodiments) and at least two proteins selected from the group consisting of an Oct4 recombinant protein, a Sox2 recombinant protein, a Nanog recombinant protein, a cMyc recombinant protein, a Lin28 recombinant protein, and a Klf4 recombinant protein. In some embodiments the mixture is in a vessel and includes a compound of Formula (I) (including embodiments) and at least two nucleic acids selected from the group consisting of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), and a nucleic acid encoding a Klf4 protein (e.g. Klf4 synthetic or recombinant mRNA). In some embodiments the mixture is in a vessel and includes a compound of Formula (I) (including embodiments) and at least two inducers selected from the group consisting of a Sox2 expression inducer, a cMyc expression inducer, a Lin28 expression inducer, and a Klf4 expression inducer.

In another embodiment, the mixture is in a vessel and includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the mixture is in a vessel and includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the mixture is in a vessel and includes a compound of Formula (I) (including embodiments) and at least two of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the mixture is in a vessel and includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

Kits

In another aspect a kit is provided. The kit includes a recombinant Oct4 protein, a recombinant Nanog protein, a recombinant Sox2 protein, a recombinant Lin28 protein, a recombinant Klf4 protein, a recombinant cMyc protein, a Sox2 expression inducer, a Lin28 expression inducer, a Klf4 expression inducer, a cMyc expression inducer, a nucleic acid encoding an Oct4 protein (e.g. Oct4 synthetic or recombinant mRNA), a nucleic acid encoding a Nanog protein (e.g. Nanog synthetic or recombinant mRNA), a nucleic acid encoding a Sox2 protein (e.g. Sox2 synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), or a nucleic acid encoding a cMyc protein (e.g. cMyc synthetic or recombinant mRNA). The kit also includes a compound of Formula (I) (including embodiments).

In some embodiments, the kit includes instructions for making a pluripotent stem cell including the steps of expressing an Oct4 protein in a cell and contacting the cell with a compound of Formula (I) (including embodiments). In some embodiments, the kit includes instructions for making a pluripotent stem cell including the steps of expressing a nanog protein in a cell and contacting the cell with a compound of Formula (I) (including embodiments). In another embodiment, the kit includes instructions for making a pluripotent stem cell including the steps of contacting a non-pluripotent cell with a compound of Formula (I) (including embodiments).

In embodiments the kit includes a compound, composition, or mixture as described herein, including in any aspect, embodiment, example, table, claim, or figure. In some embodiments the kit includes a composition or mixture that includes a compound of Formula (I) (including embodiments) and a recombinant Oct4 protein. In some embodiments the kit includes a composition or mixture that includes a compound of Formula (I) (including embodiments) and a recombinant Sox2 protein. In some embodiments the kit includes a composition or mixture that includes a compound of Formula (I) (including embodiments) and a recombinant Nanog protein. In some embodiments the kit includes a composition or mixture that includes a compound of Formula (I) (including embodiments) and a recombinant cMyc protein. In some embodiments the kit includes a composition or mixture that includes a compound of Formula (I) and a recombinant Klf4 protein. In some embodiments the kit includes a composition or mixture that includes a compound of Formula (I) (including embodiments) and a Lin28 recombinant protein.

In some embodiments the kit includes a composition or mixture that includes a compound of Formula (I) (including embodiments) and a nucleic acid encoding an Oct4 protein (e.g. Oct4 synthetic or recombinant mRNA). In some embodiments the kit includes a composition or mixture that includes a compound of Formula (I) (including embodiments) and a nucleic acid encoding a Sox2 protein (e.g. Sox2 synthetic or recombinant mRNA). In some embodiments the kit includes a composition or mixture that includes a compound of Formula (I) (including embodiments) and a nucleic acid encoding a Nanog protein (e.g. Nanog synthetic or recombinant mRNA). In some embodiments the kit includes a composition or mixture that includes a compound of Formula (I) (including embodiments) and a nucleic acid encoding a cMyc protein (e.g. cMyc synthetic or recombinant mRNA). In some embodiments the kit includes a composition or mixture that includes a compound of Formula (I) (including embodiments) and a nucleic acid encoding a Lin28 protein (e.g. Lin28 synthetic or recombinant mRNA). In some embodiments the kit includes a composition or mixture that includes a compound of Formula (I) (including embodiments) and a nucleic acid encoding a Klf4 protein (e.g. Klf4 synthetic or recombinant mRNA).

In some embodiments the kit includes a composition or mixture that includes a compound of Formula (I) (including embodiments) and a Sox2 expression inducer. In some embodiments the kit includes a composition or mixture that includes a compound of Formula (I) (including embodiments) and a cMyc expression inducer. In some embodiments the kit includes a composition or mixture that includes a compound of Formula (I) (including embodiments) and a Lin28 expression inducer. In some embodiments the kit includes a composition or mixture that includes a compound of Formula (I) (including embodiments) and a Klf4 expression inducer.

In some embodiments the kit includes a composition or mixture that includes a compound of Formula (I) (including embodiments) and one or more of an Oct4 recombinant protein, a Sox2 recombinant protein, a Nanog recombinant protein, a cMyc recombinant protein, a Lin28 recombinant protein, or a Klf4 recombinant protein. In some embodiments the kit includes a composition or mixture that includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the kit includes a composition or mixture that includes a compound of Formula (I) (including embodiments) and one or more of a Sox2 expression inducer, a cMyc expression inducer, a Lin28 expression inducer, or a Klf4 expression inducer.

In another embodiment, the kit includes a composition or mixture that includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the kit includes a composition or mixture that includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the kit includes a composition or mixture that includes a compound of Formula (I) (including embodiments) and one or more of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the kit includes a composition or mixture that includes a compound of Formula (I) (including embodiments) and one or more of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

In some embodiments the kit includes a composition or mixture that includes a compound of Formula (I) (including embodiments) and at least two proteins selected from the group consisting of an Oct4 recombinant protein, a Sox2 recombinant protein, a Nanog recombinant protein, a cMyc recombinant protein, a Lin28 recombinant protein, and a Klf4 recombinant protein. In some embodiments the kit includes a composition or mixture that includes a compound of Formula (I) (including embodiments) and at least two nucleic acids selected from the group consisting of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), and a nucleic acid encoding a Klf4 protein (e.g. Klf4 synthetic or recombinant mRNA). In some embodiments the kit includes a composition or mixture that includes a compound of Formula (I) and at least two inducers selected from the group consisting of a Sox2 expression inducer, a cMyc expression inducer, a Lin28 expression inducer, and a Klf4 expression inducer.

In another embodiment, the kit includes a composition or mixture that includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a Sox2 expression inducer, a cMyc expression inducer, a Lin28 expression inducer, or a Klf4 expression inducer. In another embodiment, the kit includes a composition or mixture that includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), or a nucleic acid encoding a Klf4 protein (e.g. Klf4 synthetic or recombinant mRNA). In some embodiments the kit includes a composition or mixture that includes a compound of Formula (I) (including embodiments) and at least two of a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer. In another embodiment, the kit includes a composition or mixture that includes a compound of Formula (I) (including embodiments) and at least two of an Oct4 recombinant protein, a Sox2 recombinant protein, a Nanog recombinant protein, a cMyc recombinant protein, a Lin28 recombinant protein, a Klf4 recombinant protein, a nucleic acid encoding an Oct4 protein (e.g. Oct4 synthetic or recombinant mRNA), a nucleic acid encoding a Sox2 protein (e.g. Sox2 synthetic or recombinant mRNA), a nucleic acid encoding a Nanog protein (e.g. Nanog synthetic or recombinant mRNA), a nucleic acid encoding a cMyc protein (e.g. cMyc synthetic or recombinant mRNA), a nucleic acid encoding a Lin28 protein (e.g. Lin28 synthetic or recombinant mRNA), a nucleic acid encoding a Klf4 protein (e.g. Klf4 synthetic or recombinant mRNA), a Sox2 expression inducer, a cMyc expression inducer, a Lin28 expression inducer, or a Klf4 expression inducer.

One of the hurdles for practical application of induced pluripotent stem cells (iPSC) is the low efficiency and slow process of reprogramming. Oct4 has been shown to be an essential regulator of embryonic stem cell (ESC) pluripotency and key to the reprogramming process. To identify small molecules that enhance reprogramming efficiency, a cell-based high-throughput screening of chemical libraries was performed. One of the compounds, termed Oct4-activating compound I (OAC1), was found to activate both Oct4 and Nanog promoter-driven luciferase reporter genes. Furthermore, when added to the reprogramming cocktail along with the quartet reprogramming factors (Oct4, Sox2, c-Myc, and Klf4), OAC1 enhanced the iPSC reprogramming efficiency and accelerated the reprogramming process. Two structural analogs of OAC1 also activated Oct4 and Nanog promoters and enhanced iPSC formation. The iPSC colonies derived using the Oct4-activating compounds along with the quartet factors exhibited typical ESC morphology, gene expression pattern, and developmental potential. OAC1 seems to enhance reprogramming efficiency in a unique manner, independent of either inhibition of the p53-p21 pathway or activation of the Wnt-β-catenin signaling. OAC1 increases transcription of the Oct4-Nanog-Sox2 triad and Tet1, a gene known to be involved in DNA demethylation.

EXAMPLES

Example 1

Figure 1:
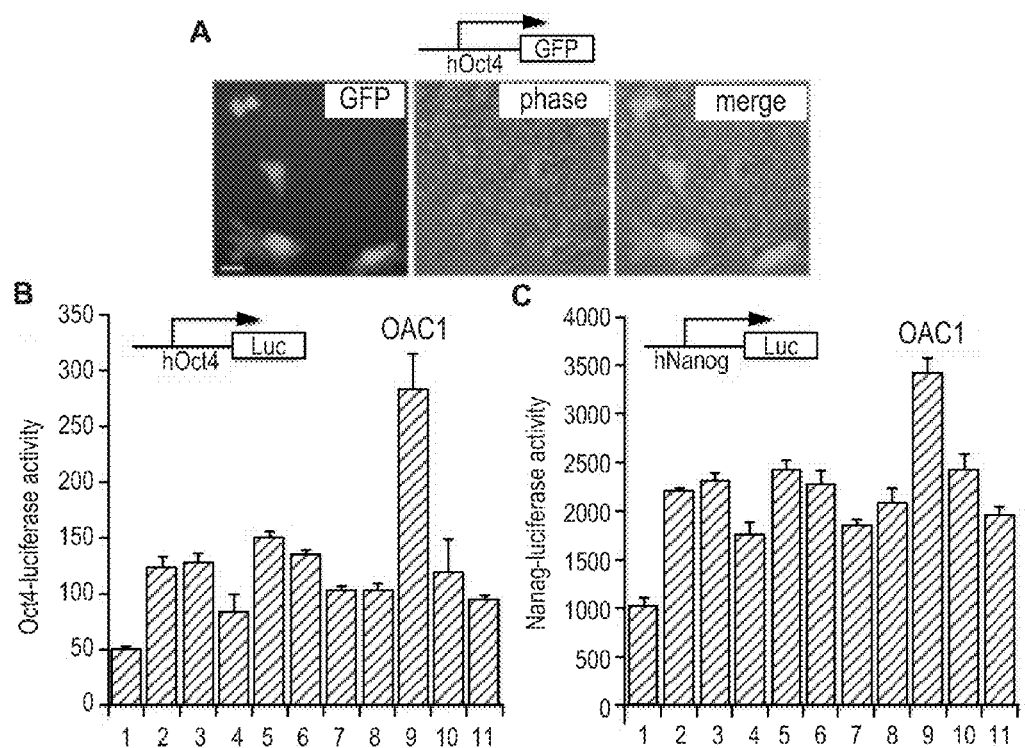
FIG. 1 Identification of Oct4-activating compounds. A. Expression of Oct4-GFP reporter in transfected mouse ESCs. Scale bar, 30 µm. B. Activation of Oct4-luc reporter by OAC1 and 9 other compounds. C. Activation of Nanog-luc reporter. Shown is an example of compound validation using triplicate luciferase reporter assays. DMSO was included as a control in lane 1 for both panels B and C.

Identification of Oct4-Activating Compounds Using High-Throughput Screening A high-throughput screening scheme was designed to identify Oct4 promoter-activating compounds using a luciferase reporter under the control of the human Oct4 promoter (Oct4-luc). The human Oct4 promoter, spanning base pairs −3917 to +55 (relative to transcription start site), contains the Oct4 ESC-specific DNA elements and was able to drive the expression of a GFP reporter gene when transfected into human ESCs (FIG. 1A). A stable cell line (Oct4-luc) that expresses luciferase reporter driven by the exogenous Oct4 promoter was established using hygromycin-resistance as a selection marker. These Oct4-luc cells were used for high-throughput screening of a chemical library of 80,000 compounds. The luciferase reporter activity was measured 24 hr after compound treatment. Solvent treatment was included as a negative control. From the primary screening, 812 compounds were identified that activate Oct4-luc activity 5-fold or more.

These compounds were confirmed for their ability to activate human Oct4 promoter in triplicate luciferase reporter assays. Oct4, Sox2, and Nanog form a positive regulatory loop to regulate the expression of each other, and Nanog is considered a downstream target gene of Oct4 and Sox2 (37). Therefore, activation of Nanog promoter was used as a validation assay for the identified compounds. Specifically, the Oct4 promoter-activating compounds were tested to ascertain whether they activate a human Nanog promoter-driven luciferase reporter gene using in triplicate luciferase reporter assays. Among the identified molecules, compound OAC1 (Oct4-activating compound I) exhibited considerable activation of both human Oct4 and Nanog reporters (FIG. 1B, C) and was selected for further characterization.

Figure 2:
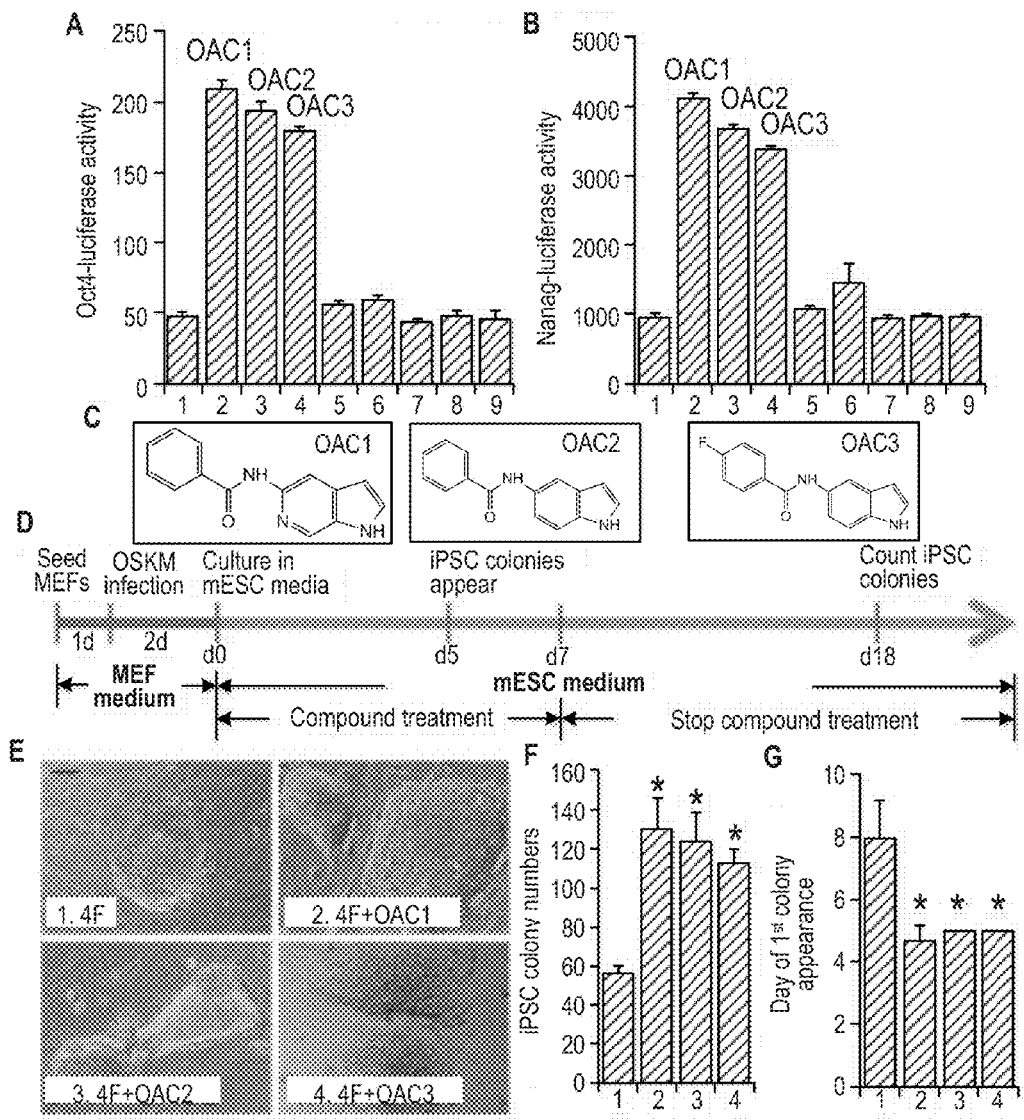
FIG. 2 Compound OAC1 and its two structural analogs enhance reprogramming efficiency. A. Compounds OAC1, OAC2, and OAC3 activated Oct4-luc reporter. B. OAC1, OAC2, and OAC3 activated Nanog-luc reporter. DMSO treatment was included as a control in lane 1. Eight structural analogs of OAC1 (lanes 2 to 9) were tested in the reporter assays for both panels A and B. C. The structure of OAC1, OAC2 and OAC3. D. Schematic representation of iPSC generation from MEF in mouse ESC media using 4F (OSKM)+ OACs. E. Images of iPSC clones from reprogramming using 4F, 4F+OAC1, 4F+OAC2, and 4F+OAC3. Scale bar, 100 µm. F. Quantification of iPSC colony numbers in 4F (1), 4F+OAC1 (2), 4F+OAC2 (3), and 4F+OAC3 (4) reprogramming. G. Kinetics of iPSC colony appearance in 4F (1), 4F+OAC1 (2), 4F+OAC2 (3), and 4F+OAC3 (4) reprogramming. *p<0.01 by one-way Anova test for both F and G. Error bars are standard deviation of the mean for all panels.

Also 31 structural analogs of OAC1 were characterized for their ability to activate Oct4 and Nanog promoter-driven reporters (Table 1). Fourteen exhibited more than 1.8-fold activation of both Oct4-luc and Nanog-luc and were considered active compounds (Table 1). Structure-activity relationship study revealed that the ring structure at both ends seems important for the Oct4 promoter-activating activity of these compounds, whereas multiple modifications of the ring structure were not favorable for this activity (Table 1). Two of the active compounds that are structurally very close to OAC 1 were selected for further analysis and designated as OAC2 and OAC3. These two compounds activated both Oct4 and Nanog reporters to a similar extent as OAC 1 (FIG. 2A, B). Their structure is shown in FIG. 2C. and Table 2.

TABLE 1

The Oct4-activating activity of compound OAC1 and its structural analogs.

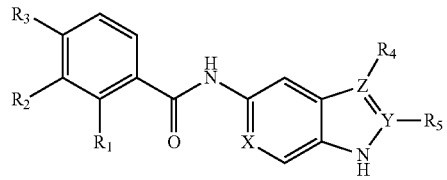

| Compound | X | Y | Z | R1 | R2 | R3 | R4 | R5 | Oct4-luc Activity | Oct4-luc fold Induction | Nanog-luc fold Induction |
|---|---|---|---|---|---|---|---|---|---|---|---|
| OAC 1 | N | C | C | H | H | H | H | H | ++ | 5.0 | 4.5 |
| OAC 2 | CH | C | C | H | H | H | H | H | ++ | 3.6 | 3.9 |
| OAC 3 | CH | C | C | H | H | F | H | H | ++ | 3.7 | 3.5 |
| OAC 4 | CH | C | C | H | H | MeO | H | H | ++ | 4.8 | 4.9 |
| OAC 5 | CH | C | C | H | =N—O—N= | | H | H | ++ | 2.9 | 2.4 |
| OAC 6 | CH | N | C | H | H | MeO | H | — | ++ | 3.2 | 2.9 |
| OAC 7 | CH | N | C | H | H | F | H | — | ++ | 2.2 | 2.0 |
| OAC 8 | CH | N | C | H | H | H | H | — | ++ | 1.9 | 1.8 |
| OAC 9 | CH | N | C | H | H | EtO | H | — | ++ | 4.4 | 4.4 |
| OAC 10 | CH | N | C | H | H | Et | H | — | ++ | 4.5 | 4.4 |
| OAC 11 | CH | N | C | H | H | iso-Pr | H | — | ++ | 3.8 | 3.9 |

TABLE 1-continued

The Oct4-activating activity of compound OAC1 and its structural analogs.

| Compound | X | Y | Z | R1 | R2 | R3 | R4 | R5 | Oct4-luc Activity | Oct4-luc fold Induction | Nanog-luc fold Induction |
|---|---|---|---|---|---|---|---|---|---|---|---|
| OAC 12 | CH | N | C | Cl | H | Cl | H | — | ++ | 3.6 | 3.4 |
| OAC 13 | CH | N | C | H | Me | Me | H | — | ++ | 2.8 | 2.9 |
| OAC 14 | CH | N | C | H | EtO | H | H | — | ++ | 2.7 | 2.6 |
| OAC 15 | CH | N | C | H | MeO | H | H | — | ++ | 1.9 | 1.9 |
| C16 | CH | C | C | H | H | F | (1-methylpiperidin-4-yl) | H | + | 1.0 | 1.1 |
| C17 | CH | C | C | H | H | Me | CN | H | + | 1.1 | 1.1 |
| C18 | CH | N | C | H | F | H | H | — | + | 1.3 | 1.2 |
| C19 | CH | N | C | H | Cl | H | H | — | + | 1.6 | 1.5 |
| C20 | CH | N | C | H | Br | H | H | — | + | 1.5 | 1.1 |
| C21 | CH | N | C | H | CF3 | H | H | — | + | 1.2 | 1.2 |
| C22 | CH | N | C | F | H | H | H | — | + | 1.5 | 1.6 |
| C23 | CH | N | C | Cl | H | H | H | — | + | 1.7 | 1.6 |
| C24 | CH | N | C | Br | H | H | H | — | + | 1.5 | 1.6 |
| C25 | CH | N | C | MeO | H | H | H | — | + | 1.5 | 1.6 |
| C26 | CH | N | C | EtO | H | H | H | — | + | 1.2 | 1.2 |
| C27 | CH | N | C | MeO | MeO | H | H | — | + | 1.4 | 1.4 |
| C28 | CH | N | C | MeO | H | MeO | H | — | + | 1.4 | 1.4 |
| C29 | CH | N | C | H | MeO | MeO | H | — | + | 1.1 | 1.1 |
| C30 | CH | N | C | H | EtO | EtO | H | — | + | 1.0 | 1.1 |
| C31 | CH | N | N | H | Cl | H | — | — | + | 1.0 | 1.1 |
| C32 | CH | C | N | H | H | NO2 | — | Me | + | 1.3 | 1.2 |
| OAC 16 | CH | C | C | H | H | MeO | H | Me | ++ | 3 | 3.43 |
| OAC 17 | CH | N | C | H | H | N(Me)2 | H | — | ++ | 4.2 | 4.56 |
| OAC 18 | CH | N | C | H | H | Br | H | — | ++ | 4.49 | 4.5 |
| C33 | 2,4,5-trimethoxy-N-(1H-indazol-5-yl)benzamide | | | | | | | | + | 1 | 1.1 |
| C34 | 5-chloro-2-methoxy-N-(1H-indazol-5-yl)benzamide | | | | | | | | + | 1.23 | 1.38 |

TABLE 1-continued
The Oct4-activating activity of compound OAC1 and its structural analogs.
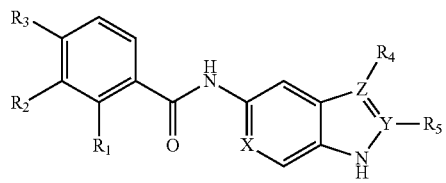
| Compound | X | Y | Z | R1 | R2 | R3 | R4 | R5 | Oct4-luc Activity | Oct4-luc fold Induction | Nanog-luc fold Induction |
|---|---|---|---|---|---|---|---|---|---|---|---|
| C35 | | | | | | | 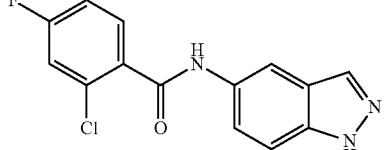 | | + | 1.15 | 1.24 |
| C36 | | | | | | | 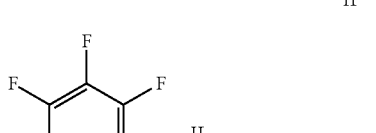 | | + | 1 | 1.02 |
| C37 | | | | | | | 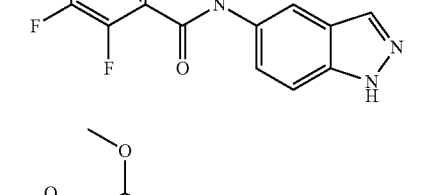 | | + | 1.055 | 1.08 |
| C38 | | | | | | | 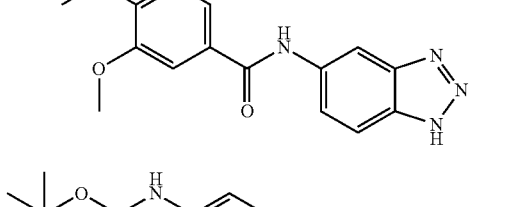 | | + | 1.2 | 1.09 |
| C39 | | | | | | | 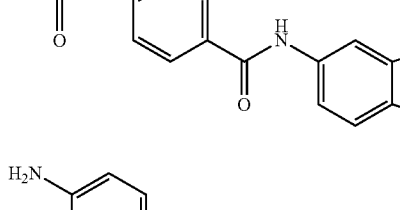 | | + | 1.62 | 1.55 |
| C40 | | | | | | | 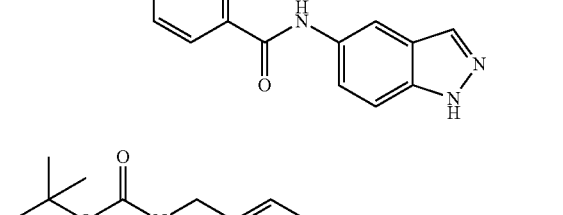 | | + | 0.97 | 0.96 |

TABLE 1-continued

The Oct4-activating activity of compound OAC1 and its structural analogs.

| Compound | X | Y | Z | R1 | R2 | R3 | R4 | R5 | Oct4-luc Activity | Oct4-luc fold Induction | Nanog-luc fold Induction |
|---|---|---|---|---|---|---|---|---|---|---|---|
| C41 | | | | | | | 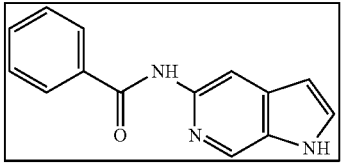 | | + | 1.01 | 1.06 |
| C42 | | | | | | | 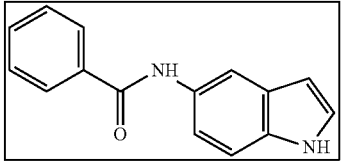 | | + | 0.91 | 0.97 |

Compounds that induce Oct4-luc 1.8-fold or more were classified as "++" and named Oct4-activating compounds (OACs), and molecules that induce Oct4-luc less than 1.8-fold were indicated as "+" and named compounds (C).

TABLE 2

OAC numbered

| COH # | M.W. | Structure | Nomenclature |
|---|---|---|---|
| (OAC1) | 237.26 | 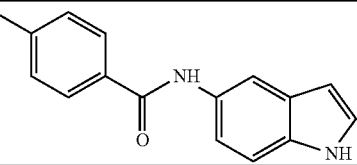 | N-(1H-6-azaindol-5-yl)benzamide |
| (OAC2) | 236.27 | 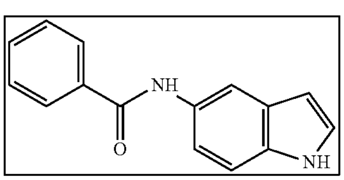 | N-(1H-indol-5-yl)benzamide |
| (OAC3) | 254.26 | 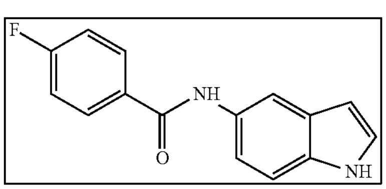 [SMILES: O=C(Nc1ccc2[nH]ccc2c1)c1ccc(F)cc1] | 4-fluoro-N-(1H-indol-5-yl)benzamide |

Example 2

OAC1 and Analogs Enhance Reprogramming Efficiency

The generation of iPSCs is a gradual process with relatively low efficiency. Since Oct4 is central to the reprogramming process (35, 36, 38), it was hypothesized that compounds that activate Oct4 transcription may facilitate iPSC generation by enhancing reprogramming efficiency. Reprogramming of mouse embryonic fibroblasts (MEFs) was performed with the 4F reprogramming quartet Oct4, Sox2, Klf4, and c-Myc, along with solvent control, OAC1 or its structural analogs OAC2 and OAC3. The same number of starting MEFs and the same viral stocks were used for each treatment. Two days after viral transduction, the 4F-transduced cells were seeded onto feeder cells in mouse ESC culture media, and this day was designated as day 0 (FIG. 2D). Compound treatment started on day 0 and lasted for 7 days. By counting the number of clones with ESC-like morphology at day 18, both OAC1 and its analogs OAC2 and OAC3 enhanced the 4F-induced reprogramming efficiency considerably. The number of colonies with ESC-like morphology (FIG. 2E) increased 2-fold or more in 4F plus OAC (4F+OAC) treatment, compared to the 4F treatment alone (FIG. 2F, Table 3).

Furthermore, addition of OAC1, OAC2, or OAC3 to the reprogramming cocktail considerably accelerated the appearance of iPSC-like colonies. Putative iPSC clones derived from the 4F+OAC1 and 4F+OAC2-treated MEFs were observed within 4 to 6 days after culturing in mouse ESC media. In contrast, the 4F treatment alone did not result in visible clones until 8-10 days after transferring to mouse ESC media. The appearance of putative iPSC colonies was advanced about three to four days in 4F+OAC-mediated reprogramming, compared to the 4F only reprogramming (FIG. 2G).

Figure 3:
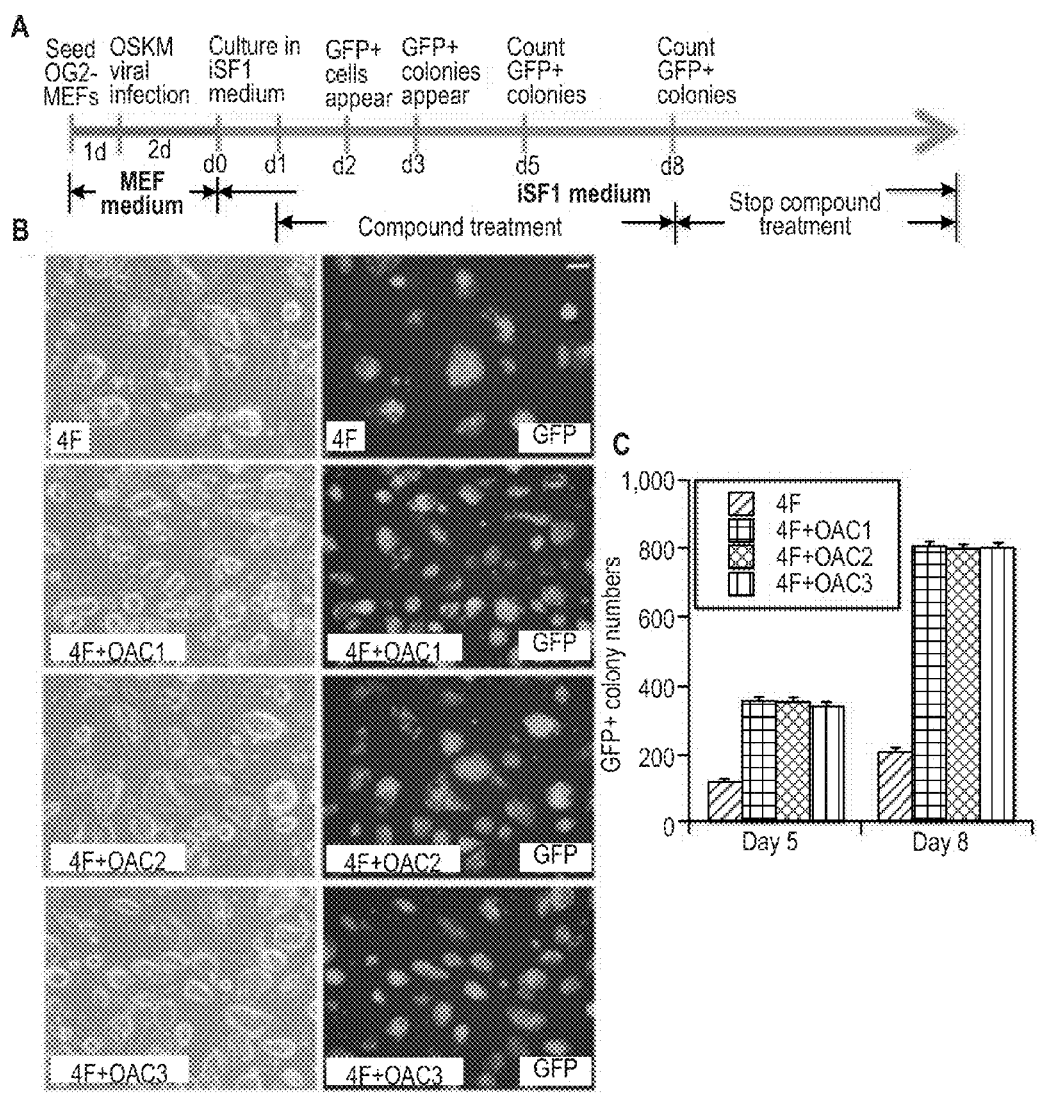
FIG. 3 OAC1 and its structural analogs enhance reprogramming efficiency in iSF1 media. A. Schematic representation of iPSC generation from MEFs in iSF1 media. B. 4F (OSKM) infected OG2-MEFs were cultured in iSF1 medium and treated with OAC1, OAC2, or OAC3 (1 µM each) for 7 days. GFP positive-colonies are shown in phase contrast and green fluorescence images. Scale bar, 100 µm. C. The number of GFP-positive colonies counted at day 5 and day 8. Error bars are standard deviation of the mean.

Recently, a serum-free media (iSF1) was developed to facilitate the generation of mouse iPSCs (39). The effect of compound OAC1 in the 4F-induced reprogramming was tested in iSF1 media. OG2 MEFs, derived from transgenic mice expressing the Oct4 promoter-driven GFP reporter (Oct4-GFP) (40), were transduced with retroviruses expressing the 4F reprogramming factors, Oct4, Sox2, Klf4, and c-Myc. The 4F-transduced cells were transferred to iSF1 media two days after viral transduction and this day was designated as day 0 (FIG. 3A). Treatment of compound OAC1 started on day 1 and lasted for 7 days. Many GFP-positive single cells were seen in C1-treated cells at day 2 and the GFP+ colonies started to appear at day 3. At day 5, a more than 3-fold increase in the number of GFP-positive colonies was detected in OAC1-treated, 4F-transduced cells (4F+OAC1), compared to vehicle-treated, 4F-transduced cells (FIG. 3B, C). A similar increase in the number of GFP+ colonies was observed in OAC2 and OAC3-treated, 4F-transduced cells (4F+OAC2, 4F+OAC3). At day 8, an approximately 4-fold increase in the number of GFP-positive colonies were observed in 4F+OAC1-treated cells (2.75% reprogramming efficiency), compared to 4F-treated cells (0.68% efficiency) (Table 3). A similar increase was observed in 4F+OAC2 and 4F+OAC3-treated cells (FIG. 3C). The number of GFP-positive colonies in 4F-treated cells at day 8 (average of 200) was less than the number of GFP-positive colonies in 4F+OAC1-treated cells at day 5 (average of 350) (FIG. 3B, C). Together, these results clearly indicate that compound OAC 1 enhances the formation of Oct4-GFP+ colonies and that OAC 1 accelerates the dynamics of reprogramming.

Example 3

Verification of Colonies as iPSCs

ESC-like colonies were picked from either 4F or 4F+OAC treatment and expanded under conventional ESC culture conditions. The 4F-induced clones were labeled as 4F-iPSCs, while the clones generated using the 4F plus the OAC compounds were indicated as 4F+OAC-iPSCs. The stably expanded 4F+OAC1-iPSCs and 4F+OAC2-iPSCs were mor-

TABLE 3

A list of reprogramming efficiency.

| Cell type | Seeding numbers | Reprogramming factors | Compound treatment | Colony numbers | Reprogramming efficiency | Reference |
|---|---|---|---|---|---|---|
| MEFs* | $3 \times 10^4$ | OSKM | — | 200 (day 8) | 0.68% | This |
|  | $3 \times 10^4$ | OSKM | OAC1 | 800 (day 8) | 2.75% | study |
| MEFs | $3 \times 10^4$ | OSKM | — | 56 (day 18) | 0.186% |  |
|  | $3 \times 10^4$ | OSKM | OAC1 | 130 (day 18) | 0.43% |  |
| MEFs | $8 \times 10^5$ | OSKM | — | 160 | 0.02% | (1) |
| MEFs | $2.7 \times 10^5$ | OSKM | — | 0 (day 8) | 0% | (2) |
|  | $2.7 \times 10^5$ | OSKM | 5-AzaC | 10 (day 8) | 0.004% |  |
|  | $2.7 \times 10^5$ | OSKM | VPA | 241 (day 8) | 0.089% |  |
| MEFs | $3.5 \times 10^4$ | OSKM | — | ~20 | 0.06% | (3) |
| MEFs | $5 \times 10^4$ | OSKM | — | 80 (day 25) | 0.12% | (4) |
|  | $5 \times 10^4$ | OSKM | Kenpaullone | 100 (day 25) | 0.2% |  |
| MEFs | 7,500 | OSKM | — | 5 (day 30) | 0.067% | (5) |
|  | 7,500 | OSKM | RepSox2 | 7.5 (day 30) | 0.1% |  |

Figure 4:
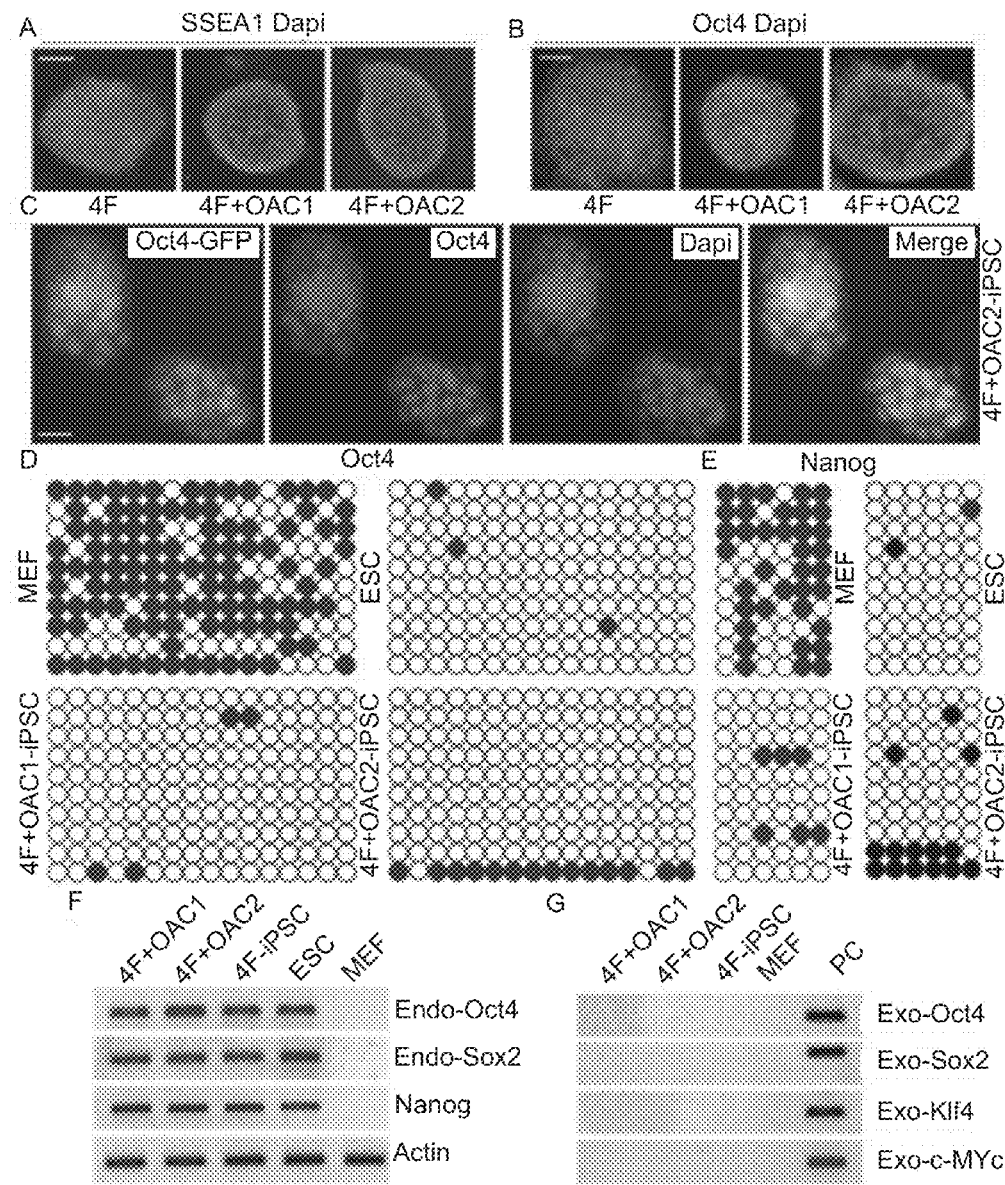
FIG. 4 Characterization of 4F+OAC-iPSCs. A. SSEA1 immunostaining of 4F, 4F+OAC1, and 4F+OAC2-iPSCs. Scale bar, 50 µm. B. Oct4 immunostaining of 4F, 4F+OAC1, and 4F+OAC2-iPSCs. Scale bar, 50 µm. C. Expression of both the Oct4-GFP reporter (green) and Oct4 (red) in 4F+OAC2-iPSCs. Scale bar, 25 µm. D, E. Bisulfite sequencing analysis of Oct4 (D) and Nanog (E) promoter regions in MEFs, mouse ESCs, 4F+OAC1 and 4F+OAC2-iPSCs. Open and closed circles indicate unmethylated and methylated CpGs, respectively. F. RT-PCR analysis of endogenous (endo) Oct4, Sox2 and Nanog expression in 4F, 4F+OAC1, and 4F+OAC2-iPSCs. Actin was included as a loading control. MEFs were included as a negative control and mouse ESCs as a positive control. G. RT-PCR analysis of exogenous (exo) viral genes in 4F, 4F+OAC1 and 4F+OAC2-iPSCs. MEFs were included as a negative control and cells transiently transfected with the viral vector of each gene was included as a positive control (PC).

(1) Takahashi, K & Yamanaka, S (2006) Induction of pluripotent stem cells from mouse embryonic and adult fibroblast cultures by defined factors. Cell 126, 663-676.
(2) Huangfu, D, et al. (2008) Induction of pluripotent stem cells by defined factors is greatly improved by small-molecule compounds. Nature Biotechnology 26, 795-797.
(3) Shi, Y, et al. (2008) Induction of pluripotent stem cells from mouse embryonic fibroblasts by Oct4 and Klf4 with small-molecule compounds. Cell Stem Cell 3, 568-574.
(4) Lyssiotis, CA, et al. (2009) Reprogramming of murine fibroblasts to induced pluripotent stem cells with chemical complementation of KIP. PNAS 106, 8912-8917.
(5) Ichida, J K, et al. (2009) A small-molecule inhibitor of tgf-Beta signaling replaces sox2 in reprogramming by inducing nanog. Cell Stem Cell 5, 491-503.
Reprogramming was performed in mouse ESC media in most cases.
*reprogramming was done in iSF1 media. The reprogramming efficiency was calculated by dividing the colony numbers with seeding cell numbers. OSKM stands for Oct4, Sox2, Klf4 and c-Myc.
"—" means no compound treatment.

phologically indistinguishable from ESCs and 4F-iPSCs (FIG. 7A). These iPSCs expressed the typical mouse ESC cell surface marker SSEA1 and the ESC pluripotency factor Oct4, as revealed by immunostaining analysis (FIG. 4A, B). The Oct4-GFP reporter was also activated in the 4F+OAC-induced iPSCs (FIG. 4C), consistent with the positive Oct4 immunostaining (FIG. 4B, C).

Bisulfite sequencing analysis revealed that the endogenous Oct4 promoter of both 4F+OAC1-iPSCs and 4F+OAC2-iPSCs was largely demethylated, similar to the hypo-methylated state of the Oct4 promoter in mouse ESCs (FIG. 4D). In contrast, the Oct4 promoter in the parental MEFs was highly methylated (FIG. 4D). Similarly, DNA methylation on the endogenous Nanog promoter was also much lower in the 4F+OAC1 and 4F+OAC2-iPSCs, compared to that in the parental MEFs (FIG. 4E).

Consistent with the hypomethylated state of the Oct4 and Nanog promoters, activation of the endogenous Oct4 and Nanog gene transcription was evident in 4F+OAC 1 and 4F+OAC2-iPSCs, similar to that in 4F-iPSCs and mouse ESCs (FIG. 4F). Activation of endogenous Sox2 gene was also detected in 4F+OAC1 and 4F+OAC2-iPSCs, similar to the Sox2 mRNA levels in 4F-iPSCs and mouse ESCs (FIG. 4F). In contrast, the four exogenous reprogramming factors, Oct4, Sox2, Klf4, and c-Myc, were all transcriptionally silenced in 4F+OAC1 and 4F+OAC2-iPSCs (FIG. 4G). The 4F+OAC1 and 4F+OAC2-iPSCs were also positive for alkaline-phosphatase, another marker of pluripotency, similar to mouse ESCs (FIG. 7B).

Example 4

Differentiation Potential of 4F+OAC-iPSCs

To examine the developmental potential of 4F+OAC 1 and 4F+OAC2-iPSCs, we differentiated these cells in vitro using a standard embryoid body (EB) differentiation approach. Immunostaining revealed that the 4F+OAC1-iPSCs and 4F+OAC2-iPSCs could effectively differentiate into characteristic FoxA2-positive endoderm cells, SMA-positive mesodermal cells, and Tuj1-positive ectoderm cells (FIG. 5A).

Figure 5:
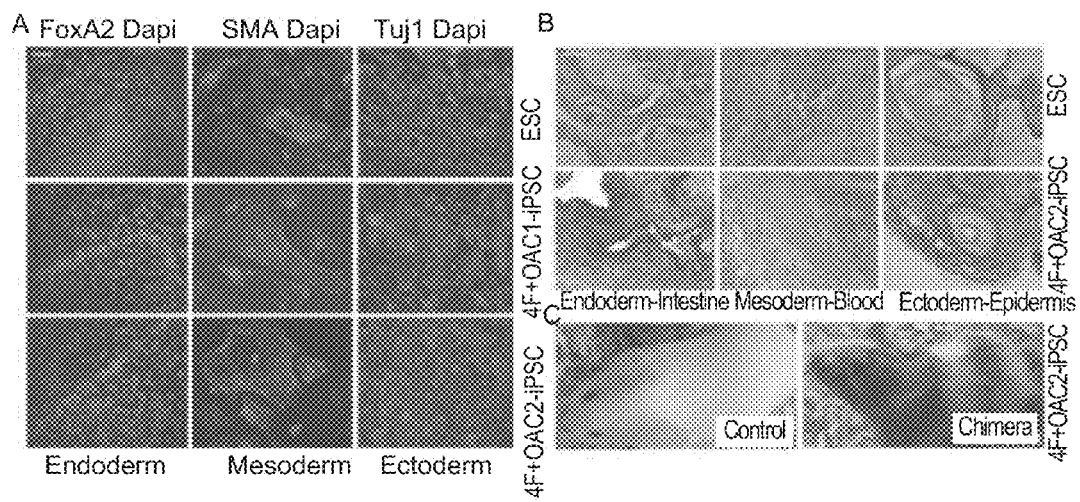
FIG. 5 Developmental potential of 4F+OAC-induced iPSCs. A. Differentiation potential of ESCs, 4F+OAC1-iPSCs, and 4F+OAC2-iPSCs in embryoid body (EB) formation assays. During EB formation, mouse ESCs, 4F+OAC1-iPSCs and 4F+OAC2-iPSCs were differentiated into FoxA2-positive endoderm, SMA-positive mesoderm, and Tuj1-positive ectoderm cells. Scale bar, 50 µm. B. Teratoma formation of 4F+OAC2-iPSCs. The tissues of all three germ layers, such as epidermis, blood, and intestinal epithelia, were detected in 4F+OAC2-iPSC-derived teratoma sections. Scale bar, 50 µm. C. Chimera mouse production using 4F+OAC2-iPSCs. Adult mice with a high degree of chimerism were developed from 4F+OAC2-iPSCs after blastocyst injection.

To test the in vivo pluripotency of the 4F+compound-induced iPSCs, we transplanted the 4F+OAC2-iPSCs into immunodeficient Nude mice. 4-6 weeks after transplantation, the 4F+OAC2-iPSCs effectively generated typical teratomas containing derivative of all three germ layers, such as intestinal epithelia of endoderm, blood of mesoderm, and epidermis of ectoderm (FIG. 5B).

A more stringent assay for pluripotency is to determine whether iPSCs can generate chimera mice. The developmental potential of the 4F+OAC-induced iPSCs was evaluated by injection of 4F+OAC2-iPSCs into diploid blastocysts. After injection into blastocysts, these iPSCs were able to produce live postnatal animals with high coat-color chimerism (FIG. 5C). The generation of viable chimeras is a further indication of the developmental potential of the 4F+OAC-induced iPS cells.

Collectively, these in vitro and in vivo results demonstrate that a set of structurally-related small molecules (OAC1-OAC3) is able to enhance the efficiency of reprogramming somatic cells to iPSCs that are morphologically, molecularly, and developmentally similar to pluripotent ESCs.

Example 5

Mechanisms

Figure 6:
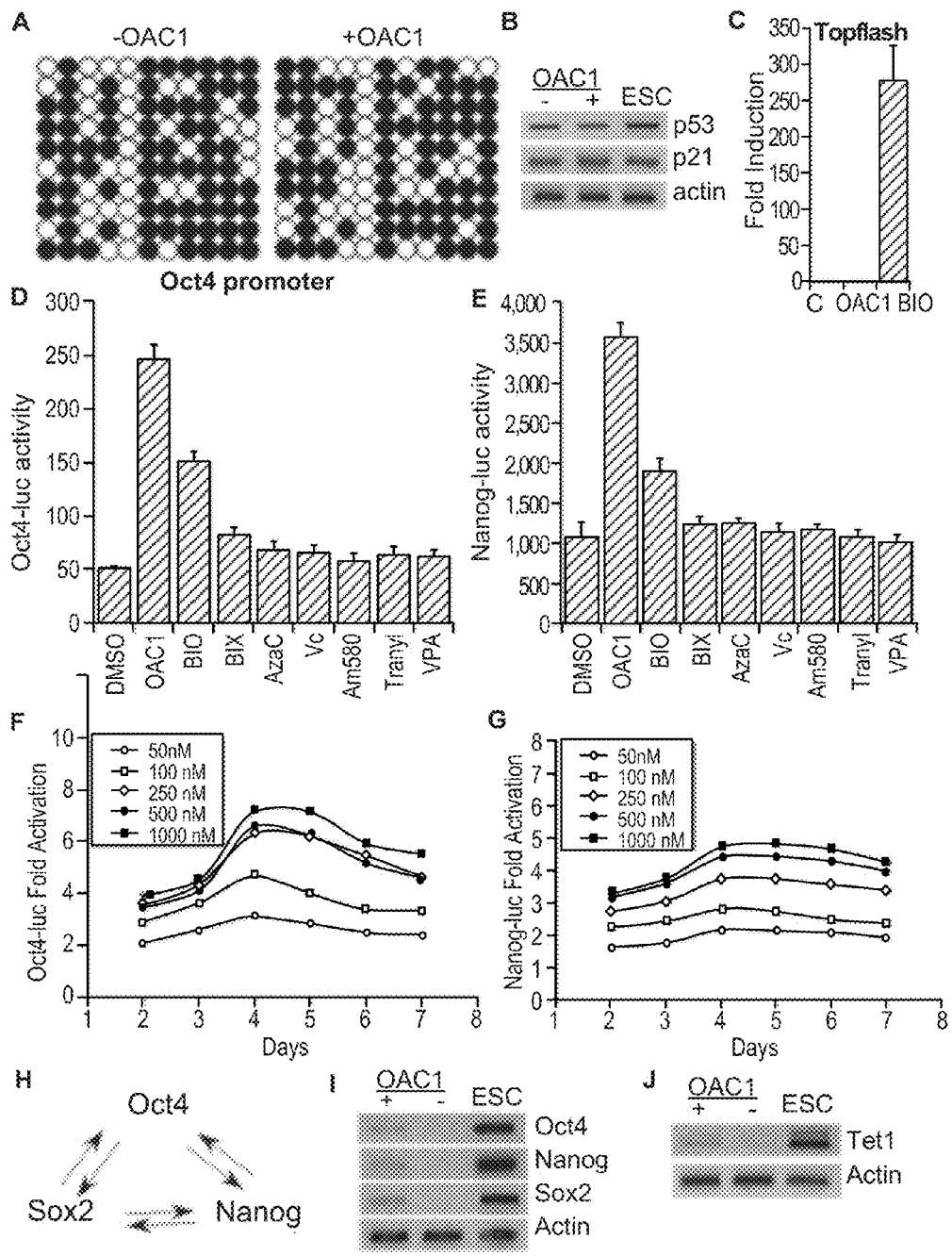
FIG. 6 OAC1 activated endogenous Oct4, Nanog, Sox2 and Tet1 expression.

To uncover the mechanism of OAC 1-mediated improvement of reprogramming efficiency, it was tested whether OAC 1 functions through regulation of DNA methylation status on the endogenous Oct4 promoter. Human IMR90 fibroblast cells were treated with OAC1 or vehicle control for two days. Bisulfite sequencing revealed no significant difference in OCT4 promoter methylation status between OAC1 and DMSO treated cells (FIG. 6A). This result indicates that OAC 1 enhanced reprogramming efficiency through a mechanism that is independent of endogenous Oct4 promoter demethylation.

Recently, the p53-p21 pathway has been shown to serve as a barrier in iPSC generation. Inhibition of the p53-p21 signaling increased reprogramming efficiency (26, 28-31, 41). To investigate whether compound OAC1 enhanced reprogramming efficiency by affecting this pathway, MEFs were treated with vehicle control or OAC1 and determined the expression level of p53 and p21 in the treated cells. RT-PCR analysis revealed no significant difference in the expression levels of both p53 and its downstream target p21 in DMSO and OAC 1-treated cells (FIG. 6B). This result suggests that OAC 1 enhanced reprogramming efficiency through a mechanism that is distinct from suppressing p53-p21 expression.

Whether OAC1 regulates major signaling pathways that are critical for embryonic stem cell pluripotency was investigated. Specifically, whether OAC1 regulates Wnt signaling, a pathway that has been shown to play an important role in ESC maintenance and pluripotency, was tested (42). CV1 cells were transfected with the β-catenin-responsive reporter gene Topflash, and the transfected cells were treated with vehicle control or OAC1 (FIG. 6C). The glycogen synthase kinase 3β (GSK3β) inhibitor BIO was included as a positive control (42). Luciferase assay revealed that OAC 1 had no effect on Topflash activity, although BIO activated the Topflash reporter potently (FIG. 6C). This result indicates that OAC1 functions through a mechanism that is independent of the Wnt signaling.

To further understand OAC 1-induced enhancement of reprogramming efficiency, the effect of OAC 1 on the activation of the Oct4 and Nanog promoters was compared to the effect of compounds that were shown to enhance reprogramming efficiency in previous studies, including BIX-01294 (BIX, an inhibitor of the G9a histone methyltransferase) (7), 5'-azacytidine (AzaC, a potent DNA methylation inhibitor) (4), Vitamin C (Vc) (12), Am580 (RAR agonist) (17), tranylcypromine (a lysine-specific histone demethylase inhibitor) (11, 43), and valproic acid (VPA, an HDAC inhibitor) (4, 5). CV1 cells that were stably-transfected with the Oct4-luc or Nanog-luc reporters were treated with OAC1. The GSK-30 inhibitor BIO was shown to maintain Oct4 expression in mouse ESCs (42) and was included as a control. The Oct4-luc and Nanog-luc transfected cells were treated in parallel with BIX, AzaC, Vc, Am580, tranylcypromine, and VPA at the same concentrations that were used to enhance reprogramming efficiency in the previous studies (4, 5, 7, 11, 12, 17, 43). OAC1 exhibited potent induction of both Oct4-luc and Nanog-luc (FIG. 6D, E). BIO displayed a lower level induction of the two reporters (FIG. 6D, E). However, no significant effect on either reporter was detected for BIX, AzaC, Vc, Am580, tranylcypromine, and VPA (FIG. 6D, E). These results revealed that OAC1 is different from other compounds that enhance reprogramming efficiency. OAC 1 may directly activate Oct4 and Nanog promoters. Although BIO also activated Oct4 and Nanog promoters, the activation level was much lower (FIG. 6D, E) and it did not exert any notable effect on reprogramming efficiency (16).

Next, the dose response and kinetics of OAC1-mediated activation of Oct4 and Nanog promoters was examined. OAC1 activated Oct4-luc considerably at 50 nM concentration, two days after compound treatment (FIG. 6F). Activation of Oct4 is dose-dependent, with highest induction at 1 μM of OAC 1. The induction is peaked around days 4 and 5 and plateaued at days 6 and 7 (FIG. 6F). A similar dose response was observed for activation of Nanog-luc by OAC1 (FIG. 6G). A substantial activation of Nanog-luc was seen by OAC1 at 50 nM. The highest induction occurred at 0.5 to 1 μM of OAC 1. The induction is evident by day 2 after compound treatment, peaked around days 4 and 5, and plateaued thereafter (FIG. 6G).

MEFs were treated with vehicle control or OAC 1 to test whether OAC 1 activates endogenous Oct4 and Nanog gene transcription. Consistent with the results from luciferase reporter assays, RT-PCR analysis revealed that OAC1 activated endogenous Oct4 and Nanog mRNA expression (FIG. 6I). Oct4, Sox2, and Nanog are central to the transcriptional regulatory hierarchy for ESC pluripotency, forming the core transcriptional regulatory circuitry in ESCs (37). Since Oct4, Nanog and Sox2 have been shown to act in positive regulatory loops to regulate each other expression (37) (FIG. 6H), Sox2 expression in OAC1-treated cells was examined. OAC1 activated Sox2 mRNA expression, along with Oct4 and Nanog (FIG. 6I).

Tet1 (Ten eleven translocation 1) has been shown to play an important role in mouse ESC maintenance through sustaining the expression of Nanog (44, 45). RT-PCR analysis revealed that Tet1 mRNA expression was also up-regulated in OAC1-treated cells (FIG. 6J). The up-regulation of Tet1 is intriguing, as this is a gene that converts 5-methylcytosine to 5-hydroxymethylcytosine and may be involved in active DNA demethylation.

Example 6

Oct4 and Nanog are two key transcription factors that function as major regulators of pluripotency and self-renewal in ESCs (46-48). Moreover, Oct4 serves as a key pluripotency determinant in reprogramming (38). Induction of endogenous Nanog expression has also been shown to be essential for successful induction of iPSCs (20). In this study, a phenotypic high-throughput screening method was developed that identified OAC 1, a small molecule that activates the expression of Oct4 and Nanog promoter-driven luciferase reporters. The transcription of endogenous Oct4 and Nanog are induced by OAC1 treatment. Furthermore, OAC1 and its two structural analogs OAC2 and OAC3 enhanced reprogramming efficiency 4-fold, up to as high as 2.75%, and accelerated the appearance of iPSC colonies three to four days when used in combination with the 4 reprogramming factors, Oct4, Sox2, Klf4, and c-Myc. These small molecule compounds represent a previously undescribed class of compounds.

The reprogramming efficiency of 4F (OSKM)+OAC1 is more than 20-fold higher than that induced by the 4F alone in the initial Yamanaka study (2). It is also higher than that induced by 4F plus other compounds, such as VPA (4), Aza-C (4), kenpaullone (14), and Repsox2 (9), based on the percent of colony numbers out of total seeding cell numbers (Table 3). It is worth noting that this is not a direct comparison. The date when the colony numbers were counted and the criteria by which the colonies were scored varied case by case.

The iSF1 medium is proven to facilitate iPSC generation by enhancing the efficiency of reprogramming (39). A screen of 16 compounds, including AzaC, TSA, VPA, and BIX, was performed to evaluate their potential to enhance reprogramming efficiency in iSF1 media (39). Among them, only VPA and TSA led to a 2-fold increase in reprogramming efficiency at day 8 post-infection of reprogramming factors, no enhancement was detected by other compounds (39). In this study, OAC1 enhanced reprogramming about 4-fold at day 8 post-infection of 4F, suggesting that OAC1 improves reprogramming efficiency more potently than other compounds tested in this reprogramming system.

A number of chemicals have been reported to improve the reprogramming efficiency, including compounds that alter DNA methylation or histone modifications (4, 5, 7, 11-13, 43). When tested in parallel, these compounds, including BIX, AzaC, Vc, Am580, Tranylcypromine, and VPA, did not activate either Oct4 or Nanog promoter-driven luciferase activity 48 hr after treatment, in contrast to the potent activation of both Oct4 and Nanog promoters by OAC 1. Although BIO also activated Oct4 and Nanog reporter activity in our assays, it activated the reporters at a much lower level and this level of activation seemed not sufficient to enhance reprogramming efficiency (16).

OAC1 and related analogs belong to a structural class of 5-substituted pyrrolo[2,3-b]pyridine- and indole-based benzamides. Very little is reported about their biological activities. OAC 1 was recently identified as a weak luciferase inhibitor with an EC50 of 6.37 μM at 40° C. using loss of enzymatic activity as a measurement (49). However, in a different assay called ATLAS (any target ligand affinity screen), no inhibition was detected (49). This result is consistent with our observation that OAC 1 exhibited no inhibition of luciferase activity when tested at 1 μM concentration, although OAC 1 induced Oct4 and Nanog reporter activity and mRNA expression at the same concentration.

The Oct4, Sox2 and Nanog triad contributes to ESC pluripotency by forming feedforward and feedback loops to induce their own expression and activate genes encoding components of key signaling pathways governing ESC pluripotency and self-renewal (37). OAC 1 activated the expression of all three factors in the triad. In addition, OAC 1 activated the expression of Tet1, a member of the Tet protein family that catalyzes the conversion of 5-methylcytosine (5mC) of DNA to 5-hydroxymethylcytosine (5hmC). Tet1 is expressed at high levels in mouse ESCs and has been shown to play an important role in ESC maintenance and pluripotency (44, 45, 50, 51). Activating the transcription of genes that are key to ESC pluripotency and self-renewal, including Oct4, Nanog, Sox2, and Tet1, provides a mechanism for compound OAC 1-induced improvement in reprogramming efficiency and dynamics. The observation of activation of Tet1 is intriguing, but further studies will be necessary to determine the mechanism(s) by which OAC 1 activates the key pluripotency genes.

iPSCs provide great hope not only for basic biology by providing experimental model systems, but also for disease prevention and treatment via stem cell-based cell replacement therapy and stem cell-based drug discovery. However, the low efficiency of iPSC reprogramming is a hurdle to iPSC applications (52). OAC1 induced iPSC colony formation 3 days after transferring the 4F-transduced cells to the iSF1 reprogramming media and the reprogramming efficiency reached 2.75% by day 8. That an Oct4-activating small molecule is able to both enhance reprogramming efficiency and accelerate the reprogramming kinetics suggests this method may be used for large-scale iPSC generation for potential clinical applications. This study also paves the way for detailed mechanistic studies to better understand the reprogramming process.

Example 7

It has been shown that compound OAC1 (Oct4-activating compound I) and two of its structural analogs OAC2 and OAC3 can enhance reprogramming efficiency, when added to the reprogramming mixture along with the four transcription factors, Oct4, Sox2, Klf4, and c-Myc (OSKM), in mouse system. The OAC compounds were tested to determine if they can enhance reprogramming efficiency in human system. The reprogramming process was performed as described in the diagram (FIG. 14a). Briefly, human fibroblast cells (IMR90) were induced to reprogram into induced pluripotent stem cells (iPSCs) using the four reprogramming factors (4F), OSKM. The day when the cells were transduced with the four reprogramming factors was referred to as day 0. Cells were cultured in IMR90 media for six days. On day 6, the transduced cells were split and seeded onto feeders. On day 7, IMR90 culture media was changed to hESC culture media and started compound treatment. Compound treatment was lasted for one week. Cells were monitored for the appearance of human embryonic stem cell (ESC)-like colonies. On day 9, several small human ESC-like colonies appeared in both 4F+OAC1 and 4F+OAC2-treated cells, however, human ESC-like colonies were not observed in 4F+vehicle (4F)-treated cells until day 11. To determine the effect of OAC on the efficiency of human iPSC derivation, the number of human ESC-like colonies were counted under all three conditions at day 18. Both OAC 1 and its structural analog OAC2 increased the number of human ESC-like colonies more than two-fold (FIG. 14b, c). The human ESC-like colonies were picked from either 4F or 4F+OAC-treated cells and expanded under human ESC culture conditions. These cells were able to expand and stably produce human iPSC clones with characteristic human ESC-like morphology (FIG. 14d). These results indicate that, similar in mouse system, the OACs were able to both enhance reprogramming efficiency and accelerate reprogramming dynamics in human iPSC derivation.

Materials and Methods

MEF Derivation: Oct4-GFP (OG2) transgenic mice harboring a GFP reporter gene under the control of the Oct4 promoter (39) were crossed with Rosa26/hprt-Cre (R26) mice (49) to get OG2/R26 mice. MEFs were derived from either OG2/R26 mice or OG2 mice for reprogramming. MEF derivation was performed according to the protocol from WiCell Research Institute.

Retrovirus Preparation: The pMX-based retroviral vectors for mouse Oct4, Sox2, Klf4 and cMyc were obtained from Addgene. Retrovirus was produced using an established protocol (50). Specifically, 4×106 293T cells were seeded onto a 10 cm dish in DMEM medium with 10% FBS 24 hr before transfection. Medium was changed 5 hr before transfection on the next day. At the time of transfection, cell confluency was around 80-90%. 15 µg of plasmid DNAs were introduced into 293T cells using calcium phosphate transfection method. Medium was changed the day after transfection. At 4872 hr after transfection, virus-containing supernatant was collected, filtered through 0.45 µm filter, and concentrated by ultracentrifugation.

iPSC Derivation in Mouse ESC Media: OG2/R26MEFs were seeded onto E-well plates at the density of 4×104 cells per well in DMEM medium with 10% FBS, 0.1 mM non-essential amino acids (NEAA), and 0.1 mM L-glutamine, 24 hr before transduction. Freshly concentrated viruses of the four factors, Oct4, Sox2, c-Myc, and Klf4, were added to the cells. Two days after viral infection, the viral-transduced OG2/R26MEFs were split into new 6-well plates with irradiated MEF feeder cells and cultured in mouse ESC culture medium containing 15% ESC qualified FBS, 2 mM L-glutamine, 0.1 mM 2-mercaptoethanol, 0.1 mM NEAA, 1 mM sodium pyruvate and 1000 U/ml of leukemia inhibitory factor (LIF), and this day was defined as day 0. 1 µM of each compound (OAC1, OAC2, and OAC3) was added to the 4F-transduced cells at day 0 and treatment was continued for 1 week. When iPSC colonies emerged, these colonies were picked for expansion on irradiated MEF feeders in mouse ESC medium.

iPSC Derivation in iSF1 Media: OG2 MEFs were seeded onto 6-well plates at the density of 3×104 cells per well in DMEM medium with 10% FBS, 0.1 mM NEAA, and 0.1 mM L-glutamine, 24 hr before transduction. Freshly prepared viruses of the 4F, Oct4, Sox2, c-Myc, and Klf4, were added to the cells. Two days after viral infection, the transduced OG2 MEFs were split into new 6-well plates with irradiated MEF feeders and cultured in iSF1 reprogramming media containing high glucose DMEM, 10% knockout serum, 0.5% N2, 5 ng/ml b-FGF, 2 mM L-glutamine, 0.1 mM 2-mercaptoethanol, 0.1 mM NEAA and 1000 U/ml of LIF. This day was defined as day 0. On day 1, 1 µM of each compound (OAC1, OAC2, and OAC3) was added to the 4F-transduced OG2 MEFs. Treatment was continued for 1 week. When iPSC colonies emerged, these colonies were picked for expansion on the irradiated MEF feeders in mouse ESC medium.

In Vitro Differentiation: For embryoid body formation, iPSCs were treated with 0.25% trypsin-EDTA. The dissociated single cells were transferred into ultra-low-attachment T-25 flasks in the presence of complete growth medium without LIF. Medium was changed every 2 days. After 8 days of suspension culture, one or two embryoid bodies were transferred to 24-well plates coated with 0.1% gelatin and cultured for another 4 days. The resultant cells were stained with anti-FoxA2 (GeneTex, 1250), anti-alpha smooth muscle actin (SMA) (Abcam, 1:500), and anti-βIII Tublin (Tuj1) (Covance, 1:6000) antibodies.

Teratoma Formation: iPSCs were dissociated into single cells and re-suspended at 107 cells/ml. 106 cells in a volume of 100 µl were injected subcutaneously into the dorsal flank of the immunodeficient Nude mice. Four weeks after injection, tumors were dissected from the transplanted mice, fixed in formalin and paraffin-embedded. The tumor tissues were sectioned and stained with hematoxylin and eosin (H&E).

Oct4-luc and Nanog-luc stable cell line construction: The human Oct4 and Nanog promoters were amplified by polymerase chain reaction (PCR) with the following primers: hOct4 forward: 5'-GTG CAG AGA AGT CTA CAT TCC CAT GT-3' (SEQ ID NO:9) and hOct4 reverse: 5'—CGA GAA GGC AAA ATC TGA AGC CAG G-3' (SEQ ID NO:10); hNanog forward: 5'-AGA CAC CCA CCA CCA TGC GTG GCT-3' (SEQ ID NO:11) and hNanog reverse: 5'-TCC TGG AGT CTC TAG ATT-3' (SEQ ID NO:12) using human genomic DNA as the template. Then the promoter sequences were cloned into pGL4.4-luc-Hyg vector (Promega) to get Oct4-luc or Nanog-luc construct and the fidelity of the Oct4 and Nanog promoter DNA sequences was confirmed by bi-directional sequencing. CV 1 cells were transfected with the Oct4-luc or Nanog-luc constructs and the stably-transfected cells were selected by hygromycine resistance.

Compound Screening: The Oct4-luc cells were seeded at 1.75×104 cells per well density into 96-well plates. Compounds were added to cells one day after cell seeding at the concentration of 10 µM for 24 hr in the High-Throughput Screening core facility at City of Hope. Compounds that induced luciferase activity 3-fold or more were selected for further validation in both Oct4-luc and Nanog-luc cells.

Luciferase Reporter Assays: The Oct4-luc or Nanog-luc cells were treated with compound OAC 1 or its structural analogs at 1 µM concentration or at indicated concentrations in triplicates. Other compounds used include 2 µM BIO, 2 µM BIX, 2 µM AzaC, 25 µg/ml Vc, 10 nM Am580, 5 µM tranylcypromine, and 0.5 mM VPA. Luciferase reporter assays were performed as described (51) 24 hr after compound treatment or at indicated time points. For Topflash reporter assays, 0.2 µg β-catenin-responsive Topflash reporter gene plasmid was introduced into CV1 cells using trasfection (Bio-Rad). Compounds were added 6 hr after transfection. Luciferase activity was measured 48 hr after compound treatment using the Glo Luciferase Assay System (Promega).

RT-PCR analysis: Total RNA was purified with Trizol reagent (Invitrogen). Reverse transcription was performed with 1 µg of RNA using Omniscript® Reverse Transcription Kit (Qiagen). Quantitative PCR was performed using iTaq SYBR Green Supermix with Rox (Bio-rad) in Applied Biosystem Step one plus real-time PCR system. The primers for RTPCR include: exo-Oct4-forward 5' GCT CAG TGA TGC TGT TGA TC 3' (SEQ ID NO:13), exo-Oct4-reverse 5' CGG CTT CGG CCA GTA AC 3' (SEQ ID NO:14); exo-Sox2-forward 5' ACT GCA CAT GGC CCA GCA CTA 3' (SEQ ID NO:15), exo-Sox2-reverse 5' CGG CTT CGG CCA GTA AC 3' (SEQ ID NO:16); exo-Klf4-forward 5' CGG ACC ACC TTG CCT TAC ACA 3' (SEQ ID NO:17), exo-Klf4-reverse 5' CGG CTT CGG CCA GTA AC 3' (SEQ ID NO:18); exo-c-Myc-forward 5' CGA GCA CAA GCT CAC CTC TGA 3' (SEQ ID NO:19), exo-c-Myc-reverse 5' CGG CTT CGG CCA GTA AC 3' (SEQ ID NO:20); Oct4-forward 5' GCA TAC TGT GGA CCT CAG GTT 3' (SEQ ID NO:21), Oct4-reverse 5' TCG AAG CGA CAG ATG GTG GT 3' (SEQ ID NO:22); Nanog-forward 5' CTG ACA TGA GTG TGG GTC TTC 3' (SEQ ID NO:23), Nanog-reverse 5' GAA TGG AGG AGA GTT CTT GCA 3' (SEQ ID NO:24); Sox2-forward 5' TGC ACA ACT CGG AGA TCA GCA 3' (SEQ ID NO:25), Sox2-reverse 5' CTC CTG CAT CAT GCT GTA GCT 3' (SEQ ID NO:26); p53-forward 5' TCT GGG ACA GCC AAG TCT GT 3' (SEQ ID NO:27), p53-reverse 5' GGA GTC TTC CAG TGT GAT GA 3' (SEQ ID NO:28); p21-forward 5' CGC ACA GGA GCA AAG TGT GCC GT 3' (SEQ ID NO:29), p21-reverse 5' TGC CCT CCA GCG GCG TCT CCG TG 3' (SEQ ID NO:30); Tet1-forward 5' GAG CCT GTT CCT CGA TGT GG 3' (SEQ ID NO:31), Tet1-reverse 5' CAA ACC CAC CTG AGG CTG TT 3' (SEQ ID NO:32); Tet2-forward 5' AAC CTG GCT ACT GTC ATT GCT CCA 3' (SEQ ID NO:33), Tet2-reverse 5' ATG TTC TGC TGG TCT CTG TGG GAA 3' (SEQ ID NO:34); Actin forward 5' CCG AGC GTG GCT ACA GCT TC 3' (SEQ ID NO:35), Actin reverse 5' ACC TGG CCG TCA GGC AGC TC 3' (SEQ ID NO:36).

Bisulfite Genomic Sequencing: Genomic DNA was isolated from human IMR90 fibroblasts, MEFs, mouse ESCs, 4F+OAC1 and 4F+OAC2-iPSCs by digestion with proteinase K, followed by phenolchloroform extraction and ethanol precipitation. Bisulfite conversion of genomic DNAs was carried out using the EZ DNA Methylation-Gold kit (Zymo Research) according to manufacturer's instruction. The bisulfite-modified DNA was then used as a template for PCR to amplify the promoter regions of Oct4 and Nanog using PCR primers for human OCT4 (1), mouse Oct4 (52) and Nanog (2). The amplified products were cloned into the pCR2.1-TOPO cloning vector (Invitrogen), and 10 randomly selected clones were sequenced with T7 or M13R primers.

Chimera Mouse Production. The 4F+OAC iPSCs derived from OG2/R26 MEFs were microinjected into albino blastocysts to allow identification of chimeras based on coat color markers. Albino blastocyst embryos were generated by injecting female mice with 5 IU of pregnant mare's serum gonadotropin, followed by injecting with 5 IU of human chorionic gonadotropin 48 hours later, and mating to fertile male mice. Hormones for super ovulation were obtained from the National Hormone and Peptide program (Harbor-UCLA, CA). The micro-injected blastocysts were transferred surgically into 2.5 day pseudo-pregnant recipient females, and litters were born naturally or delivered by caesarian section.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

References

Takahashi, K, et al. (2007) Induction of pluripotent stem cells from adult human fibroblasts by defined factors. *Cell* 131, 861-872. Takahashi, K & Yamanaka, S (2006) Induction of pluripotent stem cells from mouse embryonic and adult fibroblast cultures by defined factors. *Cell* 126, 663-676. Yamanaka, S (2007) Strategies and new developments in the generation of patient-specific pluripotent stem cells. *Cell Stem Cell* 1, 39-49. Huangfu, D, et al. (2008) Induction of pluripotent stem cells by defined factors is greatly improved by small-molecule compounds. *Nature Biotechnology* 26, 795-797. Huangfu, D, et al. (2008) Induction of pluripotent stem cells from primary human fibroblasts with only Oct4 and Sox2. *Nature Biotechnology* 26, 1269-1275. Shi, Y, et al. (2008) A combined chemical and genetic approach for the generation of induced pluripotent stem cells. *Cell Stem Cell* 2, 525-528. Shi, Y, et al. (2008) Induction of pluripotent stem cells from mouse embryonic fibroblasts by Oct4 and Klf4 with small-molecule compounds. *Cell Stem Cell* 3, 568-574. Lin, T, et al. (2009) A chemical platform for improved induction of human iPSCs. *Nature Methods* 6, 805-808. Ichida, J K, et al. (2009) A small-molecule inhibitor of tgf-Beta signaling replaces sox2 in reprogramming by inducing nanog. *Cell Stem Cell* 5, 491-503. Zhu, S, et al. (2010) Reprogramming of human primary somatic cells by OCT4 and chemical compounds. *Cell Stem Cell* 7, 651-655. Li, Y, et al. (2010) Generation of iPSCs from mouse fibroblasts with a single gene, Oct4, and small molecules. *Cell Research* 21, 196-204. Esteban, M A, et al. (2010) Vitamin C enhances the generation of mouse and human induced pluripotent stem cells. *Cell Stem Cell* 6, 71-79. Mali, P, et al. (2010) Butyrate greatly enhances derivation of human induced pluripotent stem cells by promoting epigenetic remodeling and the expression of pluripotency-associated genes. *Stem Cells* 28, 713-720. Lyssiotis, C A, et al. (2009) Reprogramming of murine fibroblasts to induced pluripotent stem cells with chemical complementation of Klf4. *PNAS* 106, 8912-8917. Silva, J, et al. (2008) Promotion of reprogramming to ground state pluripotency by signal inhibition. *PLoS Biology* 6, e253. Wang, Q, et al. (2011) Lithium, an anti-psychotic drug, greatly enhances the generation of induced pluripotent stem cells. *Cell Research* 21, 1424-1435. Wang, W, et al. (2011) Rapid and efficient reprogramming of somatic cells to induced pluripotent stem cells by retinoic acid receptor gamma and liver receptor homolog 1. *PNAS* 108, 18283-18288. Niwa, H, Miyazaki, J, & Smith, A G (2000) Quantitative expression of Oct-3/4 defines differentiation, dedifferentiation or self-renewal of ES cells. *Nature Genetics* 24, 372-376. Marson, A, et al. (2008) Wnt signaling promotes reprogramming of somatic cells to pluripotency. *Cell Stem Cell* 3, 132-135. Silva, J, et al. (2009) Nanog is the gateway to the pluripotent ground state. *Cell* 138, 722-737. Judson, R L, Babiarz, J E, Venere, M, & Blelloch, R (2009) Embryonic stem cell-specific microRNAs promote induced pluripotency. *Nature Biotechnology* 27, 459-461. Warren, L, et al. (2010) Highly efficient reprogramming to pluripotency and directed differentiation of human cells with synthetic modified mRNA. *Cell Stem Cell* 7, 618-630. Anokye-Danso, F, et al. (2011) Highly Efficient miRNA-Mediated Reprogramming of Mouse and Human Somatic Cells to Pluripotency. *Cell Stem Cell* 8, 376-388. Loewer, S, et al. (2010) Large intergenic non-coding RNA-RoR modulates reprogramming of human induced pluripotent stem cells. *Nature Genetics* 42, 1113-1117. Liao, B, et al. (2011) MicroRNA cluster 302-367 enhances somatic cell reprogramming by accelerating a mesenchymal-to-epithelial transition. *JBC* 286, 17359-17364. Zhao, Y, et al. (2008) Two supporting factors greatly improve the efficiency of human iPSC generation. *Cell Stem Cell* 3, 475-479. Banito, A, et al. (2009) Senescence impairs successful reprogramming to pluripotent stem cells. *Genes & Dev* 23, 2134-2139. Hong, H, et al. (2009) Suppression of induced pluripotent stem cell generation by the p53-p21 pathway. *Nature* 460, 1132-1135. Kawamura, T, et al. (2009) Linking the p53 tumour suppressor pathway to somatic cell reprogramming. *Nature* 460, 1140-1144. Li, H, et al. (2009) The Ink4/Arf locus is a barrier for iPS cell reprogramming. *Nature* 460, 1136-1139. Utikal, J, et al. (2009) Immortalization eliminates a roadblock during cellular reprogramming into iPS cells. *Nature* 460, 1145-1148. Yoshida, Y, Takahashi, K, Okita, K, Ichisaka, T, & Yamanaka, S (2009) Hypoxia enhances the generation of induced pluripotent stem cells. *Cell Stem Cell* 5, 237-241. Heng, J C, et al. (2010) The nuclear receptor Nr5a2 can replace Oct4 in the reprogramming of murine somatic cells to pluripotent cells. *Cell Stem Cell* 6, 167-174. Miyoshi, N, et al. (2011) Reprogramming of mouse and human cells to pluripotency using mature microRNAs. *Cell Stem Cell* 8, 633-638. Kim, J B, et al. (2009) Oct4-induced pluripotency in adult neural stem cells. *Cell* 136, 411-419. Kim, J B, et al. (2009) Direct reprogramming of human neural stem cells by OCT4. *Nature* 461, 649-643. Boyer, L A, et al. (2005) Core transcriptional regulatory circuitry in human embryonic stem cells. *Cell* 122, 947-956. Jaenisch, R & Young, R (2008) Stem cells, the molecular circuitry of pluripotency and nuclear reprogramming. *Cell* 132, 567-582. Chen, J, et al. (2010) Towards an optimized culture medium for the generation of mouse induced pluripotent stem cells. *JBC* 285, 31066-31072. Szabo, P E, Hubner, K, Scholer, H, & Mann, J R (2002) Allele-specific expression of imprinted genes in mouse migratory primordial germ cells. *Mech Dev* 115, 157-160. Marion, R M, et al. (2009) A p53-mediated DNA damage response limits reprogramming to ensure iPS cell genomic integrity. *Nature* 460, 1149-1153. Sato, N, Meijer, L, Skaltsounis, L, Greengard, P, & Brivanlou, A H (2004) Maintenance of pluripotency in human and mouse embryonic stem cells through activation of Wnt signaling by a pharmacological GSK-3-specific inhibitor. *Nature Medicine* 10, 55-63. Li, W, et al. (2009) Generation of human-induced pluripotent stem cells in the absence of exogenous Sox2. *Stem Cells* 27, 2992-3000. Ito, S, et al. (2010) Role of Tet proteins in 5mC to 5hmC conversion, ES-cell self-renewal and inner cell mass specification. *Nature* 466, 1129-1133. Freudenberg, J M, et al. (2012) Acute depletion of Tet1-dependent 5-hydroxymethylcytosine levels impairs LIF/Stat3 signaling and results in loss of embryonic stem cell identity. *Nucleic Acids Research* 40, 3364-3377. Chambers, I, et al. (2003) Functional expression cloning of Nanog, a pluripotency sustaining factor in embryonic stem cells. *Cell* 113, 643-655. Mitsui, K, et al. (2003) The homeoprotein Nanog is required for maintenance of pluripotency in mouse epiblast and ES cells. *Cell* 113, 631-642. Nichols, J, et al. (1998) Formation of pluripotent stem cells in the mammalian embryo depends on the POU transcription factor Oct4. *Cell* 95, 379-391. Thompson, P A, et al. (2008) Identification of ligand binding by protein stabilization: comparison of ATLAS with biophysical and enzymatic methods. *ADDT* 6, 69-81. Koh, K P, et al. (2011) Tet1 and Tet2 regulate 5-hydroxymethylcytosine production and cell lineage specification in mouse embryonic stem cells. *Cell Stem Cell* 8, 200-213. Dawlaty, M M, et al. (2011) Tet1 is dispensable for maintaining pluripotency and its loss is compatible with embryonic and postnatal development. *Cell Stem Cell* 9, 166-175. Gonzalez, F, Boue, S, & Izpisua Belmonte, J C (2011) Methods for making induced pluripotent stem cells: reprogramming a la carte. *Nat Rev Genet.* 12, 231-242.

What is claimed is:

1. An in vitro method of making an induced pluripotent stem cell comprising:
   (i) contacting a non-pluripotent cell with a compound having the formula:

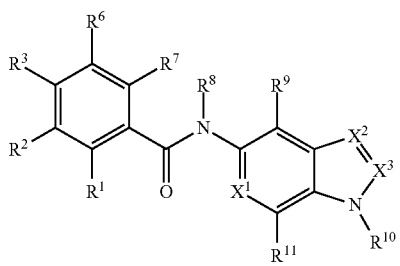

wherein,
   $X^1$ is $C(R^{12})$ or N;
   $X^2$ is $C(R^4)$ or N;
   $X^3$ is $C(R^5)$ or N;
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined to form a substituted or unsubstituted heterocycloalkyl or substituted or unsubstituted heteroaryl; and
   (ii) transfecting said non-pluripotent cell with a nucleic acid encoding a Klf4 protein, introducing a recombinant Klf4 protein into said non-pluripotent cell, or contacting said non-pluripotent cell with a Klf4 expression inducer;
   (iii) transfecting said non-pluripotent cell with a nucleic acid encoding a Sox2 protein, introducing a recombinant Sox2 protein into said non-pluripotent cell, or contacting said non-pluripotent cell with a Sox2 expression inducer;
   (iv) transfecting said non-pluripotent cell with a nucleic acid encoding a cMyc protein, introducing a recombinant cMyc protein into said non-pluripotent cell, or contacting said non-pluripotent cell with a cMyc expression inducer; and
   (v) after steps (i), (ii), (iii), and (iv), allowing said non-pluripotent cell to divide thereby forming said induced pluripotent stem cell.

2. The method of claim 1, further comprising, prior to step (v), transfecting said non-pluripotent cell with a nucleic acid encoding an Oct4 protein or introducing a recombinant Oct4 protein into said non-pluripotent cell.

3. The method of claim 1, further comprising, prior to step (v), transfecting said non-pluripotent cell with a nucleic acid encoding a Nanog protein or introducing a recombinant Nanog protein into said non-pluripotent cell.

4. The method of claim 1, further comprising, prior to step (v), transfecting said non-pluripotent cell with a nucleic acid encoding a Lin28 protein, introducing a recombinant Lin28 protein into said non-pluripotent cell, or contacting said non-pluripotent cell with a Lin28 expression inducer.

5. The method of claim 1, wherein
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, substituted or unsubstituted heteroalkyl, or substituted or unsubstituted heterocycloalkyl.

6. The method of claim 1, wherein
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted alkyl, or substituted or unsubstituted heteroalkyl.

7. The method of claim 1, wherein
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl, substituted or unsubstituted 2 to 10 membered heteroalkyl or substituted or unsubstituted 3 to 8 membered heterocycloalkyl.

8. The method of claim 1, wherein
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, substituted or unsubstituted $C_1$ to $C_{10}$ alkyl or substituted or unsubstituted 2 to 10 membered heteroalkyl.

9. The method of claim 1, wherein
   $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl, unsubstituted heteroalkyl, or substituted heterocycloalkyl.

10. The method of claim 1, wherein
    $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted alkyl or unsubstituted heteroalkyl.

11. The method of claim 1, wherein
    $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl, unsubstituted 2 to 10 membered heteroalkyl, or substituted 3 to 8 membered heterocycloalkyl.

12. The method of claim 1, wherein
    $R^1$, $R^2$, $R^3$, $R^4$, $R^5$, $R^6$, $R^7$, $R^8$, $R^{9, R10}$, $R^{11}$ and $R^{12}$ are independently selected from hydrogen, halogen, —CN, —NO$_2$, —NH$_2$, —CF$_3$, —CCl$_3$, —OH, —SH, —SO$_3$H, —C(O)OH, —C(O)NH$_2$, unsubstituted $C_1$ to $C_{10}$ alkyl or unsubstituted 2 to 10 membered heteroalkyl.

13. The method of claim 1, wherein
    $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, unsubstituted $C_1$ to $C_{10}$ alkyl or unsubstituted 2 to 10 membered heteroalkyl.

14. The method of claim 1, wherein
    $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH$_3$)$_2$, unsubstituted $C_1$ to $C_5$ alkyl or unsubstituted $C_1$ to $C_5$ alkoxy.

15. The method of claim 1, wherein
    $R^1$, $R^2$, $R^3$, $R^4$, $R^5$, $R^6$, $R^7$, $R^8$, $R^9$, $R^{10}$, $R^{11}$ and $R^{12}$ are independently selected from hydrogen, halogen, —N(CH$_3$)$_2$, unsubstituted $C_1$ to $C_5$ alkyl, methoxy, ethoxy or propoxy.

16. The method of claim 1, wherein the compound is selected from the group consisting of
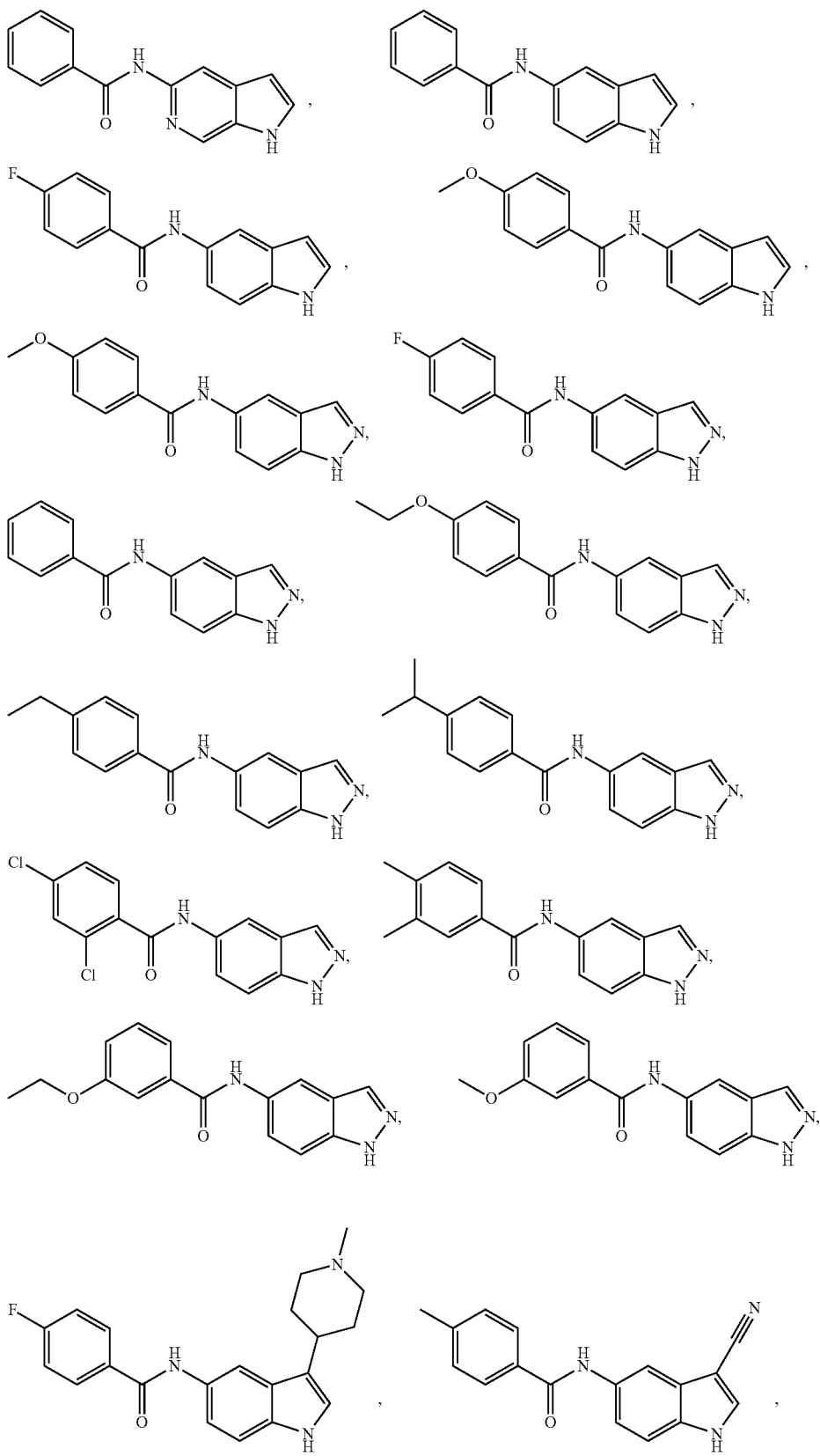

-continued
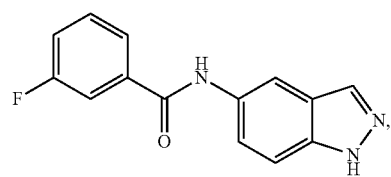 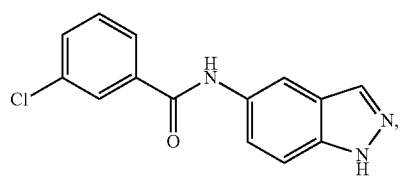
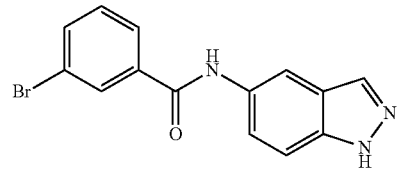 
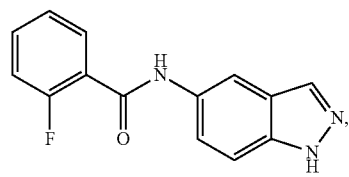 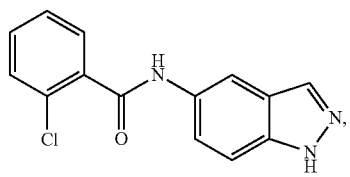 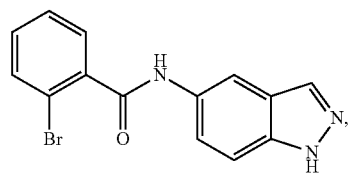
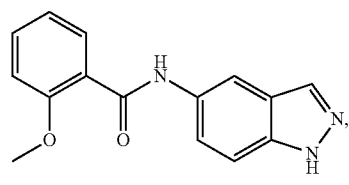 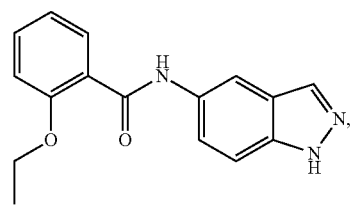 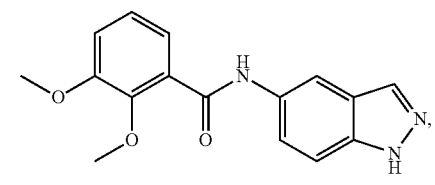
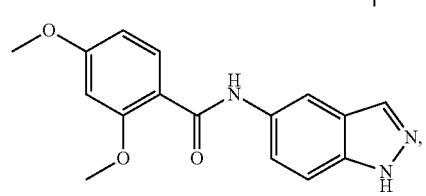 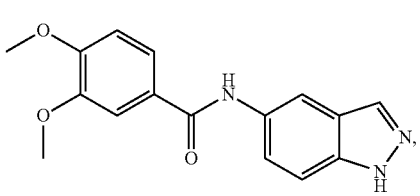
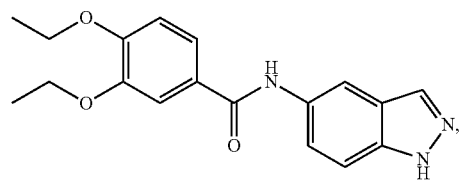 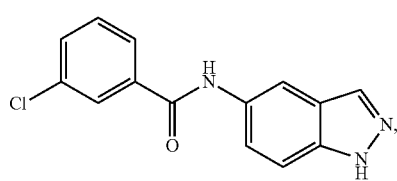
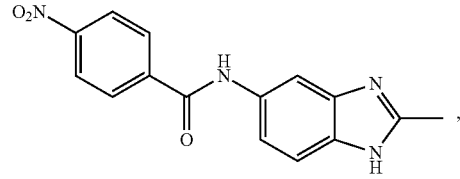 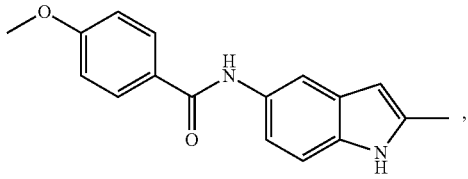
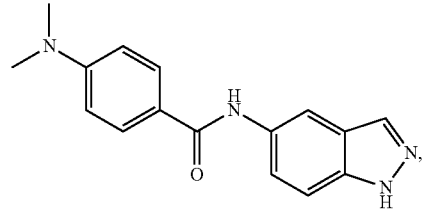 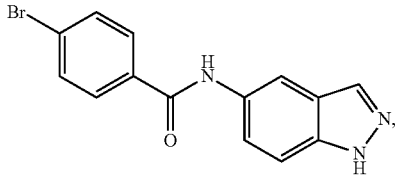 [SMILES: O=C(Nc1ccc2[nH]ncc2c1)c1ccc(Br)cc1]
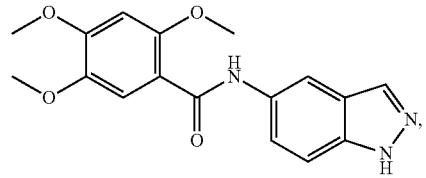 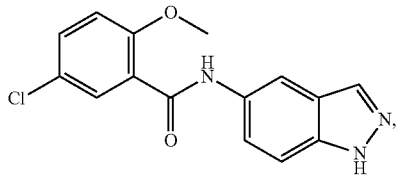

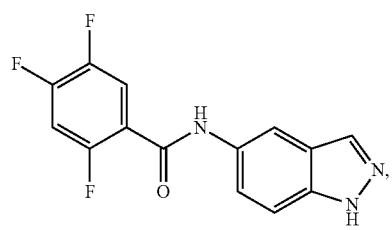
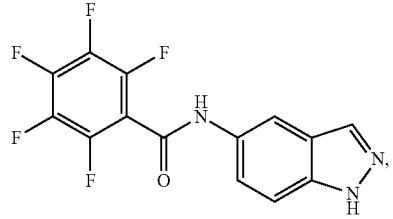
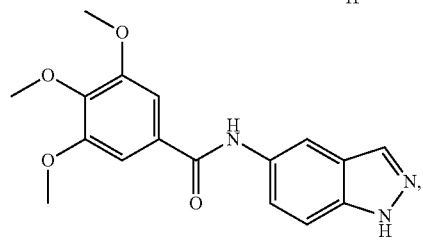
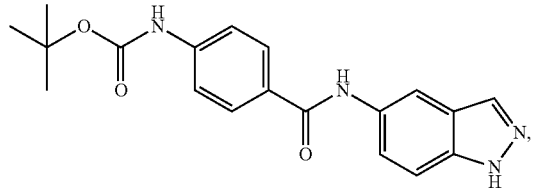
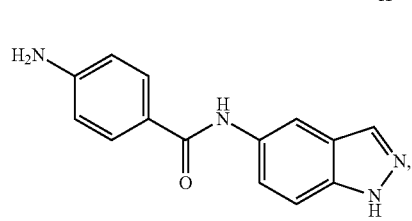
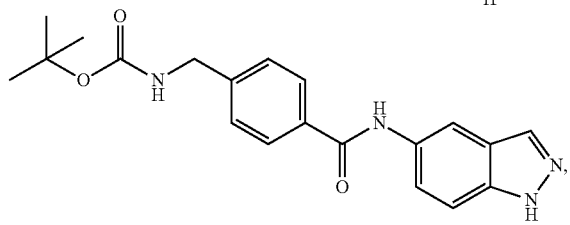
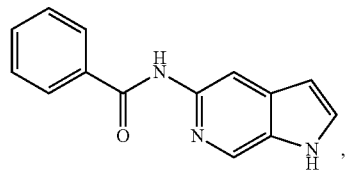, and
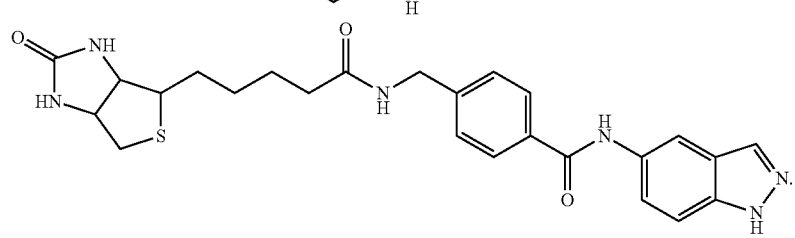
17. The method of claim 1, wherein the compound is selected from the group consisting of
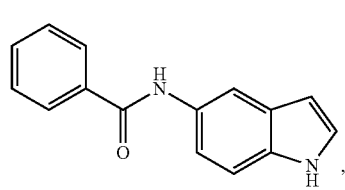
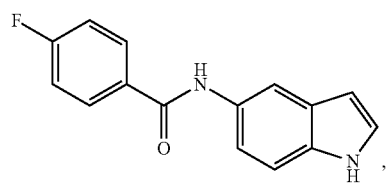

-continued
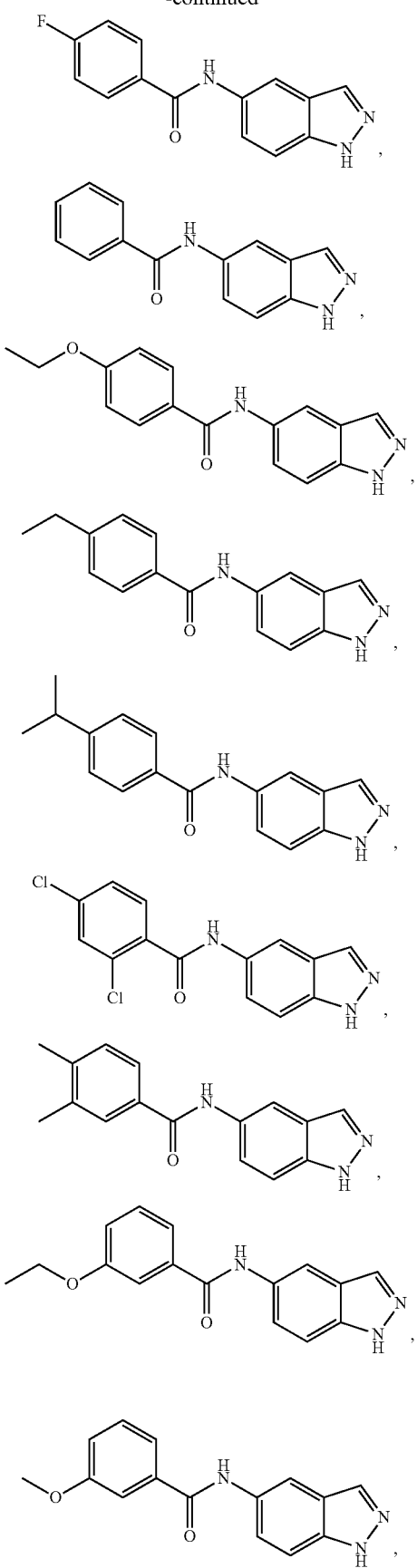
-continued
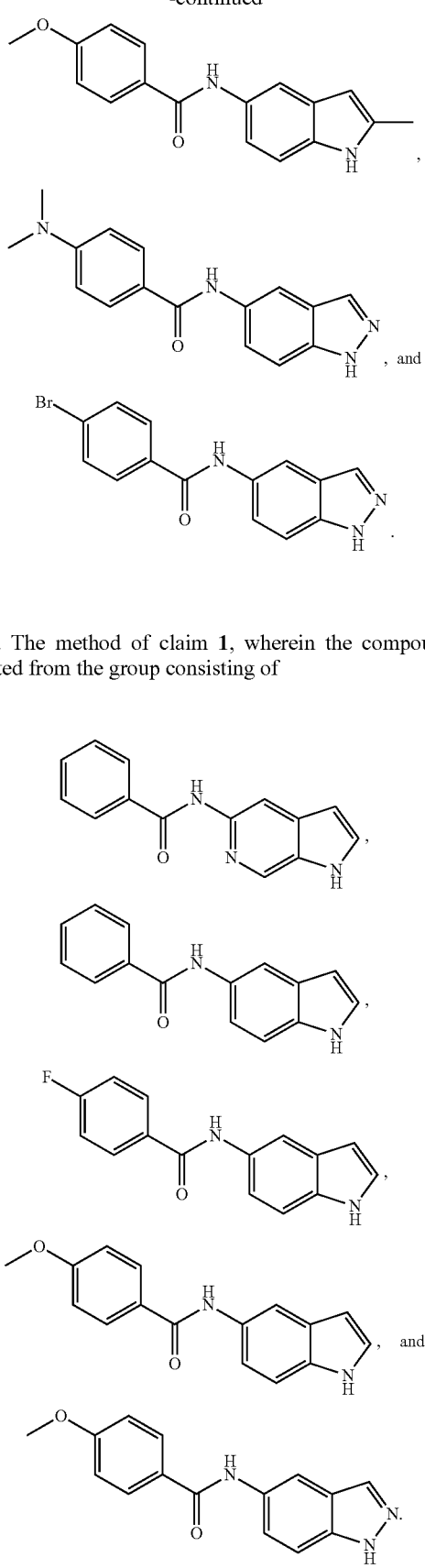
18. The method of claim 1, wherein the compound is selected from the group consisting of 19. The method of claim 1, wherein the compound is selected from the group consisting of

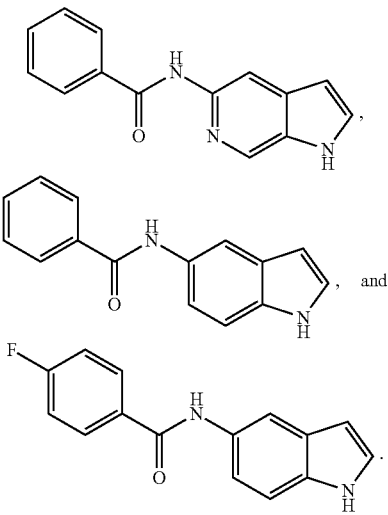

20. The method of claim 1, wherein $R^2$ and $R^3$ are joined together to form a substituted or unsubstituted heteroaryl.

21. The method of claim 2, wherein $R^2$ and $R^3$ are joined together to form a substituted or unsubstituted five-membered heteroaryl.

22. The method of claim 1, wherein step (ii) is contacting said non-pluripotent cell with a Klf4 expression inducer.

23. The method of claim 22, wherein said Klf4 expression inducer is valproic acid, kenpaullone, 5-aminoimidazole-4-carboxamide-I-b-riboside, AMI-5, sodium butyrate, PS48, A-83-1, PD0325901, or SB431542.

24. The method of claim 1, wherein step (iii) is contacting said non-pluripotent cell with a Sox2 expression inducer.

25. The method of claim 24, wherein said Sox2 expression inducer is BIX, BayK, CHIR99021, tranylcypromine, E-616452, Dasatinib, iPY, PP1, n-Butylidenephthalide, AMI-5, PS48, sodium butyrate, A-83-1, PD0325901, SB431542, an Alk5 inhibitor, and LIF.

26. The method of claim 1, wherein step (iv) is contacting said non-pluripotent cell with a cMyc expression inducer.

27. The method of claim 26, wherein said cMyc expression inducer is CHIR99021, BIX, BayK, valproic acid, 5'-azacytidine, 5-aminoimidazole-4-carboxamide-I-b-riboside, AMI-5, sodium butyrate, PS48, A-83-1, SB431542, PD0325901, an Alk5 inhibitor, and LIF.

28. The method of claim 1, further comprising contacting said non-pluripotent cell with a Lin28 expression inducer.

29. The method of claim 27, wherein said Lin28 expression inducer is CHIR99021, BIX, BayK, E-616452, Dasatinib, iPY, PP1, valproic acid, 5'-azacytidine, AMI-5, A-83-01, sodium butyrate, PS48, PD0325901, or SB431542.

* * * * *

UNITED STATES PATENT AND TRADEMARK OFFICE
CERTIFICATE OF CORRECTION

PATENT NO. : 8,962,322 B2
APPLICATION NO. : 14/054551
DATED : February 24, 2015
INVENTOR(S) : Yanhong Shi, Man Lun Yip and Wendong Li Page 1 of 1

It is certified that error appears in the above-identified patent and that said Letters Patent is hereby corrected as shown below:

In the Specification

At Column 1, Line 15, delete "grant NIH NINDS RC1 NS068370 awarded by the National Institute of Health. The Government" and insert the following -- R01 NS059546, and NS068370 awarded by the National Institutes of Health. The government --

Signed and Sealed this
Second Day of September, 2025

Coke Morgan Stewart
*Acting Director of the United States Patent and Trademark Office*